(12) United States Patent
Lin et al.

(10) Patent No.: US 10,517,822 B2
(45) Date of Patent: Dec. 31, 2019

(54) NANOSCALE CARRIERS FOR THE DELIVERY OR CO-DELIVERY OF CHEMOTHERAPEUTICS, NUCLEIC ACIDS AND PHOTOSENSITIZERS

(71) Applicants: The University of Chicago, Chicago, IL (US); The University of North Carolina at Chapel Hill, Chapel Hill, NC (US)

(72) Inventors: Wenbin Lin, Chicago, IL (US); Chunbai He, Chicago, IL (US); Demin Liu, Round Lake, IL (US)

(73) Assignees: The University of Chicago, Chicago, IL (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/034,799

(22) PCT Filed: Nov. 6, 2014

(86) PCT No.: PCT/US2014/064388
§ 371 (c)(1),
(2) Date: May 5, 2016

(87) PCT Pub. No.: WO2015/069926
PCT Pub. Date: May 14, 2015

(65) Prior Publication Data
US 2016/0346204 A1 Dec. 1, 2016

Related U.S. Application Data

(60) Provisional application No. 61/900,698, filed on Nov. 6, 2013.

(51) Int. Cl.
*A61K 9/127* (2006.01)
*A61K 31/663* (2006.01)
*A61K 9/51* (2006.01)
*C12N 15/11* (2006.01)
*A61K 45/06* (2006.01)
*A61K 31/664* (2006.01)
*A61K 31/713* (2006.01)
*C12N 15/113* (2010.01)

(52) U.S. Cl.
CPC .......... *A61K 9/1271* (2013.01); *A61K 31/664* (2013.01); *A61K 31/713* (2013.01); *A61K 45/06* (2013.01); *C12N 15/111* (2013.01); *C12N 15/113* (2013.01); C12N 2310/11 (2013.01); C12N 2310/14 (2013.01); C12N 2310/141 (2013.01); C12N 2320/31 (2013.01); C12N 2320/32 (2013.01)

(58) Field of Classification Search
CPC .. A61K 9/1271; A61K 31/664; A61K 31/713; A61K 45/06; C12N 15/111; C12N 15/113; C12N 2310/11; C12N 2310/14; C12N 2310/141; C12N 2320/31; C12N 2320/32
USPC .................................................. 424/450, 490
See application file for complete search history.

(56) References Cited

U.S. PATENT DOCUMENTS

| | | |
|---|---|---|
| 4,405,771 A | 9/1983 | Jagur |
| 5,147,806 A | 9/1992 | Kamin et al. |
| 5,213,788 A | 5/1993 | Ranney |
| 5,591,730 A | 1/1997 | Stoller et al. |
| 5,641,623 A | 6/1997 | Martin |
| 5,827,925 A | 10/1998 | Tremont et al. |
| 5,858,784 A | 1/1999 | Debs et al. |
| 5,871,710 A | 2/1999 | Bogdanov et al. |
| 6,013,638 A | 1/2000 | Crystal et al. |
| 6,022,737 A | 2/2000 | Niven et al. |
| 6,136,295 A | 10/2000 | Edwards et al. |
| 6,180,082 B1 | 1/2001 | Woltering et al. |
| 6,384,019 B1 | 5/2002 | Myhren et al. |
| 6,878,838 B2 | 4/2005 | Lin et al. |
| 6,984,400 B2 | 1/2006 | Golomb et al. |
| 7,354,912 B2 | 4/2008 | Lichtenberger |
| 7,704,972 B2 | 4/2010 | Couvreur et al. |

(Continued)

FOREIGN PATENT DOCUMENTS

| | | |
|---|---|---|
| CN | 1 673 258 | 9/2005 |
| CN | 102573914 A | 7/2012 |

(Continued)

OTHER PUBLICATIONS

Cunha et al. (J. Materials Chemistry B, vol. 1, No. 8, Jan. 2013, p. 1101-1108). (Year: 2013).*

(Continued)

*Primary Examiner* — Janet L Epps-Smith
(74) *Attorney, Agent, or Firm* — Jenkins, Wilson, Taylor & Hunt, P.A.

(57) ABSTRACT

Nanoscale coordination polymer nanoparticles for the co-delivery of multiple therapeutic agents are described. The multiple therapeutic agents can include a combination of different chemotherapeutic agents, a combination of one or more chemotherapeutic agents and one or more nucleic acids, such as small interfering RNA (siRNA) or microRNA, a combination of one or more chemotherapeutic agents and a photosensitizer (i.e., for use in photodynamic therapy), or a plurality of different siRNAs. Pharmaceutical formulations including the nanoparticles, methods of using the nanoparticles to treat cancer, and methods of making the nanoparticles are also described.

13 Claims, 11 Drawing Sheets

(56) References Cited

U.S. PATENT DOCUMENTS

| | | |
|---|---|---|
| 7,803,785 B2 | 9/2010 | Gallop et al. |
| 8,158,153 B2 | 4/2012 | Liversidge et al. |
| 8,653,292 B2 | 2/2014 | Hafizovic et al. |
| 8,722,018 B2 | 5/2014 | Port et al. |
| 9,072,774 B2 | 7/2015 | Zheng et al. |
| 9,693,957 B2 | 7/2017 | Lin et al. |
| 2001/0018187 A1 | 8/2001 | Sun et al. |
| 2002/0115747 A1 | 8/2002 | Feldheim et al. |
| 2002/0187184 A1 | 12/2002 | Golomb et al. |
| 2005/0147963 A1 | 7/2005 | Su et al. |
| 2006/0204754 A1 | 9/2006 | Kang |
| 2006/0210639 A1 | 9/2006 | Liversidge et al. |
| 2006/0228554 A1 | 10/2006 | Tan et al. |
| 2006/0233883 A1 | 10/2006 | Ishihara et al. |
| 2007/0088161 A1 | 4/2007 | Stockel et al. |
| 2008/0045699 A1 | 2/2008 | Labow et al. |
| 2008/0063714 A1 | 3/2008 | Sahouani et al. |
| 2008/0095699 A1 | 4/2008 | Zheng et al. |
| 2008/0124281 A1 | 5/2008 | Gao et al. |
| 2008/0280851 A1 | 11/2008 | Myhren et al. |
| 2008/0286352 A1 | 11/2008 | Kumar et al. |
| 2008/0292714 A1 | 11/2008 | Garlich |
| 2009/0317335 A1 | 12/2009 | Lin et al. |
| 2011/0053862 A1 | 3/2011 | Xie et al. |
| 2011/0135571 A1 | 6/2011 | Lin et al. |
| 2011/0238001 A1 | 9/2011 | Chen et al. |
| 2011/0281815 A1 | 11/2011 | Ahrabi et al. |
| 2012/0142641 A1 | 7/2012 | Venkatraman |
| 2012/0253191 A1 | 10/2012 | Zheng et al. |
| 2012/0301537 A1 | 11/2012 | Ishida et al. |
| 2013/0171228 A1 | 7/2013 | Morris |
| 2014/0107333 A1 | 4/2014 | Ma et al. |
| 2014/0127763 A1 | 5/2014 | Zheng et al. |
| 2014/0234210 A1 | 8/2014 | Lin et al. |
| 2014/0235568 A1 | 8/2014 | Song et al. |
| 2017/0333347 A1 | 11/2017 | Lin et al. |

FOREIGN PATENT DOCUMENTS

| | | |
|---|---|---|
| EP | 2729180 B1 | 1/2019 |
| EP | 3494974 A1 | 6/2019 |
| JP | 2010-523595 A | 7/2010 |
| JP | 6049712 B2 | 12/2016 |
| WO | WO 2004/028508 A1 | 4/2004 |
| WO | WO 2006/087722 A1 | 8/2006 |
| WO | WO2006/102117 | 9/2006 |
| WO | WO2007/090295 | 8/2007 |
| WO | WO2007/108618 | 9/2007 |
| WO | WO2007/124131 | 11/2007 |
| WO | WO 2008/016172 A1 | 2/2008 |
| WO | WO2008/124636 A2 | 10/2008 |
| WO | WO 2009/014532 A1 | 1/2009 |
| WO | WO2009/139939 | 11/2009 |
| WO | WO2012/042024 | 4/2010 |
| WO | WO 2010/065751 A2 | 6/2010 |
| WO | WO2013/009701 | 1/2013 |
| WO | PCT/2013/068965 | 5/2013 |
| WO | WO 2012/161196 A1 | 7/2014 |
| WO | WO 2015/149068 A1 | 10/2015 |
| WO | WO 2015/149072 A1 | 10/2015 |

OTHER PUBLICATIONS

Notice of allowance and Fee(s) Due, Examiner-Initiated Interview Summary, and Notice of Allowability Corresponding to U.S. Appl. No. 14/131,575 dated Feb. 27, 2017.

Communication of the Extended European Search Report corresponding to European Application No. 14860910.0 dated Jun. 20, 2017.

Cunha et al., "Rationalization of the entrapping of the bioactive molecules into a series of functionalized porous zirconium terephthalate MOFs," J. Mater. Chem., vol. 1, pp. 1101-1108 (2013).

Huxford-Phillips et al., "Lipid-coated nanoscale coordication polymers for targeted cisplatin delivery," RSC Advances, vol. 3, No. 34, pp. 14438-14443 (Jan. 2013).

Cutler et al., "Spherical Nucleic Acids," Journal of the American Chemical Society, 134, p. 1376-1391 (2012).

Jin et al., "Targeting-triggered porphysome nanostructure disruption for activatable photodynamic therapy," Adv. Healthcare Mater., vol. 3, No. 8 pp. 1240-1249 (2014).

Liu et al., "Self-assembled nanoscale coordination polymers with trigger release properties for effective anticancer therapy,"Nature Communications, vol. 5, 4128, pp. 1-25 (2014).

Lovell et al., "Porphysome nanovesicles generated by porphyrin bilayers for use as multimodal biophotonic contrast agents," Nat. Mater., vol. 10 pp. 324-332 (2011).

Cavka et al., "A new zirconium inorganic building brick forming metal organic frameworks with exceptional stability," J Am Chem Soc, 130, pp. 13850-13851 (2008).

Chen et al., "Co-delivery of Doxorubicin and Bcl-2 siRNA by Mesoporous Silica nanoparticles Enhances the Efficacy of Chemotherapy in Multidrug-Resistant Cancer Cells**," small, 5, No. 23, p. 2673-2677 (2009).

Cho et al., "Targeted delivery of siRNA-generating DNA nanocassettes using multifunctional nanoparticles," small, 9, No. 11, p. 1964-1973 (2013).

Communication of European publication Number and information on the application of Article 67(3) EPC for European Application No. 14860910.0 (Aug. 18, 2016).

Dekrafft et al., "Iodinated nanoscale coordination polymers as potential contrast agents for computed tomography**," Angew Chem Int Edit 48, p. 9901-9904 (2009).

Dinca et al., "Hyddrogen Storage in Microporous Metal-Organic Frameworks with Exposed Metal Sites," Angew Chem Int Edit 47, p. 6766-6779 (2008).

Fire et al., "Potent and specific genetic interference by double-stranded RNA in Caenorhabditis elegans," Nature 391, p. 806-811 (1998).

Foged, "siRNA Delivery with Lipid-based Systems:Promises and Pitfalls," Curr Top Med Chem, 12, p. 97-107 (2012).

Horcajada et al., "Porous metal-organic-framework nanoscale carriers as a potential platform for drug delivery and imaging," Nat Mater 9, p. 172-178 (2010).

Kelland, "The resurgence of platinum-based cancer chemotherapy,". Nature Reviews Cancer , 7, 573-584 (2007).

Lee et al., "Metal-organic framework materials as catalysts," Chem Soc Rev, 38, 1450-1459 (2009).

Letter regarding an Office Action corresponding to Japanese Patent Application No. 2014-520238 dated Mar. 14, 2016.

Li et al., "Design and synthesis of an exceptionally stable and highly porous metal-organic framework," Nature 402, p. 276-279 (1999).

Liu et al., "Phosphorescent nanoscale coordination polymers as contrast agents for optical imaging," Angew Chem Int Edit, 50, p. 3696-3700 (2011).

Lowery et al., "Cost-effectiveness of early palliative care intervention in recurrent platinum-resistant ovarian cancer," Gynecol Oncol 2013, 130, p. 426-430 (2013).

Official Action corresponding to U.S. Appl. No. 14/131,575 dated Aug. 12, 2016.

Schaate et al., "Modulated synthesis of Zr-Based metal-organic frameworks: from nano to single cystals," Chem-Eur J, 17, p. 6643-6651 (2011).

Shahzad et al., "Novel strategies for reversing platinum resistance," Drug Resist Updates 12, p. 148-152 (2009).

Wang et al., "Postsynthetic modification of metal-organic frameworks," Chem Soc Rev 38, p. 1315-1329 (2009).

Xiong et al., "Traceable multifunctional micellar nanocarriers for cancer-targeted co-delivery of MDR-1 siRNA anddoxorubicin," ACS nano, vol. 5, No. 6, p. 5202-5213 (2011).

Yellepeddi et al., "Comparative evaluation of small-molecule chemosensitizers in reversal of cisplatin resistance in ovarian cancer cell,"Anticancer Res 32, p. 3651-3658 (2012).

Coleman, R. L.; Monk, B. J.; Sood, A. K.; Herzog, T. J. Nat Rev Clin Oncol , 10, p. 211-224 (2013).

(56) References Cited

OTHER PUBLICATIONS

Bowden et al., "Hydrothermal syntheses and crystal structures of three zinc succinates: Zn(C4H4O4)-α, Zn(C4H4O4)-β and K2Zn(C4H4O4)2," Dalton Transactions. pp. 936-939 (2003).
Catala et al., "Cyanide-Bridged CRIII-NiII Superparamagnetic Nanoparticles," Advances Materials. vol. 15, No. 10 pp. 826-829 (2003).
Chebbi et al., "In vitro assessment of liposomal neridronate on MDA-MB-231 human breast cancer cells," International Journal of Pharmaceutics 383 pp. 116-122 (2010).
Chen et al., "Synthesis, characterization and osteoconductivity properties of bone fillers based on alendronate-loaded poly(e-caprolactone)/hydroxyapatite microspheres," J Mater Sci, vol. 22 pp. 547-555 (2011).
Extended European Search Report corresponding to Application No. 12810577.2 dated Feb. 4, 2015.
Giger et al. "Gene delivery with bisphosphonate-stabilized calciun1 phosphate nanoparticles," Journal of Controlled Release. vol. 150 pp. 87-93 (2011).
Giraudo et al. "An amino-bisphosphonate targets MMP-9-expressing macrophages and anglogenesis to impair cervical carcinogenesis," The Journal of Clinical Investigation. vol. 114, No. 5 pp. 623-633 (2004).
Giustini at al., "Microstructure and Dynamics of the Water-in-Oil CTAB/n-Pentanol/n-Hexane/Water Microemulsion: A Spectroscopic and Conductivity Study," Journal of Physical Chemistry. vol. 100, No. 8 pp. 3190-3198 (1996).
Graf et al., "A General Method for the Controlled Embedding of Nanoparticles in Silica Colloids," Langmuir. vol. 22, No. 13 pp. 2604-5610 (2006).
Graf et al., "A General Method to Coat Colloidal Particles with Silica," Langmuir. vol. 19, No. 17 pp. 6693-6700 (2003).
Hafeman et al., "Evaluation of liposomal clodronate for treatment of malignant histiocytosis in dogs," Cancer Immunol. Immunother. vol. 59 pp. 441-452 (2010).
He et al., Nanoscale Metal-Organic Frameworks for the Co-Delivery of Cisplatin and Pooled siRNAs to Enhance Therapeutic Effcacy in Drug-Resistant Ovarian Cancer Cells, J. Am. Chem. Soc. 136, p. 5181-5184 (2014).
Kalayda et al., "Synthesis, Structure, and Biological Activity of New Azine-Bridged Dnuclear Platinum (II) Complexes," Eur. J. Inorg. Chem. pp. 4347-4355 (2003).
Leigh, "Comprehensive Coordination Chemistry II From Bioiogy to Nanotechnology," Journal of Organometallic Chemistry. vol. 689, No. 16 pp. 2733-2742 (2004).
Liu et al., "Coercing bisphosphonates to kill cancer cells with nanoscale coordination polymerst," Chem. Commun. vol. 48 pp. 2663-2670 (2012).
Mack et al, "The effects of terbium on the cellular accumulation of cisplatin in MDA-MB-231 human breast tumor cells," Cancer Chemotherapy and Pharmacology. vol. 39 pp. 217-222 (1997).
Matsumura, Y., and Maeda, H., "A New Concept for Macromolecular Therapeutics in Cancer Chemotherapy: Mechanism of Tumoritropic Accumulation of Proteins and the Antitumor Agent Smancs," Cancer Research. vol. 46 pp. 6387-6392 (1985).
Meng, H.; Liong, M.; Xia, T.; Li, Z.; Ji, Z.; Zink, J. I.; Nel, A. E. ACS nano 4, p. 4539-4550 (2010).
Mukhopadhyay et al., "Conjugated Platinum (IV)—Peptide Compiexes for Targeting Angiogenic Tumor Vasculature," Bioconjugate Chemistry. vol. 19, No. 1 pp. 39-49 (2008).
Notification Concerning Transmittal of International Preliminary Report on Patentability (Chapter I of the Patent CooperationTreaty) corresponding to International Patent Application No. PCT/US2012/045954 dated Jan. 23, 2014.
Notification of Transmittal of the International Search Report and the Written Opinion of the International Searching Authority, or the Declaration corresponding to internationai Apptication No. PCT/US2012/045954 dated Jan. 28, 2013.
Notification of Transmittal of the International Search Report and the Written Opinion of the International Searching Authority, or the Declaration corresponding to International Application No. PCT/US14/64388 dated Feb. 28, 2015.
Notification Concerning Transmittal of International Preliminary Report on Patentability (Chapter 1 of the Patent CooperationTreaty) corresponsing to International Patent Application No. PCT/US2014/064388 dated May 19, 2016.
Restriction Requirement corresponding to U.S. Appl. No. 14/131,575 dated Nov. 20, 2015.
Rieter, W. J.; Taylor, K. M. L.; an, H. Y.; Lin, W. L.; Lin, W. B. J Am Chem Soc, 128, 9024 (2006).
Rieter et al., "Nanoscale Coordination Polymers for Platinum-Based Anticancer Drug Delivery," Journal of the American Chemical Society. vol. 130 pp. 11584-11585 (2008).
Roberts, D.; Schick, J.; Conway, S.; Biade, S.; Laub, P. B.; Stevenson, J. P.; Hamilton, T. C.; O'Dwyer, P. J.; Johnson, S. W. Brit J Cancer , 92, 1149 (2005).
Rosi, N. L.; Kim, J.; Eddaoudl, M.; Chen, B. L.; O'Keeffe, M.; Yaghi, O. M. J Am Chem Soc, 127, 1504 (2005).
Salzano et al. "Self-assembly nanoparticles for the delivery of bisphosphonates into tumors," International Journal of Pharmaceutics 403 pp. 292-297 (2011).
Sheats, "History of Organmetallic Polymers," Journal of Macromolecular Science: Part A—Chemistry. vol. 15, No. 6 pp. 1173-1199 (1981).
Shi et al., "In-vitro osteogensis of synovium stem cells induced by controlled release of bisphosphate additives from microspherical meso porous silica composite," Biomaterials. vol. 30, No. 23-24, pp. 3996-4005 (2009).
Shmeeda et al. "Delivery of zoledronic acid encapsulated in folate-targeted liposome results in potent in vitro cytotoxic activity on tumor cells," Journal of Controlled Release 146 pp. 76-83 (2010).
Taylor-Pashow, K. M. L.; Della Rocca, J.; Xie, Z.; Tran, S.; Lin, W. Journal of the American Chemical Society 131, 14261 (2009).
Uemura, T., and Kitagawa, S., "Prussian Blue Nanoparticles Protected by Poly(vinylpyrrolidone)," Journal of the American Chemical Society. vol. 125, No. 26 pp. 7814-7815 (2003).
Vaucher et al., "Synthesis of Prussian Blue Nanoparticles and Nanocrystal Superlattices in Reverse Microemulsions," Angew. Chem. Int. Ed. vol. 39, No. 10 pp. 1793-1796 (2000).
Vaucher et al., "Molecule-Based Magnetic Nanoparticles: Synthesis of Cobalt Hexacyanoferrate, Cobalt Pentacyanonitrosylferrate, and Chromium Hexacyanochromate Coordination Polymers in Water-in-Oil Microemulsions," Nano Letters. vol. 2, No. 3 pp. 225-229 (2002).
Vaughan, S.; Coward, J. I.; Bast, R. C.; Berchuck, A.; Berek, J. S.; Brenton, J. D. et al. Nat Rev Cancer, 11, 719 (2011).
White et al., "Photooxidation of Diglycine in Confined Media. Application of the Microreactor Model for Spin-Correlated Radical Pairs in Reverse Micelles and Water-in-Oil Microemulsions," Langmuir. vol. 21, No. 7 pp. 2721-2727 (2005).
Wong et al., "Flouresence Probing of Inverted Micelles. The State of Solubized Water Clusters in Alkane-Diisooctyl Sulfosuccinate (Aerosol OT) Solution," Journal of the American Chemical Society. vol. 98, No. 9 pp. 2391-2397 (1976).
Xu, W., and Akins, D.L., "Reverse micellar sunthesis of CdS nanoparticles and self-assembly into a superlattice," Materials Letters. vol. 58 pp. 2623-2626 (2004).
Yamada et al., "Synthesis and Isolation of Cobalt Hexacyanoferrate/Chromate Metal Coordination Nanopolymers Stabilized by Alkylamino Ligand with Metal Elemental Control," Journal of the American Chemical Society. vol. 126 pp. 9482-9483 (2004).
Yu et al., "Immobilization of polymer-stabilized metal colloids by a modified coordination capture: preparation of supported metal colloids with singular catalytic properties," Journal of Molecular Catalysis A: Chemical. vol. 142 pp. 201-211 (1999).
Zhang et al., "Three-Dimensional Lanthanoid-Containing Coordination Frameworks: Structure, Magnetic and Flourescent Properties," European Journal of Inorganic Chemistry. pp. 766-772 (2005).
Zhang, K.; Hao, L. L.; Hurst, S. J.; Mirkin, C. A. Journal of the American Chemical Society, 134, 16488 (2012).
Zou, S.; Cao, N.; Cheng, D.; Zheng, R.; Wang, J.; Zhu, K.; Shuai, X. Int J Nanomed, 7, 3823 (2012).

(56) References Cited

OTHER PUBLICATIONS

Office Action (Restriction Requirement) corresponding to U.S. Appl. No. 15/613,847 dated Jun. 18, 2018.
Office Action corresponding to Japanese Patent Application No. 2016-528894 dated Jul. 17, 2018.
Office Action corresponding to U.S. Appl. No. 15/613,847 dated Dec. 10, 2018.
PubChem Open Chemistry Database, Platinum (2+), date unavailable.
European Decision to Grant corresponding to European Patent Application Serial No. 12810577.2 dated Jan. 7, 2019.
Office Action corresponding to European Patent Application Serial No. 14860910.0 dated Jan. 29, 2019.
Office Action corresponding to Japanese Patent Application No. 2016-528894 dated Feb. 4, 2019.
Che et al., "Generation of Binuclear (d8.d8) Platinum and Rhodium Complexes by Pulse Radiolysis", American Chemical Society, vol. 106, No. 18, pp. 5143-5145 (1984).
Kitabwalla et al., "RNA interference—a new weapon against HIV and beyond," The New England Journal of Medicine, vol. 347, No. 17, pp. 1364-1367 (Oct. 24, 2002).
Letter regarding decision to grant a Japanese Patent corresponding to Japanese Patent Application No. 2014-520238 dated Oct. 31, 2016.
Official Action corresponding to U.S. Appl. No. 14/131,575 dated Dec. 16, 2016.
Official Action corresponding to European Patent Application Serial No. 12810577.2 dated Jan. 5, 2017.
"Small Interfering RNA," pp. 1-6, downloaded from https://en.wikipedia.org/wiki/Small_interfering_RNA on Nov. 11, 2016.
European Intention to Grant for European Patent Application Serial No. 12810577.2 dated Sep. 17, 2018.
Office Action corresponding to Chinese Patent Appiication No. 2014800722580 dated Jun. 27, 2018.
Communication of European publication number and information on the application of Article 67(3) EPC for European Application No. 19151591.5 dated May 15, 2019.
Extended European Search Report corresponding to European Application No. 19151591.5 dated May 13, 2019.
Office Action corresponding to U.S. Appl. No. 15/613,847 dated Jun. 5, 2019.
Office Action corresponding to Chinese Patent Application No. 2014800722580 dated Mar. 20, 2019.
Advisory Action corresponding to U.S. Appl. No. 15/613,847 dated Aug. 13, 2019.
Decision to Grant corresponding to Japanese Patent Application No. 2016-528894 dated Aug. 19, 2019.

* cited by examiner

NANOSCALE CARRIERS FOR THE DELIVERY OR CO-DELIVERY OF CHEMOTHERAPEUTICS, NUCLEIC ACIDS AND PHOTOSENSITIZERS

RELATED APPLICATIONS

The presently disclosed subject matter claims the benefit of U.S. Provisional Patent Application Ser. No. 61/900,698, filed Nov. 6, 2013; the disclosure of which is incorporated herein by reference in its entirety.

GOVERNMENT INTEREST

This invention was made with government support under Grant Number CA151455 awarded by the National Institutes of Health and Grant Number DMR0906662 awarded by the National Science Foundation. The government has certain rights in the invention.

TECHNICAL FIELD

The presently disclosed subject matter provides a nanocarrier platform based on metal-organic matrix materials, such as nanoscale coordination polymers (NCPs) (including, metal-organic frameworks (MOFs), or nanoscale metal-organic frameworks (NMOFs)), for the co-delivery of two or more therapeutics. In some embodiments, the platform is for the co-delivery of chemotherapeutics (e.g., small molecule and/or non-nucleic acid chemotherapeutics) and nucleic acids, such as small interfering RNAs micro RNAs, antisense oligonucleotide, and DNA, for enhanced anticancer therapy. In some embodiments, the platform is for the co-delivery of chemotherapeutics and photosensitizers for combined chemotherapy and photodynamic therapy (PDT). In some embodiments, the platform is used to deliver one or more siRNAs to treat a disease, such as cancer.

Abbreviations

° C.=degrees Celsius
%=percentage
μl=microliter
μM=micromolar
AS ODN=antisense oligonucleotide
BSA=bovine serum albumin
cisPt=cisplatin
cm=centimeter
DLS=dynamic light scattering
DMF=dimethylformamide
DMSO=dimethylsulfoxide
DOPA=1,2-dioleoyl-sn-glycero-3-phosphate sodium salt
DOPC=1,2-dioleoyl-sn-glycero-3-phosphocholine
DOPE=dioleoyl L-α-phosphatidylethanol amine
DOTAP=1,2-dioleoyl-3-trimethylammonium propane
DSPE-PEG$_{2k}$=1,2-distearoyl-sn-glycero-3-phosphoethanolamine-N-[amino(polyethylene glycol)2000]
EDS=energy dispersive X-ray spectroscopy
EtOH=ethanol
g=gram
h=hour
IC$_{50}$=fifty percent inhibitory concentration
ICP-MS=inductively coupled plasma-mass spectrometry
kg=kilogram
mg=milligram
min=minute
miRNA=micro ribonucleic acid
mL=milliliter
mM=millimolar
mmol=millimole
Mn=manganese
MOF=metal-organic framework
MRI=magnetic resonance imaging
NCP=nanoscale coordination polymer
nm=nanometer
NMOF=nanoscale metal-organic frameworks
NMR=nuclear magnetic resonance
MW=molecular weight
PBS=phosphate buffered saline
PDI=polydispersity index
PDT=photodynamic therapy
PEG=polyethylene glycol
PET=positron emission tomography
PS=photosensitizer
Pt=platinum
PVP=polyvinylpyrrolidone
r=radius
RES=reticuloendothelial system
RGD=arginine-glycine-aspartic acid
RNAi=ribonucleic acid interference
rpm=revolutions-per-minute
SBU=secondary building units
siRNA=small interfering ribonucleic acid
SPECT=single photon emission computed tomography
TEM=transmission electron microscopy
Zn=zinc

BACKGROUND

Nucleic acids have generated great interest for use in treating diseases, such as cancer. In spite of their potential in cancer therapy, nucleic acids such as small interfering RNAs (siRNAs) and micro RNAs (miRNAs) can have limitations. First, these nucleic acids can be vulnerable to degradation by enzymes that are ubiquitous in the environment. Second, the effects of nucleic acids (such as siRNAs and miRNAs) are typically transient. Third, nucleic acids themselves cannot enter the cells and the existing delivery systems are either of low delivery efficiency or fail to prolong circulation in the body after systemic administration.

Photodynamic therapy (PDT) can also be an effective anticancer treatment option. PDT involves the administration of a tumor-localizing photosensitizer (PS) followed by light activation to generate highly cytotoxic reactive oxygen species (ROS), particularly single oxygen ($^1O_2$), which trigger cell apoptosis and necrosis. By localizing both the PS and the light exposure to tumor regions, PDT can selectively kill tumor cells while preserving local tissues. PDT has been used to treat patients with many different types of cancer, including head and neck tumors, breast cancer, gynecological tumors, brain tumors, colorectal cancer, mesothelioma, and pancreatic cancer. The use of PDT for treating cancers in the head and neck is particularly advantageous over traditional treatment modalities, e.g., surgery and irradiation, as PDT causes less destruction of surrounding tissues and reduces aesthetic and functional impairments. Porphyrin molecules such as PHOTOFRIN®, VERTEPORFIN®, FOSCAN®, PHOTOCHLOR®, and TALAPORFIN® are among the most commonly used PSs for PDT. However, although they have efficient photochemistry for ROS generation, their suboptimal tumor accumulation after systemic administration can limit the efficacy of PDT in the clinic.

Accordingly, there is an ongoing need for additional delivery vehicles for improving the delivery (e.g., the targeted delivery) of both nucleic acid and PS therapeutics. In particular, there is a need for delivery vehicles that can deliver nucleic acids or PSs in combination with other therapeutics (e.g., non-nucleic acid/non-PS chemotherapeutics) in order to increase treatment efficacy, e.g., by overcoming drug resistance by treating cancers via multiple mechanisms of action.

SUMMARY

In some embodiments, the presently disclosed subject matter provides a nanoscale particle for co-delivery of a plurality of therapeutic agents, said nanoscale particle comprising: a core comprising a metal-organic matrix material, optionally wherein the metal-organic matrix material comprises a coordination polymer; and a plurality of therapeutic agents, optionally wherein said plurality of therapeutic agents comprise: (i) at least two chemotherapeutic agents, such as at least two non-nucleic acid chemotherapeutic agents; (ii) at least two nucleic acid therapeutic agents, such as small interfering ribonucleic acids (siRNAs), microRNAs (miRNAs), antisense oligonucleotides (AS ODNs), or combinations thereof; (iii) at least one non-nucleic acid chemotherapeutic agent and at least one nucleic acid therapeutic agent; or (iv) at least one chemotherapeutic agent, such as at least one non-nucleic acid chemotherapeutic agent, and at least one photosensitizer.

In some embodiments, the plurality of therapeutic agents comprise at least one non-nucleic acid chemotherapeutic agent incorporated in the metal-organic matrix material core, optionally wherein the at least one non-nucleic acid chemotherapeutic agent is incorporated in the metal-organic matrix material core via a covalent or coordination bond. In some embodiments, the at least one non-nucleic acid chemotherapeutic agent is selected from the group comprising cisplatin or oxaliplatin prodrugs, gemcitabine, methotrexate, leucovorin, pemetrexed disodium, doxorubicin, vinblastine, vincristine, vindesine, cytarabine, azathioprine, melphalan, imatinib, anastrozole, letrozole, carboplatin, gemcitabine, paclitaxel, docetaxel, etoposide, and vinorelbine. In some embodiments, wherein the plurality of therapeutic agents comprise at least two chemotherapeutic agents incorporated in the metal-organic matrix material core.

In some embodiments, the plurality of therapeutic agents comprise at least one nucleic acid, optionally wherein the at least one nucleic acid is a siRNA, a miRNA, or an AS ODN. In some embodiments, the at least one nucleic acid is attached to the metal-organic matrix material core via coordination bonds between phosphate groups on the nucleic acid and metal ions on an outer surface of the core.

In some embodiments, the metal-organic matrix material core is a material comprising $Zr_6(\mu_3-O)_4(\mu_3-OH)_4$ and a dicarboxylate bridging ligand, optionally wherein the dicarboxylate bridging ligand comprises an amino substituent. In some embodiments, the dicarboxylate bridging ligand is amino-triphenyldicarboxylic acid. In some embodiments, at least one non-nucleic acid chemotherapeutic agent is covalently attached to a substituent on the dicarboxylate bridging unit.

In some embodiments, at least one nucleic acid therapeutic agent is attached via a coordination bond to a metal ion on an outer surface of the metal-organic matrix material core. In some embodiments, at least one non-nucleic acid chemotherapeutic agent is incorporated in pores in the metal-organic matrix material core via a covalent bond to the dicarboxylate bridging ligand and at least one nucleic acid is attached to an outer surface of the metal-organic matrix material core via a coordination bond with a metal ion on the outer surface of the metal-organic matrix material core.

In some embodiments, the at least one nucleic acid is selected from the group comprising survivin siRNA, ERCC-1 siRNA, P-glycoprotein siRNA (P-gp siRNA), Bcl-2 siRNA, or a mixture thereof. In some embodiments, the at least one non-nucleic acid chemotherapeutic agent is a cisplatin or oxaliplatin prodrug. In some embodiments, the non-nucleic acid chemotherapeutic agent is cis, cis, trans-$Pt(NH_3)_2Cl_2(OEt)(O_2CCH_2CH_2COOH)$, optionally wherein the core comprises between about 10 weight % and about 50 weight % of the non-nucleic acid chemotherapeutic agent. In some embodiments, the at least one nucleic acid is a mixture of survivin siRNA, ERCC-1 siRNA, and Bcl-2 siRNA.

In some embodiments, the nanoscale particle has an average diameter of between about 20 nm and about 140 nm.

In some embodiments, the nanoscale particle further comprises one or more coating agents or layers covering at least a portion of the outer surface of the metal-organic matrix material core, wherein the one or more coating agents or layers are selected from a metal oxide, a polymer, a single lipid layer, a lipid bilayer, and combinations thereof, and further wherein the at least one nucleic acid is covalently or non-covalently attached to a coating agent or layer. In some embodiments, the metal-organic matrix material core is coated with a lipid bilayer comprising a cationic lipid and/or a functionalized lipid, wherein said functionalized lipid is a lipid functionalized with a group that can bond to a nucleic acid, and wherein at least one nucleic acid is covalently bonded to the functionalized lipid and/or attached to the cationic lipid via electrostatic interactions.

In some embodiments, the lipid bilayer comprises a mixture comprising one or more of a thiol- or dithiol-functionalized 1,2-distearoyl-sn-glycero-3-phosphoethanolamine (DSPE), 1,2-dioleoyl-3-trimethylammonium propane (DOTAP), and 1,2-dioleoyl-sn-glycero-3-phosphocholine (DOPC). In some embodiments, the one or more coating agents or layers further comprises a passivating agent, such as a hydrophilic polymer; a targeting agent, such as an RGD peptide; and/or an imaging agent, such as a fluorescent moiety. In some embodiments, the lipid bilayer further comprises one or more of 1,2-dioleoyl-sn-glycero-3-phosphate sodium salt (DOPA), cholesterol, and pegylated-DSPE.

In some embodiments, the metal-organic matrix material core comprises a metal bisphosphonate coordination polymer comprising a multivalent metal ion and a bisphosphonate. In some embodiments, the multivalent metal ion is selected from the group comprising $Ca^{2+}$, $Mg^{2+}$, $Mn^{2+}$, $Zn^{2+}$, and combinations thereof.

In some embodiments, the bisphosphonate is a chemotherapeutic prodrug, such as a cisplatin or oxaliplatin prodrug. In some embodiments, the bisphosphonate is a bisphosphonate ester of cis, cis-trans-$[Pt(NH_3)_2Cl_2(OH)_2]$ (a cisplatin prodrug) or cis, trans-$[Pt(dach)Cl_2(OH)_2]$. In some embodiments, the metal ion is $Zn^{2+}$. In some embodiments, the metal-organic matrix material core comprises between about 40 and about 50 weight % of bisphosphonate. In some embodiments, the particle further comprises a lipid single layer or lipid bilayer coating, optionally wherein one or more of survivin siRNA, P-gp siRNA, and Bcl-2 siRNA are attached to the coating. In some embodiments, the nanoscale particle has a diameter between about 20 nm and about 180 nm.

In some embodiments, the presently disclosed subject matter provides a method of treating cancer in a subject in need thereof, the method comprising administering to the subject a composition comprising a nanoscale particle comprising a core comprising a metal-organic matrix material, optionally wherein the metal-organic matrix material comprises a coordination polymer; and a plurality of therapeutic agents, optionally wherein said plurality of therapeutic agents comprise: (i) at least two chemotherapeutic agents, such as at least two non-nucleic acid chemotherapeutic agents; (ii) at least two nucleic acid therapeutic agents, such as small interfering ribonucleic acids (siRNAs), microRNAs (miRNAs), antisense oligonucleotides (AS ODNs), or combinations thereof; (iii) at least one non-nucleic acid chemotherapeutic agent and at least one nucleic acid therapeutic agent; or (iv) at least one chemotherapeutic agent, such as at least one non-nucleic acid chemotherapeutic agent, and at least one photosensitizer. In some embodiments, the nanoscale particle comprises at least one non-nucleic acid chemotherapeutic agent and at least one nucleic acid.

In some embodiments, the core comprises: (i) a material comprising $Zr_6(\mu_3-O)_4(\mu_3-OH)_4$ and a dicarboxylate bridging ligand, optionally wherein the dicarboxylate bridging ligand comprises an amino substituent, or (ii) a metal bisphosphonate coordination polymer.

In some embodiments, the at least one non-nucleic acid chemotherapeutic agent is a cisplatin or oxaliplatin prodrug and the at least one nucleic acid is selected from survivin siRNA, ERCC-1 siRNA, P-gp siRNA, Bcl-2 siRNA, and combinations thereof. In some embodiments, the at least one nucleic acid is a mixture of survivin siRNA, ERCC-1 siRNA, P-gp siRNA, and Bcl-2 siRNA.

In some embodiments, the cancer is selected from lung cancer, pancreatic cancer, ovarian cancer, breast cancer and colon cancer. In some embodiments, the cancer is ovarian cancer, optionally a cisplatin resistant ovarian cancer.

In some embodiments, the presently disclosed subject matter provides a method of preparing a nanoscale particle of claim 1, the method comprising: (a) contacting a microemulsion comprising a metal ion with a microemulsion comprising a bisphosphonate, optionally wherein the bisphosphonate is a cisplatin or oxaliplatin prodrug, thereby forming a metal bisphosphonate coordination polymer nanoparticle; (b) dispersing the nanoparticle from (a) in a solution comprising a cationic lipid and/or a functionalized lipid to form a cationic lipid-coated and/or functionalized lipid coated nanoparticle; and (c) contacting the lipid-coated nanoparticles with a solution comprising at least one nucleic acid.

In some embodiments, the bisphosphonate microemulsion further comprises a lipid, optionally wherein the lipid is DOPA. In some embodiments, the at least one nucleic acid is selected from survivin siRNA, P-gp siRNA, Bcl-2 siRNA, and combinations thereof.

In some embodiments, the presently disclosed subject matter provides a method of preparing a nanoscale particle of claim 1, the method comprising: (a) contacting a solution of a Zr compound, optionally $ZrCl_4$, with a solution comprising a dicarboxylic acid, optionally amino-triphenyldicarboxylic acid, thereby forming a metal-organic matrix material nanoparticle core; (b) contacting the nanoparticle core with a solution comprising a non-nucleic acid chemotherapeutic agent, wherein said non-nucleic chemotherapeutic agent comprises a carboxylic acid substituent, and optionally wherein the solution comprising the non-nucleic acid chemotherapeutic agent further comprises a diimidazole, thereby forming a chemotherapeutic-functionalized metal-organic matrix material nanoparticle; and (c) contacting the chemotherapeutic-functionalized metal-organic matrix material with a solution comprising one or more nucleic acids.

In some embodiments, the at least one nucleic acid is selected from survivin siRNA, P-gp siRNA, Bcl-2 siRNA, and combinations thereof. In some embodiments, the non-nucleic acid chemotherapeutic agent is a cisplatin or oxaliplatin prodrug, optionally cis, cis, trans-$Pt(NH_3)_2Cl_2(OEt)(O_2CCH_2CH_2COOH)$.

In some embodiments, the presently disclosed subject matter provides a pharmaceutical formulation comprising a pharmaceutically acceptable carrier and a nanoscale particle comprising a core comprising a metal-organic matrix material, optionally wherein the metal-organic matrix material comprises a coordination polymer; and a plurality of therapeutic agents, optionally wherein said plurality of therapeutic agents comprise: (i) at least two chemotherapeutic agents, such as at least two non-nucleic acid chemotherapeutic agents; (ii) at least two nucleic acid therapeutic agents, such as small interfering ribonucleic acids (siRNAs), microRNAs (miRNAs), antisense oligonucleotides (AS ODNs), or combinations thereof; (iii) at least one non-nucleic acid chemotherapeutic agent and at least one nucleic acid therapeutic agent; or (iv) at least one chemotherapeutic agent, such as at least one non-nucleic acid chemotherapeutic agent, and at least one photosensitizer.

In some embodiments, the presently disclosed subject matter provides a nanoscale particle for co-delivery of a plurality of therapeutic agents, said nanoscale particle comprising: a core comprising a metal-organic matrix material, optionally wherein the metal-organic matrix material comprises a coordination polymer; and a plurality of therapeutic agents, wherein said plurality of therapeutic agents comprises at least one chemotherapeutic agent and at least one photosensitizer.

In some embodiments, the at least one chemotherapeutic agent is a non-nucleic acid chemotherapeutic agent incorporated in the metal-organic matrix material core, optionally wherein the non-nucleic acid chemotherapeutic agent is incorporated in the metal-organic matrix material core via a covalent or coordination bond. In some embodiments, the chemotherapeutic agent is selected from the group comprising cisplatin or oxaliplatin prodrugs, gemcitabine, methotrexate, leucovorin, pemetrexed disodium, doxorubicin, vinblastine, vincristine, vindesine, cytarabine, azathioprine, melphalan, imatinib, anastrozole, letrozole, carboplatin, gemcitabine, paclitaxel, docetaxel, etoposide, and vinorelbine.

In some embodiments, the chemotherapeutic agent is a bisphosphonate cisplatin or oxaliplatin prodrug and the metal-organic matrix material core comprises a metal bisphosphonate coordination polymer comprising a multivalent metal ion and said bisphosphonate cisplatin or oxaliplatin prodrug. In some embodiments, the multivalent metal ion is selected from the group comprising $Ca^{2+}$, $Mg^{2+}$, $Mn^{2+}$, $Zn^{2+}$, and combinations thereof. In some embodiments, the bisphosphonate cisplatin or oxaliplatin prodrug is a bisphosphonate ester of cis, cis-trans-$[Pt(NH_3)_2Cl_2(OH)_2]$ and/or the metal ion is $Zn^{2+}$.

In some embodiments, the nanoscale particle comprises one or more coating layers covering at least a portion of the outer surface of the metal-organic matrix material core, wherein the one or more coating agents or layers are selected from a metal oxide, a polymer, a single lipid layer, a lipid bilayer, and combinations thereof. In some embodiments, the photosensitizer is covalently attached to a coating layer or layers.

In some embodiments, the metal-organic matrix material core is coated with a lipid bilayer or lipid single layer comprising a pyrolipid, wherein said pyrolipid is a lipid covalently attached to a porphyrin or a derivative or analog thereof. In some embodiments, the lipid bilayer or lipid single layer further comprises one or more of cholesterol, 1,2-distearoyl-sn-glycero-3-phosphoethanolamine (DSPE), 1,2-Distearoyl-sn-glycero-3-phosphocholine (DSPC) 1,2-dioleoyl-3-trimethylammonium propane (DOTAP), 1,2-dioleoyl-sn-glycero-3-phosphocholine (DOPC), 1,2-dioleoyl-sn-glycero-3-phosphate sodium salt (DOPA), and pegylated-DSPE.

In some embodiments, the nanoscale particle has a diameter between about 90 nm and about 180 nm.

In some embodiments, the presently disclosed subject matter provides a pharmaceutical formulation comprising a pharmaceutically acceptable carrier and a nanoscale particle for co-delivery of a plurality of therapeutic agents, said nanoscale particle comprising: a core comprising a metal-organic matrix material, optionally wherein the metal-organic matrix material comprises a coordination polymer; and a plurality of therapeutic agents, wherein said plurality of therapeutic agents comprises at least one chemotherapeutic agent and at least one photosensitizer.

In some embodiments, the presently disclosed subject matter provides a method of treating cancer in a subject in need thereof, the method comprising administering to the subject a composition comprising a nanoscale particle for co-delivery of a plurality of therapeutic agents, said nanoscale particle comprising: a core comprising a metal-organic matrix material, optionally wherein the metal-organic matrix material comprises a coordination polymer; and a plurality of therapeutic agents, wherein said plurality of therapeutic agents comprises at least one chemotherapeutic agent and at least one photosensitizer; and irradiating the subject or a treatment area of the subject with radiation having a wavelength suitable to activate the photosensitizer.

In some embodiments, the at least one chemotherapeutic agent is a cisplatin or oxaliplatin prodrug. In some embodiments, the cancer is a head and neck cancer, optionally wherein the head and neck cancer is a cisplatin resistant head and neck cancer.

In some embodiments, the presently disclosed subject matter provides a method of preparing a nanoscale particle, wherein the method comprises: (a) contacting a microemulsion comprising a metal ion with a microemulsion comprising a bisphosphonate, optionally wherein the bisphosphonate is a cisplatin or oxaliplatin prodrug, thereby forming a metal bisphosphonate coordination polymer nanoparticle; and (b) dispersing the nanoparticle from (a) in a solution comprising a pyrolipid to form a pyrolipid-coated nanoparticle. In some embodiments, the solution comprising the pyrolipid further comprises one or more additional lipid coating components, optionally, wherein the solution comprising the pyrolipid further comprises cholesterol, 1,2-Distearoyl-sn-glycero-3-phosphocholine (DSPC), and pegylated 1,2-distearoyl-sn-glycero-3-phosphoethanolamine (DSPE).

Accordingly, it is an object of the presently disclosed subject matter to provide delivery agents for the co-delivery of a plurality of therapeutics (e.g., anticancer therapeutics), pharmaceutical compositions comprising the delivery agents, the use of the delivery agents, and methods of preparing the delivery agents.

An object of the presently disclosed subject matter having been stated hereinabove, and which is achieved in whole or in part by the presently disclosed subject matter, other objects will become evident as the description proceeds when taken in connection with the accompanying drawings and examples as best described hereinbelow.

CDDP ovarian cancer receiving i.p. injection of either phosphate buffered saline (PBS; control, unbroken line), a lipid bilayer covered nanoscale coordination polymer particle comprising a cisplatin prodrug (NCP-1, line with long dashes), or the same particle but also comprising small interfering RNA attached covalently to lipid in a lipid bilayer (NCP-1/thiol-siRNA, line with short dashes). The data is representative of three mice per group.

Figure 8:
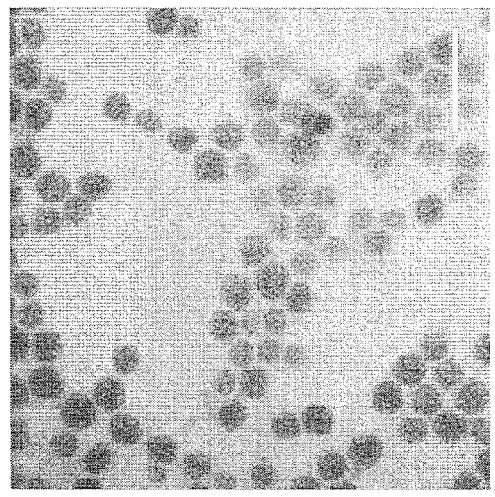
Figure 8:
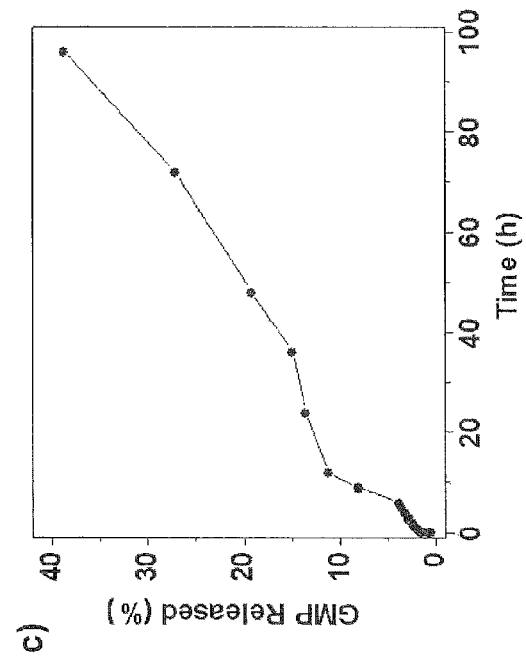
Figure 8:
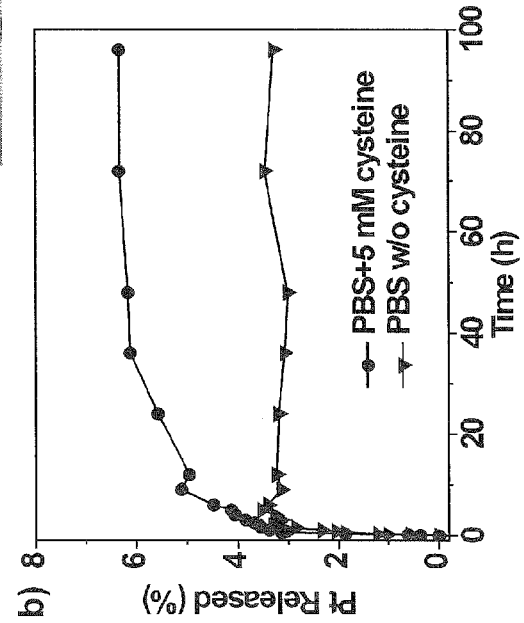

FIG. 8 shows (a) a TEM image of particle morphology, (bar=100 nm), (b) a graph showing cisplatin release, and (c) a graph showing gemcitabine release from nanoscale coordination polymer nanoparticles carrying cisplatin plus gemcitabine and siRNAs targeting Bcl-2 and survivin. The nanoparticles are spherical and monodispersed with a diameter of ~20 nm by TEM. Cisplatin release was promoted in the presence of the reducing agent cysteine. Gemcitabine (GMP) can be released from the nanoparticles.

Figure 9:
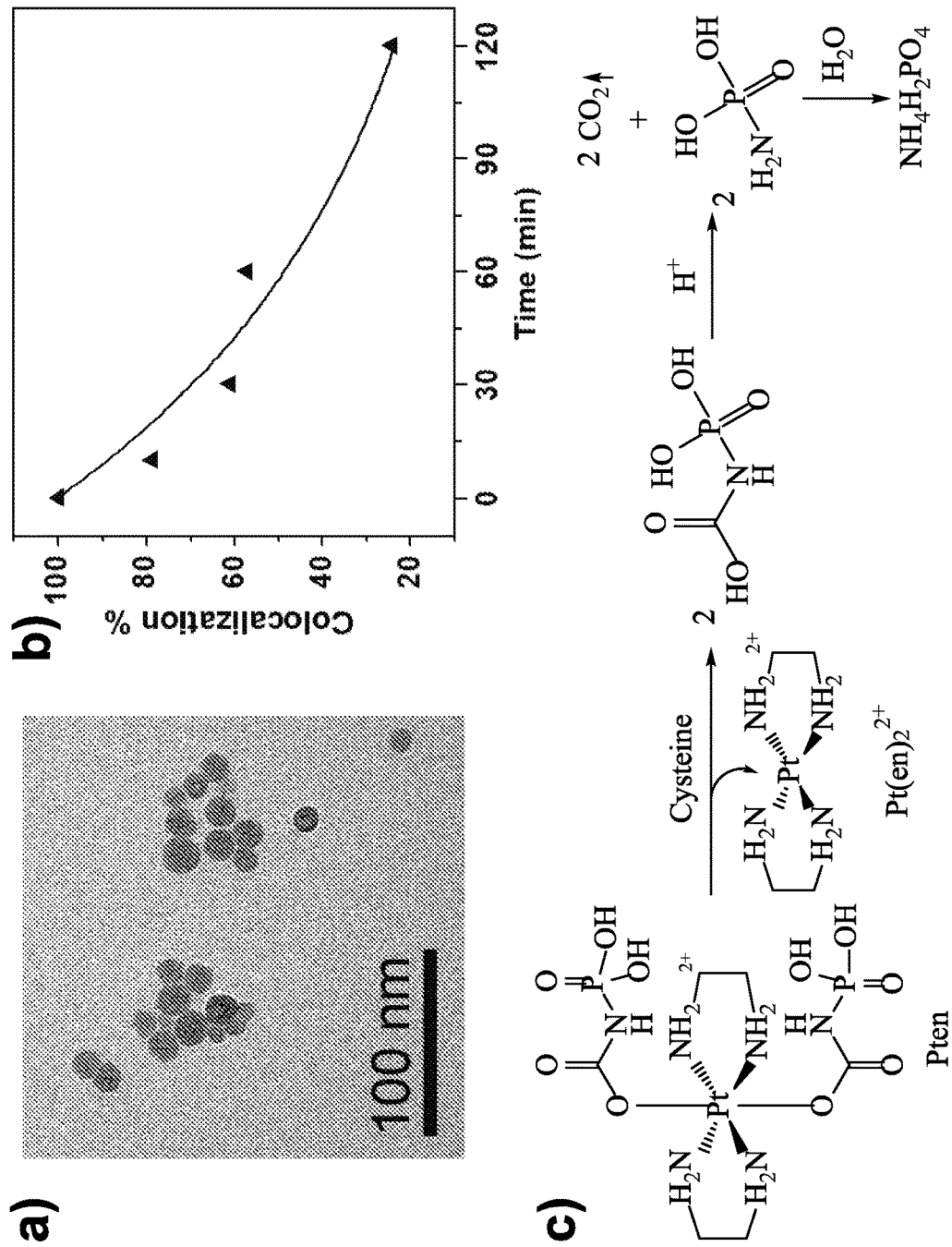

FIG. 9 shows (a) a TEM image of particle morphology, (b) a graph showing endosomal escape efficiency, and (c) a scheme showing the carbon dioxide generation mechanism of Pten-NCP nanoparticles carrying nontoxic Petn compound and thiol siRNA targeting survivin. Pten-NCP is spherical and mono-dispersed with a diameter of ~15 nm by TEM. After being incorporated into Pten-NCP, siRNA can efficiently escape from endosomal escape upon entering the cells. FIG. 9(b) shows the colocalization percent of fluorescence coming from siRNA and endosome observed by confocal laser scanning microscopy. When releasing one Pt(en)$_2$, Pten releases two carbon dioxide molecules intracellularly to facilitate efficient endosomal escape.

Figure 10:
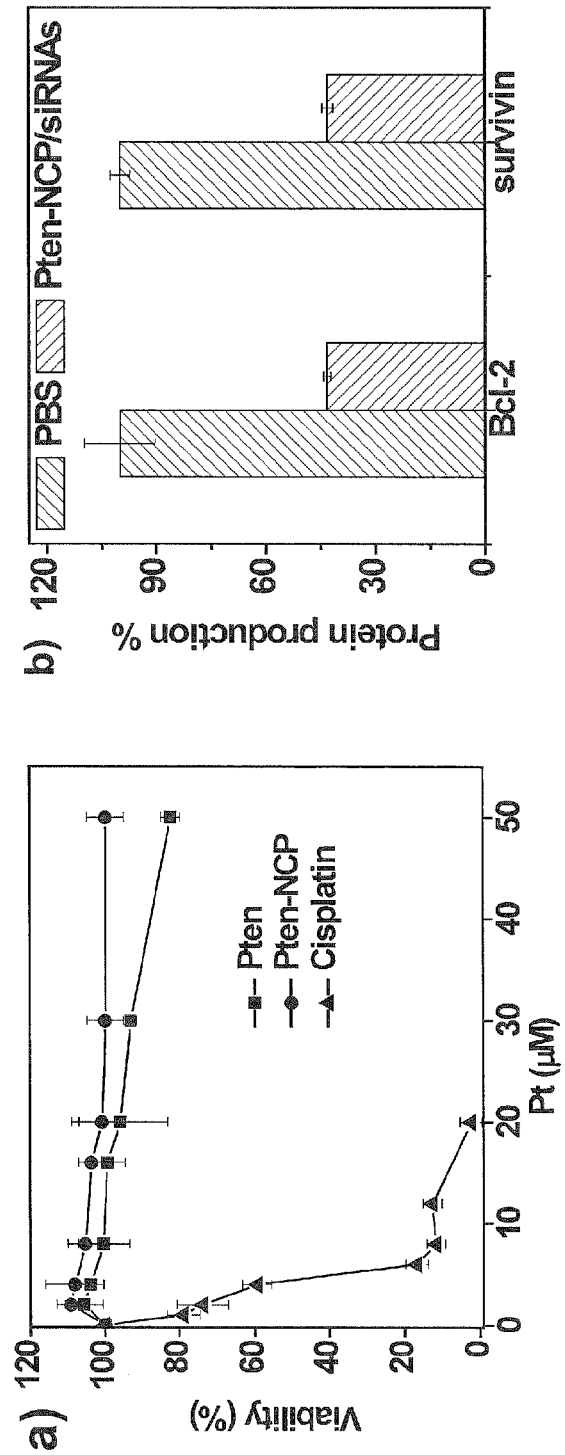

FIG. 10 is a set of graphs showing (a) the toxicity in H460 cells and (b) the gene silencing efficiency in human ovarian A2780/CDDP cells of Pten-NCP particles carrying nontoxic Pten and thiol siRNAs targeting Bcl-2 and survivin.

Figure 11:
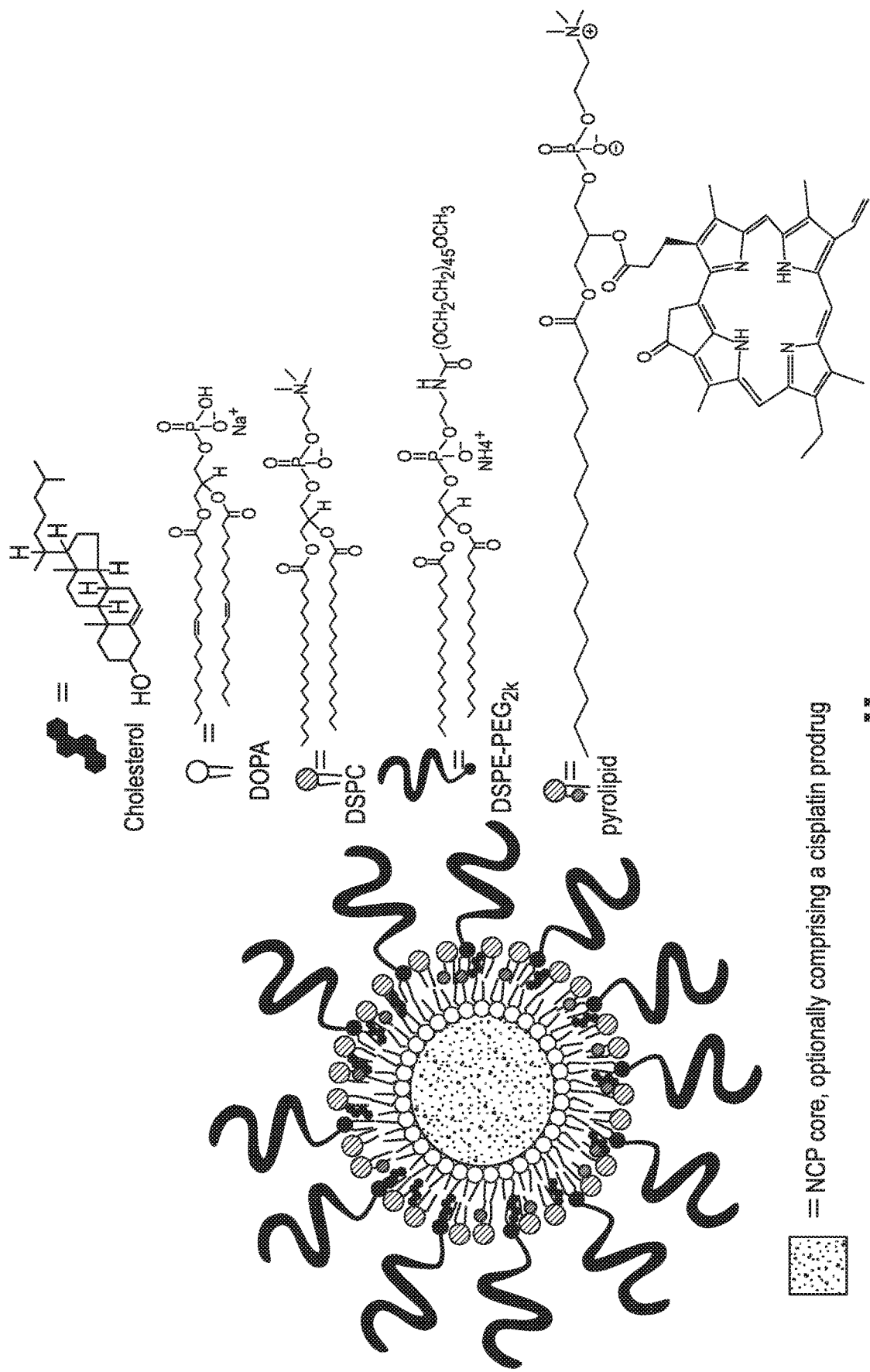

FIG. 11 is a schematic drawing showing a nanoparticle for the co-delivery of multiple therapeutic agents according to an embodiment of the presently disclosed subject matter. The multiple therapeutic agents include a photosensitizer moiety for photodynamic therapy covalently attached to a lipid in a coating layer surrounding a nanoscale coordination polymer (NCP) particle core. Additional therapeutic agents, such as small molecule chemotherapeutic agents, can be embedded in the NCP core.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a metal ion" includes a plurality of such metal ions, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. Nitrogen-containing heteroaryl moieties include, but are not limited to, pyridine, imidazole, benzimidazole, pyrazole, pyrazine, triazine, pyrimidine, and the like.

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "amino" refers to the group —$N(R)_2$ wherein each R is independently H, alkyl, substituted alkyl, aryl, substituted aryl, aralkyl, or substituted aralkyl. The terms "aminoalkyl" and "alkylamino" can refer to the group —$N(R)_2$ wherein each R is H, alkyl or substituted alkyl, and wherein at least one R is alkyl or substituted alkyl. "Arylamine" and "aminoaryl" refer to the group —$N(R)_2$ wherein each R is H, aryl, or substituted aryl, and wherein at least one R is aryl or substituted aryl, e.g., aniline (i.e., —$NHC_6H_5$).

The term "thioalkyl" can refer to the group —SR, wherein R is selected from H, alkyl, substituted alkyl, aralkyl, substituted aralkyl, aryl, and substituted aryl. Similarly, the terms "thioaralkyl" and "thioaryl" refer to —SR groups wherein R is aralkyl and aryl, respectively.

The terms "halo", "halide", or "halogen" as used herein refer to fluoro, chloro, bromo, and iodo groups.

The term "hydroxyl" refers to the —OH group.

The terms "mercapto" or "thiol" refer to the —SH group.

The terms "carboxylate" and "carboxylic acid" can refer to the groups —C(=O)O$^-$ and —C(=O)OH, respectively. In some embodiments, "carboxylate" can refer to either the —C(=O)O$^-$ or —C(=O)OH group.

The term "phosphonate" refers to the —P(=O)(OR)$_2$ group, wherein each R can be independently H, alkyl, aralkyl, aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "silyl" refers to groups comprising silicon atoms (Si).

The term "siloxane" refers to a compound comprising a —Si—O—Si— linkage. The term "poly(siloxane)" as used herein refers to a polymeric group or compound of the formula $R_2SiO$, wherein R is H, alkyl, aralkyl, or aryl.

The term "poly(silsesquioxane)" refers to a polymeric group or compound of the formula $RSiO_{1.5}$, wherein R is H, alkyl, aralkyl, or aryl.

The term "lipid" can refer to a hydrophobic or amphiphilic small molecule, such as, but not limited to a fatty acid, a phospholipid, a glycerolipid, a glycerophospholipid, a sphingolipid, a saccharolipid, or a polyketide.

The terms "nanoscale particle" "nanomaterial" and "nanoparticle" refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is between about 20 nm and about 250 nm (e.g., about 20, 30, 40, 50, 60, 70, 80, 90, 100, 110, 120, 130, 140, 150, 160, 170, 180, 190, 200, 210, 220, 230, 240, or 250 nm).

In some embodiments, the nanoparticle is approximately spherical. When the nanoparticle is approximately spherical, the characteristic dimension can correspond to the diameter of the sphere. In addition to spherical shapes, the nanomaterial can be disc-shaped, plate-shaped (e.g., hexagonally plate-like), oblong, polyhedral, rod-shaped, cubic, or irregularly-shaped.

The nanoparticle can comprise a core region (i.e., the space between the outer dimensions of the particle) and an outer surface (i.e., the surface that defines the outer dimensions of the particle). In some embodiments, the nanoparticle can have one or more coating layers surrounding or partially surrounding the nanoparticle core. Thus, for example, a spherical nanoparticle can have one or more concentric coating layers, each successive layer being dispersed over the outer surface of a smaller layer closer to the center of the particle. The presently disclosed nanoparticle can comprise a solid metal-organic framework matrix, which can comprise one or more pores or hollow interior regions. The matrix can be amorphous or crystalline. In some embodiments, the nanoparticle core further comprises one or more optical imaging agents and/or therapeutic agents (e.g., anticancer agents), which can be physically trapped within the matrix, coordinated to a metal ion of the matrix, or chemically bonded (e.g., to a bisphosphonate or other organic bridging ligand in the matrix) via a covalent or ionic bond. In some embodiments, a chemotherapeutic or prodrug thereof can be an organic bridging ligand within a metal-organic matrix material that forms the core of the nanoparticle. For example, when the matrix material is a metal bisphosphonate coordination polymer, the bisphosphonate can be a chemotherapeutic agent or prodrug thereof.

When the core comprises a non-matrix therapeutic and/or imaging agent, said agents can be said to be "embedded" in the nanoparticle. "Embedded" can refer to a therapeutic agent or an imaging agent that is bound, for example covalently bound or bound via a coordinative bond, inside the core of the particle (e.g., to a bisphosphonate, dicarboxylate, or metal ion of the matrix material). Alternatively, the complex or agent can be "sequestered" (i.e., non-covalently encapsulated) inside pores in the core or interact with a core material via hydrogen bonding, London dispersion forces, or any other non-covalent interaction.

The terms "polymer" and "polymeric" refer to chemical structures that have repeating units (i.e., multiple copies of a given chemical substructure). Polymers can be formed from polymerizable monomers. A polymerizable monomer is a molecule that comprises one or more moieties that can react to form bonds (e.g., covalent or coordination bonds) with moieties on other molecules of polymerizable monomer. Generally, each polymerizable monomer molecule can bond to two or more other molecules. In some cases, a polymerizable monomer will bond to only one other molecule, forming a terminus of the polymeric material.

Polymers can be organic, or inorganic, or a combination thereof. As used herein, the term "inorganic" refers to a compound or composition that contains at least some atoms other than carbon, hydrogen, nitrogen, oxygen, sulfur, phosphorous, or one of the halides. Thus, for example, an inorganic compound or composition can contain one or more silicon atoms and/or one or more metal atoms.

As used herein "organic polymers" are those that do not include silica or metal atoms in their repeating units. Exemplary organic polymers include polyvinylpyrrolidone (PVO), polyesters, polyamides, polyethers, polydienes, and the like. Some organic polymers contain biodegradable linkages, such as esters or amides, such that they can degrade overtime under biological conditions.

The term "hydrophilic polymer" as used herein generally refers to hydrophilic organic polymers, such as but not limited to, polyvinylpyrrolidone, polyvinylmethylether, polymethyloxazoline, polyethyloxazoline, polyhydroxypropyloxazoline, polyhydroxypropylmethacrylamide, polymethyacrylamide, polydimethylacrylamide, polyhydroxylpropylmethacrylate, polyhydroxyethylacrylate, hydroxymethylcellulose, hydroxyethylcellulose, polyethylenimine (PEI), polyethyleneglycol (i.e., PEG) or another hydrophilic poly(alkyleneoxide), polyglycerine, and polyaspartamide. The term "hydrophilic" refers to the ability of a molecule or chemical species to interact with water. Thus, hydrophilic polymers are typically polar or have groups that can hydrogen bond to water.

The term "imaging agent" refers to a chemical moiety that aids in the visualization of a sample. For example, an imaging agent can be a "contrast agent", and can refer to a moiety (a specific part of or an entire molecule, macromolecule, coordination complex, or nanoparticle) that increases the contrast of a biological tissue or structure being examined. The contrast agent can increase the contrast of a structure being examined using, for example, magnetic resonance imaging (MRI), optical imaging, positron emission tomography (PET) imaging, single photon emission computed tomography (SPECT) imaging, or a combination thereof (i.e., the contrast agent can be multimodal).

The term "MRI contrast agent" refers to a moiety that effects a change in induced relaxation rates of water protons in a sample.

The terms "optical imaging agent" or "optical contrast agent" refer to a group that can be detected based upon an ability to absorb, reflect or emit light (e.g., ultraviolet, visible, or infrared light). Optical imaging agents can be detected based on a change in amount of absorbance, reflectance, or fluorescence, or a change in the number of absorbance peaks or their wavelength maxima. Thus, optical imaging agents include those which can be detected based on fluorescence or luminescence, including organic and inorganic dyes.

The terms "fluorophore" and "fluorescent moiety" refer to species that can be excited by visible light or non-visible light (e.g., UV light). Examples of fluorophores include, but are not limited to: quantum dots and doped quantum dots (e.g., a semiconducting CdSe quantum dot or a Mn-doped CdSe quantum dot), fluorescein, fluorescein derivatives and analogues, indocyanine green, rhodamine, triphenylmethines, polymethines, cyanines, phalocyanines, naphthocyanines, merocyanines, lanthanide complexes or cryptates, fullerenes, oxatellurazoles, LaJolla blue, porphyrins and porphyrin analogues and natural chromophores/fluorophores such as chlorophyll, carotenoids, flavonoids, bilins, phytochrome, phycobilins, phycoerythrin, phycocyanines, retinoic acid and analogues such as retinoins and retinates.

The term "photosensitizer" (PS) refers to a chemical compound or moiety that can be excited by light of a particular wavelength, typically visible or near-infrared light, and produce a reactive oxygen species (ROS). For example, in its excited state, the photosensitizer can undergo intersystem crossing and transfer energy to oxygen ($O_2$) (e.g., in tissues being treated by PDT) to produce ROSs, such as singlet oxygen. Any known type of a photosensitizer can be used in accordance with the presently disclosed subject matter. In some embodiments, the photosensitizer is a porphyrin, a chlorophyll, a dye, or a derivative or analog thereof. In some embodiments, phophyrins, chlorins, bacteriochlorins, or porphycenes can be used. In some embodiments, the photosensitizer can have a functional group, such as carboxylic acid, amine, or isothiocyanate, e.g., for using in attaching the photosensitizer to another molecule, such as a lipid. In some embodiments, the photosensitizer is a porphyrin or a derivative or analog thereof. Exemplary porphyrins include, but are not limited to, hematoporphyrin, protoporphyrin and tetraphenylporphyrin. Exemplary porphyrin derivatives include, but are not limited to, pyropheophorbides, bacteriochlorophylls, chlorophyll a, benzoporphyrin derivatives, tetrahydroxyphenyl chlorins, purpurins, benzochlorins, naphthochlorins, verdins, rhodins, oxochlorins, azachlorins, bacteriochlorins, tolyporphyrins and benzobacteriochlorins. Porphyrin analogs include, but are not limited to, expanded porphyrin family members (such as texaphyrins, sapphyrins and hexaphyrins), and porphyrin isomers (such as porphycenes, inverted porphyrins, phthalocyanines, and naphthalocyanines).

The term "pyrolipid" refers to a conjugate of a lipid and a porphyrin, porphyrin derivative, or porphyrin analog. In some embodiments, the pyrolipid can comprise a lipid conjugate wherein a porphyrin or a derivative or analog thereof is covalently attached to a lipid side chain. Pyrolipids and pyrolipid synthesis are described, for example, in U.S. Patent Application Publication No. 2014/0127763, which is incorporated herein by reference in its entirety.

The terms "bonding" or "bonded" and variations thereof can refer to either covalent or non-covalent bonding. In some cases, the term "bonding" refers to bonding via a coordinate bond. The term "conjugation" can refer to a bonding process, as well, such as the formation of a covalent linkage or a coordinate bond.

A "coordination complex" is a compound in which there is a coordinate bond between a metal ion and an electron pair donor, ligand or chelating group. Thus, ligands or chelating groups are generally electron pair donors, molecules or molecular ions having unshared electron pairs available for donation to a metal ion.

The term "coordinate bond" refers to an interaction between an electron pair donor and a coordination site on a metal ion resulting in an attractive force between the electron pair donor and the metal ion. The use of this term is not intended to be limiting, in so much as certain coordinate bonds also can be classified as have more or less covalent character (if not entirely covalent character) depending on the characteristics of the metal ion and the electron pair donor.

As used herein, the term "ligand" refers generally to a species, such as a molecule or ion, which interacts, e.g., binds, in some way with another species. More particularly, as used herein, a "ligand" can refer to a molecule or ion that binds a metal ion in solution to form a "coordination complex." See Martell, A. E., and Hancock, R. D., *Metal Complexes in Aqueous Solutions*, Plenum: New York (1996), which is incorporated herein by reference in its entirety. The terms "ligand" and "chelating group" can be used interchangeably. The term "bridging ligand" can refer to a group that bonds to more than one metal ion or complex, thus providing a "bridge" between the metal ions or complexes. Organic bridging ligands can have two or more groups with unshared electron pairs separated by, for example, an alkylene or arylene group. Groups with unshared electron pairs, include, but are not limited to, $-CO_2H$, $-NO_2$, amino, hydroxyl, thio, thioalkyl, $-B(OH)_2$, $-SO_3H$, $PO_3H$, phosphonate, and heteroatoms (e.g., nitrogen, oxygen, or sulfur) in heterocycles.

As used herein, the term "metal-organic matrix material" refers to a solid material comprising both metal and organic components, wherein the organic components include at least one, and typically more than one carbon atom. In some embodiments, the matrix material is porous. In some embodiments, the metal-organic matrix material is a coordination polymer, which comprises repeating units of coordination complexes comprising metal ions and bridging polydentate (e.g., bidentate) organic ligands. In some embodiments, the matrix material contains more than one type of metal ion. In some embodiments, the matrix material can contain metal clusters. In some embodiments, the matrix material is a metal-organic framework comprising a coordination complex network that comprises bridging organic ligands.

The term "cancer" as used herein refers to diseases caused by uncontrolled cell division and the ability of cells to metastasize, or to establish new growth in additional sites. The terms "malignant", "malignancy", "neoplasm", "tumor," "cancer" and variations thereof refer to cancerous cells or groups of cancerous cells.

Particular types of cancer include, but are not limited to, skin cancers (e.g., melanoma), connective tissue cancers (e.g., sarcomas), adipose cancers, breast cancers, head and neck cancers, lung cancers (e.g., mesothelioma), stomach cancers, pancreatic cancers, ovarian cancers, cervical cancers, uterine cancers, anogenital cancers (e.g., testicular cancer), kidney cancers, bladder cancers, colon cancers, prostate cancers, central nervous system (CNS) cancers, retinal cancer, blood, neuroblastomas, multiple myeloma, and lymphoid cancers (e.g., Hodgkin's and non-Hodgkin's lymphomas).

The terms "anticancer drug", "chemotherapeutic", and "anticancer prodrug" refer to drugs (i.e., chemical compounds) or prodrugs known to, or suspected of being able to treat a cancer (i.e., to kill cancer cells, prohibit proliferation of cancer cells, or treat a symptom related to cancer). In some embodiments, the term "chemotherapeutic" as used herein refers to a non-nucleic acid or non-PS molecule that is used to treat cancer and/or that has cytotoxic ability. Such more traditional or conventional chemotherapeutic agents can be described by mechanism of action or by chemical compound class, and can include, but are not limited to, alkylating agents (e.g., melphalan), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib), nucleotide analogs or precursors thereof (e.g., methotrexate), peptide antibiotics (e.g., bleomycin), platinum based agents (e.g., cisplatin or oxaliplatin), retinoids (e.g., tretinoin), and vinka alkaloids (e.g., vinblastine).

II. Nanoscale Coordination Polymer Particles for Co-Delivery of Chemotherapeutics and Nucleic Acids RNA interference (RNAi) is a post-transcriptional mechanism of gene silencing through chromatin remodeling, inhibition of protein translation or direct mRNA degradation, which holds great promise in the field of cancer therapy. RNAi regulates the expression of key genes that determine cell fate and differentiation, which could be achieved by introducing foreign double-stranded RNAs (dsRNA) to initiate a potent cascade of sequence-specific degradation of endogenous mRNAs that bear homology to the dsRNA trigger. These RNA duplexes are referred to as small interfering (siRNAs). Understanding of the molecular pathways important for carcinogenesis has created opportunities for cancer therapy employing RNAi technology to target the key molecules within these pathways. RNAi targeting resistance to chemo- or radiotherapy has also been investigated. The silencing of critical genes by RNAi technology has generated antiproliferative and/or proapoptotic effects in cell-culture systems or in preclinical animal models.

One of the advantages of RNAi technology is that it can be used to target a large number of different genes involving various distinct cellular pathways. This is particularly important for a disease as complex as cancer. Major cellular pathways altered in cancer include: (1) oncogenesis pathways: the receptor protein tyrosine kinase (PTK) pathway (e.g., EGFR/ErbB1, ErbB2/HER2/Neu, IGF-1R, K-ras, R-ras, BRAF, ABL, and c-Src), adenomatous polyposis coli (APC) pathway (e.g., Met and c-Myc), glioma-associated oncogene (GLI) pathway (e.g., N-Myc and Cyclin-D1), phosphoinositide 3-kinase (PIK3) pathway (e.g., PI3K, AKT, and NF-κβ), SMAD pathway (e.g., EWS/FLI-1), hypoxia-inducible transcription factor (HIF) pathway; (2) cell cycle regulators: retinoblastoma (Rb) pathway (e.g., HPV E7, and E2F4), p53 pathway (e.g., HPV E6, Hdmx, Notch-1, and Delta-like-1); and (3) apoptosis (APOP) pathway (e.g., FLIP, BCL-2, BCL-XL, Survivin, and XIAP). Most of the RNAi candidate cancer gene targets are involved in pathways that are relevant to tumor growth. RNAi can also be used to target and silence genes that negatively regulate the function of endogenous tumor suppressor genes, such as genes involved in cellular senescence (e.g., telomerase and ID1) and protein stability and degradation (e.g., Cks-1, Skp-2, and cathepsin L).

Neoplastic cells grow within the context of the host environment, and must respond to numerous physical, chemical and cellular challenges. Therefore, those cells develop multiple strategies to control the tumor-host interaction. In order for a neoplasm to grow and spread, it needs to obtain sufficient oxygen and nutrients to break down the extracellular matrix (ECM) in order to invade surrounding tissues and metastasize, and to evade the host immune response. RNAi technology can be used to target the molecules involved in angiogenesis, invasion/metastasis, and immune evasion for cancer therapy. These target genes include: (1) growth factors (e.g., VEGF, EGF, FGF, PDGF, IL-8, and IGF-1); (2) proteases and protease inhibitors (e.g., Cathepsin, MMP2, Stromelysin, and uPA); (3) oncogenes (e.g., c-myc, ras, c-src, v-raf, c-jun, and VEGFR); (4) signal transduction (e.g., thymidine and phosporylase); (5) enzymes (e.g., RAS-farnesyl, transferase, Geranyl, and Transferase); (6) cytokines (e.g., IL-1, IL-6, and IL-8); and (7) endogenous stimulator (e.g., Ang-1, Angiostatin II, Endothelin, iNOS, PAF, and Cox-2).

The expression of antiapoptotic proteins by cancer cells is an important mechanism by which cancer cells develop resistance to chemotherapy or irradiation. Using RNAi to target antiapoptotic proteins represents a promising strategy to be used in conjunction with chemotherapy and radiotherapy for cancer treatment. There are also several additional mechanisms that contribute to the chemoresistance or radioresistance, and molecules related to these mechanisms can provide opportunities for RNAi intervention. For example, RNAi targeting multidrug resistance (MDR) genes (e.g., ABCB1, ABCB4, and ABCB5) can be an approach for the treatment of MDR gene-mediated drug resistance. DNA repair mechanisms are crucial for the maintenance of genomic stability and thus are potential therapeutic targets for cancer. In the stress of chemo- or radiotherapy, cancer cells will overexpress proteins related to DNA repair in order to restore therapy-induced DNA damage. These target genes include excision repair cross-complementing 1 (ERCC1), X-ray repair cross-complementing protein 1 (XRCC1), ribonucleotide reductase, double-strand break signaling/repair proteins ATM, and DNA-dependent protein kinase catalytic subunit.

MicroRNAs (miRNAs) are a class of small, non-coding RNAs that post-transcriptionally control the translation and stability of mRNAs. miRNAs are responsible for maintaining a proper balance of various biological processes, including proliferation, differentiation, and cell death. In cancer, the loss of tumor-suppressive miRNAs enhances the expression of target oncogenes, whereas increased expression of oncogenic miRNAs can repress target tumor suppressor genes. Cancer-related miRNAs have been classified as oncogenic (such as miR-155, miR-21, and miR-17-29), tumor-suppressive (such as miR-15, miR-16, LIN28, DICER), and context-dependent (such as miR-146 and miR-29) genes. Delivering tumor-suppressive miRNAs and silencing oncogenic miRNAs have been successful in various mouse models.

Owing to the ability of miRNAs to target signaling pathways that are often perturbed in cancer, miRNAs also have the potential to sensitize resistant cells. MDR usually involves the increased excretion of a drug through ATP-binding cassette (ABC) transporters. Two of these ABC transporters, ABCC3 and ABCC6, are induced directly by SOX2. miR-9 is identified as a negative regulator of SOX2. Forced expression of miR-9 in a chemotherapy-resistant glioma stem cell lines suppresses SOX2 expression, leading to reduced ABC transporter expression and hence drug retention.

Oligonucleotides are unmodified or chemically modified single-stranded DNA molecules. In general, they are relatively short (13-25 nucleotides) and hybridize to a unique sequence in the total pool of targets present in cells. Antisense oligonucleotides (AS ODNs) are single-stranded DNA fragments found to be able to inhibit mRNA translation. Antitumor AS ODNs are targeted to the genes that are involved in cell division, angiogenesis, metastasis, and cell survival in the presence of apoptotic signals including Bcl-2, Survivin, MDM2, Bcl-XL, RelA, RAS, RAF, BCR-ABL, JNK1,2, TERT, c-myc, and c-myb. Since the majority of cancer cells differ in gene expression profile from normal cells, AS ODNs can be used to specifically suppress the tumor growth with minimal consequences for normal cells. For example, Genta Inc. (Berkeley Heights, N.J., United States of America) has developed an 18-mer phosphothioate AS ODN that is complementary to Bcl-2, known as Genasense™. In addition, AS ODNs targeting MDM2 have been shown to potentiate the effects of growth inhibition, p53 activation and p21 induction by several chemotherapeutic agents.

Nanoparticle coordination polymers (NCPs) are an emerging class of self-assembled, hybrid nanomaterials whose properties can be tuned by varying the molecular building blocks. According to some embodiments of the presently disclosed subject matter, NCPs can be engineered to contain both chemotherapeutics and nucleic acid drugs including siRNAs, microRNAs, and antisense oligonucleotides (DNA). In certain embodiments, the NCPs contain only nucleic acid drugs, such as siRNAs. The simultaneous and efficient delivery of multiple chemotherapeutics (such as cisplatin, oxaliplatin, pemetrexed, gemcitabine, paclitaxel, doxorubicin) or a combination of several of these chemotherapeutics and RNAs to cancer cells can allow for enhanced anticancer efficacy by exerting antiproliferative and/or proapoptotic effects, for example, by blocking multiple cell signaling pathways. In certain embodiments, derivatives or analogues of these drugs can be used. For example, gemcitabine analogues such as those described in U.S. Pat. Nos. 6,384,019, 7,803,785, and 7,704,972, U.S. patent application Ser. Nos. 13/121,660, 11/908,364, and 14/347,504 and International Patent Application PCT/2013/068965 can be used. NCPs can also enhance the delivery of small molecule drugs and biologics to tumor sites via the enhanced permeability and retention (EPR) effect by taking advantage of the leaky blood vasculatures and reduced lymphatic drainage in tumors.

Thus, in accordance with some embodiments of the presently disclosed subject matter, conventional chemotherapeutics and nucleic acids can be combined in a nanocarrier platform, e.g., in order to elicit synergistic effects in cancer therapy. In addition, the particles containing chemotherapeutics and nucleic acids can be combined, for example, with X-ray radiotherapy to enhance the efficacy of chemoradiotherapy.

Accordingly, in some embodiments, the presently disclosed subject matter provides a nanoparticle comprising a metal-organic matrix material, such as a nanoscale coordination polymer, MOF and/or NMOF, for the co-delivery of multiple therapeutic agents, such as, but not limited to, the co-delivery of conventional chemotherapeutics and nucleic acids (e.g., siRNAs, miRNAs, AS ODNs, etc.). In some embodiments, the presently disclosed subject matter provides a nanoscale particle platform for the co-delivery of multiple conventional chemotherapeutic agents and for treating cancer using the nanoscale particles.

Thus, in some embodiments, multiple chemotherapeutics (i.e., a plurality of the same chemotherapeutic or a plurality of different chemotherapeutics) can be loaded in a NCP. The multiple chemotherapeutics can be incorporated in the core of NCPs through coordination bonds, covalent bonds, electrostatic interactions, etc., for the treatment of various cancers. For instance, in some embodiments for the treatment of lung cancer, the combination of cisplatin and carboplatin plus gemcitabine, paclitaxel, docetaxel, pemetrexed, etoposide, and vinorelbine can be used. In some embodiments for the treatment of pancreatic cancer, the combination of oxaliplatin plus gemcitabine can be used. In some embodiments, for the treatment of ovarian cancer, the combination of cisplatin/carboplatin plus taxane (paclitaxel/docetaxel) and cisplatin/carboplatin plus gemcitabine can be used. In some embodiments, for the treatment of colon cancer, the combination of oxaliplatin plus 5-FU/leucovorin can be used.

In some embodiments, the presently disclosed NCP particles can be used as a delivery platform for multiple nucleic acids (such as siRNAs and miRNAs). The particles can comprise, for example, a single siRNA or pooled siRNAs (including several siRNAs targeting different anticancer pathways). These siRNAs can include, but are not limited to, the following: EGFR/ErbB1 siRNA, ErbB2/HER2/Neu siRNA, IGF-1R siRNA, K-ras siRNA, R-ras siRNA, BRAF siRNA, ABL siRNA, c-Src siRNA, Met siRNA, c-Myc siRNA, N-Myc siRNA, Cyclin-D1 siRNA, PI3K siRNA, AKT siRNA, NF-κβ siRNA, EWS/FLI-1 siRNA, HIF siRNA, HPV E7 siRNA, E2F4 siRNA, HPV E6 siRNA, Hdmx siRNA, Notch-1 siRNA, Delta-like-1 siRNA, FLIP siRNA, BCL-2 siRNA, BCL-XL siRNA, Survivin siRNA, XIAP siRNA, Telomerase siRNA, ID1 siRNA, Cks-1 siRNA, Skp-2 siRNA, cathepsin L siRNA, VEGF siRNA, EGF siRNA, FGF siRNA, PDGF siRNA, IL-8 siRNA, IGF-1 siRNA, Cathepsin siRNA, MMP2 siRNA, Stromelysin siRNA, uPA siRNA, c-myc siRNA, ras siRNA, c-src siRNA, v-raf siRNA, c-jun siRNA, VEGFR siRNA, Thymidine siRNA, phosporylase siRNA, RAS-farnesyl siRNA, transferase siRNA, Geranyl siRNA, Transferase siRNA, IL-1 siRNA, IL-6 siRNA, IL-8. siRNA, Ang-1 siRNA, Angiostatin II siRNA, Endothelin siRNA, iNOS siRNA, PAF siRNA, Cox-2 siRNA, ABCB1 siRNA, ABCB4 siRNA, ABCB5 siRNA, P-glycoprotein siRNA, ERCC1 siRNA, and ATM siRNA. The miRNAs can include, but are not limited to, the following: miR-9, miR-15, miR-16, miR-34, miR-181, miR-200, miR 200c, miR-342, miR-630, let-7, LIN28, and DICER. The particles can also include one or more antisense oligonucleotides (AS ODNs). Gene targets of the AS ODNs used can include, but are not limited to, the following: Bcl-2, Survivin, MDM2, Bcl-XL, RelA, RAS, RAF, BCR-ABL, JNK1,2, TERT, c-myc, and c-myb. In some embodiments, one nucleic acid is used. In other embodiments, a combination of, for example, 2, 3, 4, 5, 6, 7, 8, 9, 10 or more different nucleic acids is used.

In some embodiments, the particles can be used for the co-delivery of siRNAs and conventional chemotherapeutics. In some embodiments, the particles can be used for the co-delivery of miRNAs and conventional chemotherapeutics. In some embodiments, the particles can be used for the co-delivery of AS ODNs and conventional chemotherapeutics. The particles can be used in conventional chemotherapy settings and/or in conventional chemoradiotherapy settings. In some embodiments, only nucleic acids are delivered.

Figure 1:
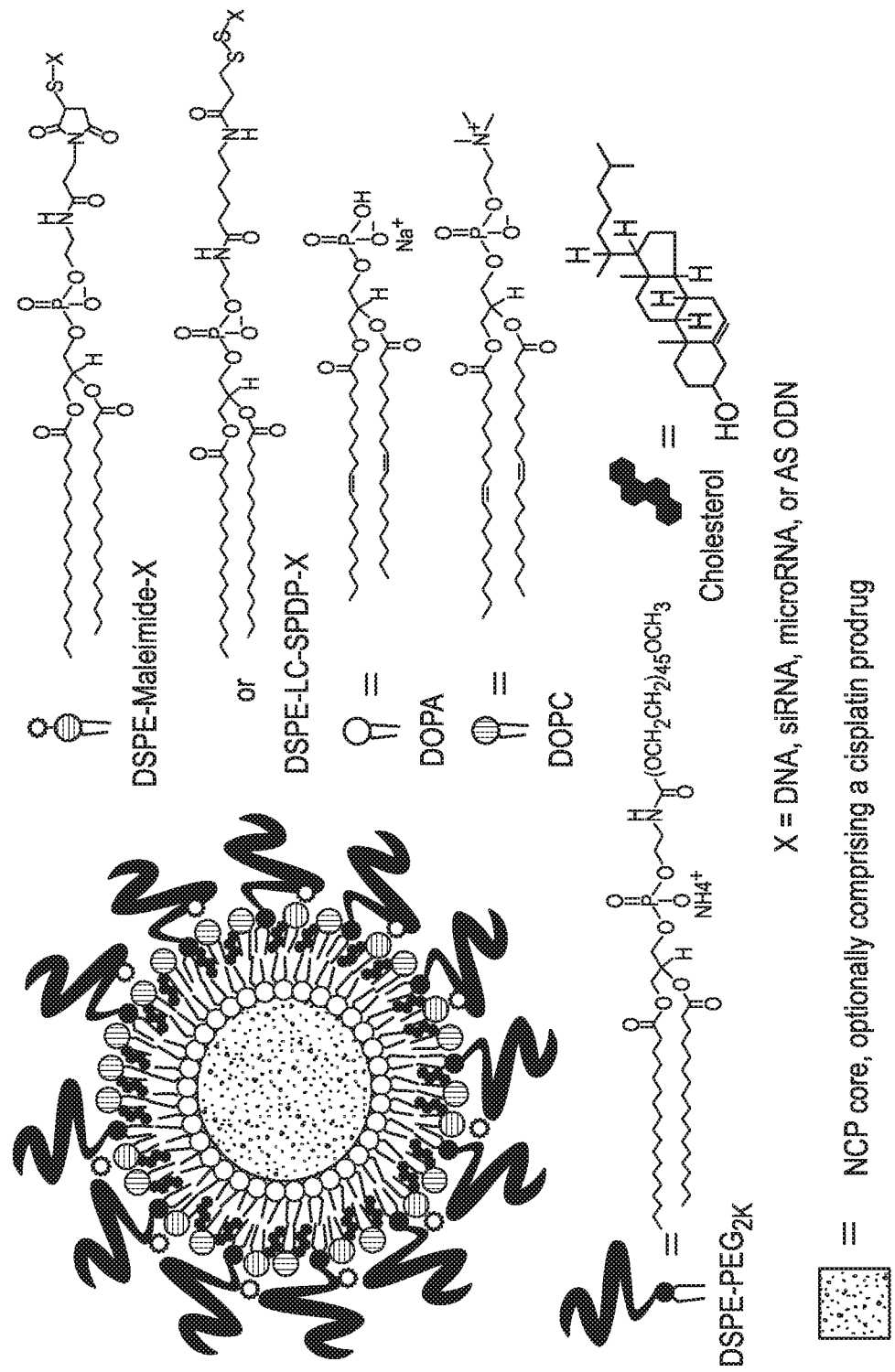
FIG. 1 is a schematic drawing showing a nanoparticle for the co-delivery of multiple therapeutic agents according to an embodiment of the presently disclosed subject matter. The multiple therapeutic agents include at least one therapeutic nucleic acid (e.g., a DNA, small interfering RNA (siRNA), microRNA or antisense oligonucleotide (AS ODN)) covalently attached to a lipid in a lipid bilayer coating surrounding a nanoscale coordination polymer (NCP) nanoparticle core. Additional therapeutic agents, such as small molecule chemotherapeutic agents, can be embedded in the NCP core.
Figure 2:
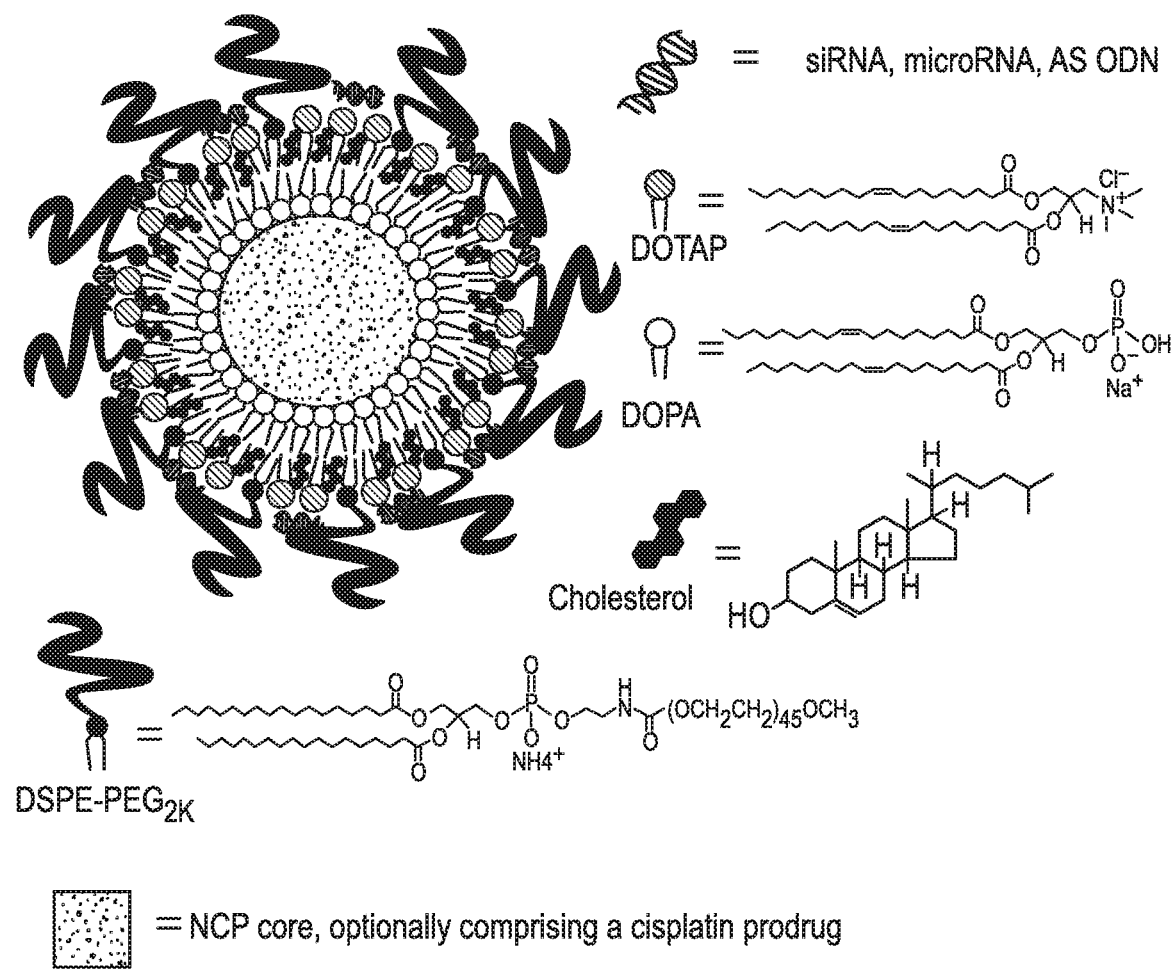
FIG. 2 is a schematic drawing showing a nanoparticle for the co-delivery of multiple therapeutic agents according to an embodiment of the presently disclosed subject matter. The multiple therapeutic agents include at least one therapeutic nucleic acid (e.g., a DNA, small interfering RNA (siRNA) microRNA, or antisense oligonucleotide (AS ODN)) non-covalently attached to charged groups in a lipid in a coating layer surrounding a nanoscale coordination polymer (NCP) nanoparticle core. Additional therapeutic agents, such as small molecule chemotherapeutic agents, can be embedded in the NCP core.

Exemplary embodiments for co-delivery of chemotherapeutics and nucleic acids are shown in FIGS. 1 and 2. According to these embodiments AS ODNs (DNA), siRNA, and/or microRNA can be covalently attached to lipid molecules (FIG. 1) and/or attached to lipid molecules through electrostatic interactions (FIG. 2), wherein said lipid molecules form part of a lipid bilayer coating surrounding a nanoparticle core (e.g., a chemotherapeutic-loaded NCP core). The lipid molecules can also be attached to passivating agents (i.e., agents which can deter the adsorption of plasma proteins to the nanoparticles and/or decrease recognition of the nanoparticles by the body's defense systems such as the reticulo-endothelial system (RES)), targeting moieties, and imaging agents. In addition, nucleic acids such as siRNAs, miRNAs, and AS ODNs, can be directly loaded to the surfaces of NCPs via coordination bonds between metal ions on the NCP outer surface and phosphate groups on nucleic acids.

In some embodiments, the presently disclosed subject matter provides a nanoscale particle for co-delivery of a plurality of therapeutic agents. In some embodiments, the nanoscale particle comprises: a core comprising a metal-organic matrix material, optionally wherein the metal-organic matrix material comprises a coordination polymer; and a plurality of therapeutic agents. In some embodiments, the plurality of therapeutic agents comprise: (i) at least two chemotherapeutic agents (i.e., two different chemotherapeutic agents), such as at least two non-nucleic acid or conventional chemotherapeutic agents; (ii) at least two nucleic acid therapeutic agents, such as small interfering ribonucleic acids (siRNAs), microRNAs (miRNAs), antisense oligonucleotides (AS ODNs), or combinations thereof; (iii) at least one non-nucleic acid chemotherapeutic agent and at least one nucleic acid therapeutic agent; (iv) at least one chemotherapeutic agent (e.g., one conventional/non-nucleic acid chemotherapeutic agent) and at least one photosensitizer, or (v) at least one chemotherapeutic agent, at least one nucleic acid, and at least one photosensitizer.

In some embodiments, the plurality of therapeutic agents comprise at least one non-nucleic acid chemotherapeutic agent incorporated in the metal-organic matrix material core. For example, the at least one non-nucleic acid chemotherapeutic agent can be incorporated in the metal-organic matrix material core via a covalent bond (e.g., to an organic component in the matrix material) or via a coordination bond (e.g., to a metal in the metal-organic matrix material). Any suitable non-nucleic acid chemotherapeutic agent can be used. In some embodiments, the at least one non-nucleic acid chemotherapeutic agent is selected from the group including, but not limited to, cisplatin or oxaliplatin prodrugs, methotrexate, leucovorin, pemetrexed disodium, doxorubicin, vinblastine, vincristine, vindesine, cytarabine, azathioprine, melphalan, imatinib, anastrozole, letrozole, carboplatin, gemcitabine, paclitaxel, docetaxel, etoposide, 5-fluorouracil, and vinorelbine. In some embodiments, at least two chemotherapeutic agents (e.g., at least two different non-nucleic acid chemotherapeutic agents, such as cisplatin and carboplatin or prodrugs thereof) are incorporated in the metal-organic matrix material core.

In some embodiments, the plurality of therapeutic agents comprise at least one nucleic acid. In some embodiments, the at least one nucleic acid is a siRNA, a miRNA, or an AS ODN. The nucleic acid can be attached to the metal-organic matrix material via coordination bonds between phosphate groups on the nucleic acid and metal ions on an outer surface of the core and/or in pores in the core. Alternatively, the nucleic acid can be associated (covalently or non-covalently) with a coating layer on the core. For example, a nucleic acid can be associated with a lipid in a lipid bilayer or lipid single layer covering the outer surface of the nanoparticle core.

In some embodiments, the metal-organic matrix material core comprises a metal-organic framework (MOF) or nano-metal-organic framework (NMOF) that comprises metal-containing clusters or ions coordinated to organic molecules, wherein the material comprises repeating coordination units. The organic molecule can include, for example, carboxylate, phosphate, amino, mercapto, or hydroxyl groups to form coordinate bonds with a metal ion.

In some embodiments, the MOF or NMOF comprises a material comprising $Zr_6(\mu_3-O)_4(\mu_3-OH)_4$ (i.e., as the metal-containing cluster) and a dicarboxylate bridging ligand (i.e., as the organic molecule). In some embodiments, the dicarboxylate bridging ligand comprises an arylene moiety in the bridging ligand backbone. In some embodiments, the dicarboxylate bridging ligand further includes a group, such as an amino, hydroxyl, or thiol, that can form a covalent bond with a chemotherapeutic agent. In some embodiments, the dicarboxylate bridging ligand comprises an amino substituent. In some embodiments, the dicarboxylate bridging ligand is amino-triphenyldicarboxylic acid (amino-TPDC).

In some embodiments, at least one non-nucleic acid chemotherapeutic agent is covalently attached to a substituent on the dicarboxylate bridging unit. For example, the non-nucleic acid chemotherapeutic agent can include a carboxylic acid group that can form an amide bond with an amino substituent on the dicarboxylate bridging unit.

In some embodiments, the at least one non-nucleic acid chemotherapeutic agent is a cisplatin or oxaliplatin prodrug. For example, the non-nucleic acid chemotherapeutic agent can be a cisplatin or oxaliplatin prodrug that contains a carboxylic acid group, e.g., cis, cis, trans-$Pt(NH_3)_2Cl_2(OEt)(O_2CCH_2CH_2COOH)$ (a cisplatin prodrug) or cis, trans-$[Pt(dach)Cl_2(O_2CCH_2CH_2COOH)_2]$ (a oxaliplatin prodrug), which can form an amide bond with amino substituents on a bridging ligand in the nanoparticle core via the carboxylic acid group.

In some embodiments, at least one non-nucleic acid chemotherapeutic agent is incorporated in pores in the metal-organic matrix material core via a covalent bond to the dicarboxylate bridging ligand and wherein at least one nucleic acid is attached to an outer surface of the metal-organic matrix material core via a coordination bond with a metal ion on the outer surface of the metal-organic matrix material core. In some embodiments, the at least one nucleic acid is selected from the group comprising survivin siRNA, P-glycoprotein siRNA (P-gp siRNA), Bcl-2 siRNA, or a mixture of two or more thereof. In some embodiments, the at least one nucleic acid is a mixture of survivin siRNA, P-glycoprotein siRNA (P-gp siRNA), and Bcl-2 siRNA.

In some embodiments, the nanoparticle core can comprise between about 10 weight % and about 50 weight % of the non-nucleic acid chemotherapeutic agent (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 weight % of bisphosphonate weight % of the non-nucleic acid chemotherapeutic agent.)

In some embodiments, the nanoscale particle can have an average diameter of less than about 250 nm. In some embodiments, the average diameter is between about 50 and about 200 nm. In some embodiments, the nanoscale particle has an average diameter of between about 20 nm and about 180 nm (e.g., about 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, or about 180 nm). In some embodiments, the nanoscale particle has an average diameter of between about 90 nm and about 140 nm.

In some embodiments, the nanoscale particle comprises one or more coating agents or layers covering at least a portion of the outer surface of the outer surface of the metal-organic matrix material core. The coating layer can provide stabilization and/or functionalization. Such coating agents or layers can include, but are not limited to, metal oxides, polymers (e.g., a silica-based polymer, such as silica, poly(siloxane), or poly(silsesquioxane), or an organic or hydrophilic organic polymer), single lipid layers, lipid bilayers, and combinations thereof. In some embodiments, a passivating agent (such as a hydrophilic polymer, e.g., PEG or PVP)) and/or a targeting agent (such as an RGD peptide, an aptamer, an oligonucleotide, a polypeptide, an antibody, or a polysaccharide) and/or an imaging agent (such as a fluorescent moiety) can be attached (covalently or non-covalently) to a coating agent or layer. In some embodiments, a therapeutic agent can be covalently or non-covalently attached to a coating layer. In some embodiments, at least one nucleic acid is covalently or non-covalently attached to a coating layer.

In some embodiments, the coating agent or layer is a lipid bilayer. For example, in some embodiments, the metal-organic matrix material core is coated with a lipid bilayer comprising a cationic lipid and/or a functionalized lipid, wherein said functionalized lipid is a lipid functionalized with a group that can bond to a nucleic acid, and wherein at least one nucleic acid is covalently bonded to the functionalized lipid and/or attached to the cationic lipid via electrostatic interactions. In some embodiments, the lipid bilayer comprises a mixture comprising one or more of a thiol- or dithiol-functionalized 1,2-distearoyl-sn-glycero-3-phosphoethanolamine (DSPE), 1,2-dioleoyl-3-trimethylammonium propane (DOTAP), and 1,2-dioleoyl-sn-glycero-3-phosphocholine (DOPC). In some embodiments, the lipid bilayer comprises or further comprises one or more of 1,2-dioleoyl-sn-glycero-3-phosphate sodium salt (DOPA), cholesterol, and pegylated-DSPE.

In some embodiments, the metal-organic matrix material core comprises a metal bisphosphonate coordination polymer comprising a multivalent metal ion and a bisphosphonate. Any suitable multivalent metal ion can be used. In some embodiments, the multivalent metal ion is divalent. In some embodiments, the metal ion is $Ca^{2+}$, $Mg^{2+}$, $Mn^{2+}$, $Zn^{2+}$, or a combination thereof. In some embodiments, the metal is $Zn^{2+}$. In some embodiments, the bisphosphonate is a coordination complex that contains a metal ion (e.g., a Pt, Ir, or Ru ion). In some embodiments, the bisphosphonate is a chemotherapeutic prodrug. Thus, in some embodiments, a chemotherapeutic is present as a bridging ligand in the metal-organic material of the nanoparticle core. In some embodiments, the bisphosphonate is a cisplatin or oxaliplatin prodrug. For example, the bisphosphonate can be a bisphosphonate ester of cis, cis-trans-$[Pt(NH_3)_2Cl_2(OH)_2]$ or cis, trans-$[Pt(dach)Cl_2(OH)_2]$.

In some embodiments, the metal-organic matrix material core comprises up to about 50 weight % of bisphosphonate. In some embodiments, the metal-organic matrix material core comprises between about 10 weight % and about 50 weight % of bisphosphonate (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 weight % of bisphosphonate).

In some embodiments, the nanoscale particle comprising a metal-bisphosphonate core further comprises a lipid single or lipid bilayer coating. In some embodiments, the coating comprises one or more of survivin siRNA, P-gp siRNA, and Bcl-2 siRNA attached to the coating (e.g., covalently or non-covalently). In some embodiments, the coating comprises a mixture of survivin siRNA, P-gp siRNA, and Bcl-2 siRNA.

In some embodiments, the nanoscale particle comprises a metal-bisphosphonate core has a diameter between about 20 nm and about 180 nm (e.g., about 20, 30, 40, 50, 60, 70, 80, 90, 100, 110, 120, 130, 140, 150, 160, 170, or about 180 nm).

In some embodiments, the presently disclosed subject matter comprises a pharmaceutical formulation comprising one of the nanoscale particles described herein and a pharmaceutically acceptable carrier. In some embodiments, the pharmaceutically acceptable carrier is pharmaceutically acceptable in humans.

In some embodiments, the presently disclosed subject matter provides a method of treating cancer in a subject in need thereof using one of the nanoscale particles described herein. Accordingly, in some embodiments, the presently disclosed subject matter provides a method of treating a cancer in a subject wherein the method comprises administering to the subject a nanoscale particle or a formulation thereof. In some embodiments, the nanoscale particle comprises at least one at least one non-nucleic acid chemotherapeutic agent and at least one nucleic acid.

In some embodiments, the nanoparticle comprises a core comprising a MOF comprising $Zr_6(\mu_3-O)_4(\mu_3-OH)_4$ and a dicarboxylate bridging ligand, optionally wherein the dicarboxylate bridging ligand comprises an amino substituent (e.g., for covalent attachment to a non-nucleic acid chemotherapeutic agent). In some embodiments, the core comprises a metal bisphosphonate coordination polymer, e.g., wherein the bisphosphonate comprises a chemotherapeutic agent prodrug.

In some embodiments, the at least one non-nucleic acid chemotherapeutic agent of the nanoparticle is a cisplatin or oxaliplatin prodrug and the at least one nucleic acid or the nanoparticle is selected from survivin siRNA, P-gp siRNA, Bcl-2 siRNA, and combinations thereof. In some embodiments, the at least one nucleic acid is a mixture of survivin siRNA, P-gp siRNA, and Bcl-2 siRNA.

The present methods can be used to treat any suitable cancer. In some embodiments, the cancer is a lung cancer, a pancreatic cancer, an ovarian cancer, a breast cancer or a colon cancer. In some embodiments, the cancer is ovarian cancer. In some embodiments, the cancer is a drug resistant cancer, such as a cisplatin resistant cancer (e.g., a cisplatin resistant ovarian cancer).

In some embodiments, the presently disclosed subject matter provides methods of preparing nanoscale particles comprising a metal-organic matrix material core and a plurality of therapeutic agents. In some embodiments, the nanoscale particles can be prepared using a microemulsion method. Microemulsion methods are described, for example, in U.S. Patent Application Publication No. 2014/0234210 and International Publication No. WO 2013/0971, each of which is incorporated herein by reference in its entirety. In some embodiments, the nanoscale particle can be prepared by a method comprising: (a) contacting a microemulsion comprising a metal ion with a microemulsion comprising a bisphosphonate, thereby forming a metal bisphosphonate coordination polymer nanoparticle; (b) dispersing the nanoparticle from (a) in a solution (e.g., an aqueous solution) comprising a cationic lipid and/or a functionalized lipid to form a cationic lipid-coated and/or functionalized lipid coated nanoparticle; and (c) contacting the lipid-coated nanoparticles with a solution comprising at least one nucleic acid. In some embodiments, the bisphosphonate is a cisplatin or oxaliplatin prodrug. In some embodiments, the bisphosphate microemulsion can further comprise a lipid, such as DOPA, DOTAP, DOPC, POPE, oleic acid, stearic acid, etc, such that the nanoparticle core can be formed already containing a lipid layer (e.g., a single lipid layer) over at least a portion of the outer surface of the core. In some embodiments, the nucleic acid solution comprises at least one or more of survivin siRNA, P-gp siRNA, Bcl-2 siRNA, and combinations thereof.

The metal ion can be provided by dissolving a metal compound in a microemulsion. The metal compound can be a compound of the formula $ML_x$, wherein x is an integer corresponding to the valency of the metal ion, M is a multivalent metal ion, and each L is a ligand. Suitable ligands for the metal compounds include, but are not limited to, halo, hydroxyl, sulfate, nitrate, and amino. In some embodiments, the metal compound is a hydrate or a solvate of a compound of the formula $ML_x$. In some embodiments, the metal compound is a metal halide (e.g., $CaCl_2$ or $MnCl_2$) or a hydrate or solvate thereof. In some embodiments, the metal compound is zinc nitrate (i.e., $Zn(NO_3)_2$).

Alternatively, the nanoscale particle can be prepared by a method comprising contacting a solution of a metal compound, such as a metal halide, with a solution comprising a dicarboxylic acid to prepare a metal organic matrix material core. In some embodiments, the dicarboxylic acid and the metal compound are in a solution of a polar organic solvent, such as dimethyl formamide (DMF). The dicarboxylic acid can comprise an additional substituent, e.g., a hydroxyl or amino group. Then the nanoparticle core can be contacted with a solution comprising a non-nucleic acid chemotherapeutic agent which includes a group that can form a bond with the additional substituent of the dicarboxylic acid under conditions where the non-nucleic acid bonds to the dicarboxylic acid. The solution can comprise an organic solvent and/or coupling reagents (e.g., diimidazoles). Then the nanoparticle core comprising the non-nucleic acid chemotherapeutic agent can be contacted with a solution (e.g., an aqueous solution) comprising one or more nucleic acids. The nucleic acids can associate via non-covalent bonding with the metal ions on an outer surface of the nanoparticle core. Alternatively, the nucleic acids can be provided in a solution (e.g., an aqueous solution) with one or more lipids, to which the nucleic acids can optionally be covalently or non-covalently bonded. Accordingly, the lipid/nucleic acid solution can form a lipid layer or lipid bilayer over the surface of the nanoparticle core. In some embodiments, the at least one nucleic acid is selected from survivin siRNA, P-gp siRNA, Bcl-2 siRNA, and combinations thereof.

In some embodiments the metal compound is a Zr compound, such as $ZrCl_4$ and the dicarboxylic acid is an amino-substituted dicarboxylic acid, such as amino-triphenyldicarboxylic acid. In some embodiments, the non-nucleic acid chemotherapeutic agent comprises a carboxylic acid substituent, and is contacted with the nanoparticle core in a solution that further comprises a diimidazole. In some embodiments, the non-nucleic acid chemotherapeutic agent is a cisplatin or oxaliplatin prodrug, optionally cis, cis, trans-$Pt(NH_3)_2Cl_2(OEt)(O_2CCH_2CH_2COOH)$ (a cisplatin prodrug) or cis, trans-$[Pt(dach)Cl_2(O_2CCH_2CH_2COOH)_2]$ (an oxaliplatin prodrug), that contains a carboxylic acid substituent.

III. Nanoscale Coordination Polymer Particles for Co-Delivery of Chemotherapeutics and Photosensitizers As described hereinabove, nanoparticulate systems can enhance the delivery of small molecule drugs and biologics to tumor sites via the enhanced permeability and retention (EPR) effect by taking advantage of the leaky blood vasculatures and reduced lymphatic drainage in tumors. Nanoparticles can also be used to increase the accumulation of PSs at tumor sites to enhance PDT efficacy without overly relying on high-precision light delivery. Desirable nanocarrier characteristics for PSs include a high payload, release of the PS agent in a controlled manner to afford a high PS concentration during the typically short duration of light activation (e.g., about 30 min), and suitable molecular properties to localize inside cancer cells and to minimize self-quenching of photochemical excited states and other processes in order to efficiently generate ROS for selective killing of cancer cells. The presently disclosed NCP particle platform can be used to provide these characteristics. In some embodiments, the presently disclosed subject matter provides a foundation for constructing multifunctional core-shell hybrid nanoparticles that can selectively deliver and trigger release of conventional chemotherapeutic and PDT agents inside cancer cells to enable synergistic and effective combination chemotherapy and PDT.

FIG. 11 shows a schematic drawing for an exemplary particle for combined chemotherapy and PDT according to the presently disclosed subject matter. The particle shown in FIG. 11 comprises a NCP-pyrolipid core-shell nanoparticle with a chemotherapeutic (e.g., a cisplatin prodrug) embedded in the NCP core and pyrolipid in the shell to provide combination PDT and chemotherapy with a single delivery system. The NCP-pyrolipid particle maintains structural integrity extracellularly, but can release the chemotherapeutic and pyrolipid in a triggered manner intracellularly to allow for time- and site-specific cytotoxicity. As described hereinbelow, synergistic actions of chemotherapy from the chemotherapeutic and PDT from the pyrolipid and light activation using the NCP-pyrolipid particle can afford enhanced anticancer efficacy in cancer cells (e.g., head and neck cancer cells) and in a xenograft mouse model of cancer after intravenous administration when compared to free therapeutics and monotherapy particles.

Accordingly, in some embodiments, the presently disclosed subject matter provides a nanoscale particle for co-delivery of a plurality of therapeutic agents, said nanoscale particle comprising: a core comprising a metal-organic matrix material, optionally wherein the metal-organic matrix material comprises a coordination polymer; and a plurality of therapeutic agents, wherein said plurality of therapeutic agents comprises at least one chemotherapeutic agent (i.e., one non-PS chemotherapeutic agent) and at least one photosensitizer.

In some embodiments, the plurality of therapeutic agents comprise at least one non-nucleic acid chemotherapeutic agent incorporated in the metal-organic matrix material core. For example, the at least one non-nucleic acid chemotherapeutic agent can be incorporated in the metal-organic matrix material core via a covalent bond (e.g., to an organic component in the matrix material) or via a coordination bond (e.g., to a metal in the metal-organic matrix material). Any suitable non-nucleic acid chemotherapeutic agent can be used. In some embodiments, the at least one non-nucleic acid chemotherapeutic agent is selected from the group including, but not limited to, cisplatin or oxaliplatin prodrugs, methotrexate, leucovorin, pemetrexed disodium, doxorubicin, vinblastine, vincristine, vindesine, cytarabine, azathioprine, melphalan, imatinib, anastrozole, letrozole, carboplatin, gemcitabine, paclitaxel, docetaxel, etoposide, vinorelbine, and 5-fluorouracil. In some embodiments, at least two chemotherapeutic agents (e.g., at least two different non-nucleic acid chemotherapeutic agents, such as cisplatin and carboplatin or prodrugs thereof) are incorporated in the metal-organic matrix material core.

In some embodiments, the non-nucleic acid chemotherapeutic agent is a bisphosphonate cisplatin or oxaliplatin prodrug and the metal-organic matrix material core comprises a metal bisphosphonate coordination polymer comprising a multivalent metal ion and said bisphosphonate cisplatin or oxaliplatin prodrug. Any suitable multivalent metal ion can be used. In some embodiments, the multivalent metal ion is a divalent metal ion. In some embodiments, the multivalent metal ion is $Ca^{2+}$, $Mg^{2+}$, $Mn^{2+}$, $Zn^{2+}$, or a combination thereof. In some embodiments, the bisphosphonate cisplatin or oxaliplatin prodrug is a bisphosphonate ester of cis, cis-trans-$[Pt(NH_3)_2Cl_2(OH)_2]$ and/or the metal ion is $Zn^{2+}$.

In some embodiments, the photosensitizer is covalently attached to a coating layer or layers surrounding a portion of the outer surface of the nanoparticle core. For instance, the nanoparticle can comprise one or more coating layers such as a metal oxide, a polymer, a single lipid layer, a lipid bilayer, and combinations thereof and the photosensitizer is covalently or non-covalently attached to a lipid in the coating. Any suitable photosensitizer can be used, such as but not limited to, porphyrins, chlorophylls dyes, or derivatives or analogs thereof. In some embodiments, the coating layer or layers includes a lipid single layer or lipid bilayer comprising a pyrolipid, i.e., a lipid covalently attached to a porphyrin or a derivative or analog thereof.

The lipid layer or bilayer can also include other lipids and/or passivating or targeting agents, such as hydrophilic polymers and or RGD peptides. In some embodiments, the lipid bilayer or lipid single layer further comprises one or more of cholesterol, 1,2-distearoyl-sn-glycero-3-phosphoethanolamine (DSPE), 1,2-Distearoyl-sn-glycero-3-phosphocholine (DSPC) 1,2-dioleoyl-3-trimethylammonium propane (DOTAP), 1,2-dioleoyl-sn-glycero-3-phosphocholine (DOPC), 1,2-dioleoyl-sn-glycero-3-phosphate sodium salt (DOPA), and pegylated-DSPE.

In some embodiments, the nanoscale particle can have an average diameter of less than about 250 nm. In some embodiments, the average diameter is between about 20 and about 200 nm. In some embodiments, the nanoscale particle has an average diameter of between about 20 nm and about 180 nm (e.g., about 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, or about 180 nm). In some embodiments, the nanoscale particle has an average diameter of between about 90 nm and about 140 nm. In some embodiments, the diameter is about 108 nm.

In some embodiments, the presently disclosed subject matter provides a pharmaceutical formulation comprising a nanoscale particle of the presently disclosed subject matter that includes a photosensitizer (e.g., in a lipid single layer or lipid bilayer surrounding a metal organic core) as one of a plurality of therapeutic agents and a pharmaceutically acceptable carrier.

In some embodiments, the presently disclosed subject matter provides a method of treating a cancer to a subject in need thereof, wherein the method comprises administering to the subject nanoscale particle of the presently disclosed subject matter that includes a photosensitizer as one of a plurality of therapeutic agents, and irradiating the subject or a treatment area of the subject with radiation having a wavelength suitable to activate the photosensitizer. Irradiation activates the photosensitizer, which produces reactive oxygen species, such as singlet oxygen. The wavelength used for irradiation can depend upon the photosensitizer. In some embodiments, the photosensitizer is a pyrolipid and the irradiation is performed at a wavelength ranging from 630 nm to 740 nm (e.g. 630, 640, 650, 660, 670, 680, 690, 700, 710, 720, 730, or about 740 nm).

Any suitable cancer can be treated, such as, but not limited to, a head and neck cancer, breast cancer, a gynecological cancer, a brain cancer, a colorectal cancer, mesothelioma, and a pancreatic cancer. In some embodiments, the cancer is a head and neck cancer. In some embodiments, the head and neck cancer is a cisplatin resistant head and neck cancer.

In some embodiments, the at least one chemotherapeutic agent of the nanoscale particle is a cisplatin or oxaliplatin prodrug. In some embodiments, the prodrug is a bisphosphonate ester of cisplatin or oxaliplatin. In some embodiments, the nanoparticle core comprises a metal-bisphosphonate coordination polymer. In some embodiments the metal is Zn. In some embodiments, the nanoparticle can comprise a cisplatin prodrug and pyrolipid in a molar ratio of about 1:1, 1:2, 1:3, 1:4, 1:5, 1:6, 1:7, 1:8, 1:9, or 1:10. In some embodiments, the nanoparticle comprises about 10-50 weight % cisplatin prodrug (e.g., embedded in the nanoparticle core) and about 10-50 weight % pyrolipid (in a coating layer).

In some embodiments, the presently disclosed subject matter provides a method of preparing a nanoscale particle comprising a chemotherapeutic agent and a photosensitizer via a microemulsion method. In some embodiments, the method comprises: (a) contacting a microemulsion comprising a metal ion with a microemulsion comprising a bisphosphonate, thereby forming a metal bisphosphonate coordination polymer nanoparticle; and (b) dispersing the nanoparticle from (a) in a solution comprising a pyrolipid to form a pyrolipid-coated nanoparticle. In some embodiments, the bisphosphonate is a cisplatin or oxaliplatin prodrug. In some embodiments, the solution comprising the further comprises one or more additional lipid coating components, such as cholesterol, 1,2-Distearoyl-sn-glycero-3-phosphocholine (DSPC), and pegylated 1,2-distearoyl-sn-glycero-3-phosphoethanolamine (DSPE).

IV. siRNA Delivery

Although nanoparticulate delivery systems have been shown to enhance anticancer efficacy of chemotherapeutic agents by improving delivery and reducing toxicity through the enhanced permeability and retention (EPR) effect, efficient delivery of siRNAs targeting tumor cells in vivo remains an unsolved problem. Endosomal escape is a critical step for triggering siRNA-mediated gene silencing intracellularly. The commonly exploited proton sponge effect for endosomal escape relies on a cationic component such as cationic phospholipids and polymers, leading to a positively charged delivery vehicle, which is unfavorable for achieving prolonged systemic circulation and minimal unspecific mononuclear phagocyte system (MPS) uptake. Thus, there is a need for the development of an efficient nanoplatform that carries high payloads of siRNAs with efficient endosomal escape without compromising the neutral surface charge needed for high tumor accumulation by taking advantage of the EPR effect via systemic injection. Nanoscale coordination polymers can be used to deliver individual or pooled siRNAs for cancer therapy. NCPs offer fundamentally new triggered release and unique endosomal escape mechanisms for efficient delivery of siRNAs to tumors in vivo. The modular and scalable NCP synthesis described herein enables the incorporation of siRNAs targeting multiple genes to achieve "cocktail" siRNA therapies and facilitates clinical translation of the NCP technology for cancer treatment.

Despite decades of intense research efforts, the treatment of late-stage cancers in the clinic has achieved limited success and remains largely elusive. The immune system is restrained by complex, negative feedback mechanisms of tumors that evolve to protect the host against autoimmunity and prevent antitumor immunity. Tumor cells exploit multiple strategies to evade detection and elimination by the immune system. siRNA mediated RNAi can be employed to activate the immune system by blocking multiple immunosuppressive pathways in both tumor cells and tumor stromal cells. The robust NCP platform described herein can deliver siRNA cocktails to the tumor site with high efficiency and endosomal escape capability to elicit effective immunotherapy in resistant cancers, such as resistant ovarian cancer (OCa).

Programmed death 1 (PD-1) is a key immune checkpoint receptor expressed by activated T cells, B cells, monocytes, dendritic cells (DCs), etc. PD-1 functions primarily in peripheral tissues, where these immune cells can encounter the immunosuppressive PD-1 ligands, such as PD-L1, which is overexpressed in not only activated immune cells, but also in tumor cells and stromal cells. PD-L1 expression correlates with unfavorable prognosis in OCa. Blocking PD1 expression on T helper type 1 ($T_H1$) cells can stabilize $T_H1$ cell differentiation during PD-L1 challenge and prevent $T_H1$ cells from turning into regulatory T ($T_{reg}$) cells that severely impair cell-mediated immunity. Previous clinical studies demonstrated that antibody-mediated blockade of PD-L1 induced durable tumor regression (objective response rate of 6 to 17%) and prolonged stabilization of disease (rates of 12 to 41% at 24 weeks) in patients with multiple advanced cancers. Down-regulation of PD-L1 expression in tumors by siRNAs can inhibit the interaction between PD-1 and PD-L1 and thus enhance T-cell responses for mediating potent anticancer activity.

The secretion of the chemokine CC motif ligand 21 by tumor cells has been identified as a central event in the generation of an immunotolerant lymphoid-like stroma, which features an impaired cytokine milieu and the accumulation of immunosuppressive cell population. This phenomenon was shown to be mediated by chemokine CC motif receptor 7 (CCR7) on stromal but not tumor cells, and immunocompetence is restored to normal levels in $Ccr7^{-/-}$ mice or following the blockade of CCR7 by specific antibodies. Down-regulation of CCR7 expression in tumor stromal cells by siRNAs can modulate the tumor microenvironment for stimulating the anti-tumor immunity.

Alteration in tumor cell metabolism also induces immune suppression, as it depletes the tumor microenvironment of essential nutrients and leads to the accelerated production of immune suppressive metabolites. Indolamine-2,3-dioxygenase (IDO) which is upregulated in human tumor cells will promote $T_{reg}$ and myeloid-derived suppressor cell (MDSC) activation, inhibit the proliferation of tumor infiltrating T-cells, and induce the apoptosis of effector T-cells. Down-regulation of IDO expression in tumor cells by siRNAs can cause a reduction in immune suppression.

Since both cellular and humoral components of the tumor cell microenvironment are targets for immunotherapeutic strategies, NCP/siRNAs can be used to deliver a cocktail of siRNAs targeting PD-L1, CCR7, and IDO to OCa. In some embodiments, the NCP/siRNA can be a core-shell nanoparticle with the coordination polymer carrying bis(ethylenediamine)platinum bisphosphonic acid (Pten) in the solid core and a lipid bilayer carrying siRNAs in the shell. Pten-NCP/siRNAs incorporating siRNAs in the shells of particles of Pten-NCP that carry Pten are described hereinbelow.

V. Formulations

The compositions of the presently disclosed subject matter comprise in some embodiments a composition that includes a pharmaceutically acceptable carrier. Any suitable pharmaceutical formulation can be used to prepare the compositions for administration to a subject. In some embodiments, the composition and/or carriers can be pharmaceutically acceptable in humans.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the subject; and aqueous and non-aqueous sterile suspensions that can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS), in one example in the range of 0.1 to 10 mg/ml, in another example about 2.0 mg/ml; and/or mannitol or another sugar, for example in the range of 10 to 100 mg/ml, in another example about 30 mg/ml; and/or phosphate-buffered saline (PBS).

It should be understood that in addition to the ingredients particularly mentioned above, the formulations of this presently disclosed subject matter can include other agents conventional in the art having regard to the type of formulation in question. For example, sterile pyrogen-free aqueous and non-aqueous solutions can be used.

VI. Subjects

The methods and compositions disclosed herein can be used on a sample either in vitro (for example, on isolated cells or tissues) or in vivo in a subject (i.e. living organism, such as a patient). In some embodiments, the subject is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided are methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the treatment of livestock including, but not limited to domesticated swine (pigs and hogs), ruminants, horses, poultry, and the like.

VII. Administration

Suitable methods for administration of a composition of the presently disclosed subject matter include, but are not limited to intravenous and intratumoral injection, oral administration, subcutaneous administration, intraperitoneal injection, intracranial injection, and rectal administration. Alternatively, a composition can be deposited at a site in need of treatment in any other manner, for example by spraying a composition within the pulmonary pathways. The particular mode of administering a composition of the presently disclosed subject matter depends on various factors, including the distribution and abundance of cells to be treated and mechanisms for metabolism or removal of the composition from its site of administration. For example, relatively superficial tumors can be injected intratumorally. By contrast, internal tumors can be treated following intravenous injection.

In one embodiment, the method of administration encompasses features for regionalized delivery or accumulation at the site to be treated. In some embodiments, a composition is delivered intratumorally. In some embodiments, selective delivery of a composition to a target is accomplished by intravenous injection of the composition followed by photodynamic treatment (light irradiation) of the target.

For delivery of compositions to pulmonary pathways, compositions of the presently disclosed subject matter can be formulated as an aerosol or coarse spray. Methods for preparation and administration of aerosol or spray formulations can be found, for example, in U.S. Pat. Nos. 5,858,784; 6,013,638; 6,022,737; and 6,136,295.

VIII. Doses

An effective dose of a composition of the presently disclosed subject matter is administered to a subject. An "effective amount" is an amount of the composition sufficient to produce detectable treatment. Actual dosage levels of constituents of the compositions of the presently disclosed subject matter can be varied so as to administer an amount of the composition that is effective to achieve the desired effect for a particular subject and/or target. The selected dosage level can depend upon the activity (e.g., MRI relaxivity or bisphosphonate drug loading) of the composition and the route of administration.

After review of the disclosure herein of the presently disclosed subject matter, one of ordinary skill in the art can tailor the dosages to an individual subject, taking into account the particular formulation, method of administration to be used with the composition, and nature of the target to be treated. Such adjustments or variations, as well as evaluation of when and how to make such adjustments or variations, are well known to those of ordinary skill in the art.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Nanoscale Coordination Polymers Made with Cisplatin or Oxaliplatin Prodrugs and Having RNAs Adsorbed on the Particle Surface Via Electrostatic Interactions 1.1. Synthesis of a Cisplatin Prodrug (cisPtBp):

Scheme 1. Structure of bisphosphonate cisplatin prodrug.

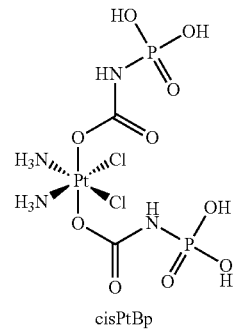

cisPtBp

A bisphosphonate cisplatin prodrug, cisPtBp, (Scheme 1) was prepared as described in International Publication No. WO 2013/009701. More particularly, to a suspension of cis, cis, trans-$[Pt(NH_3)_2Cl_2(OH)_2]$ (0.5 g, 1.5 mmol) in 2 mL of dimethylformamide (DMF) was added 1 mL of DMF solution containing 4 equiv of the diethoxyphosphinyl isocyanate (0.92 mL, 6.0 mmol). The resulting mixture was stirred in the dark at room temperature for 12 h. The solution was filtered, and the resulting bisphosphonate ester complex was precipitated by the addition of diethyl ether, and washed with diethyl ether for at least twice to remove the residual DMF. Yield: 80%. $^1$H NMR in DMSO-$d_6$: δ 8.61 (d, 2H); 6.58 (br, 6H); 3.97 (q, 8H); 1.20 (t, 12H).

The bisphosphonate ester complex was dried under vacuum for 4 h before it was used for subsequent reactions. To a solution of the bisphosphonate ester complex (250 mg, 0.36 mmol) in 3 mL of dry DMF was added 475 uL of trimethylsilyl bromide (3.6 mmol) at 0° C., and the mixture was allowed to react in the dark with nitrogen protection for r.t. for 18 h. After concentrating the solution, the intermediate was precipitated by the addition of dichloromethane and further washing with dichloromethane (DCM) at least twice. The solid was dissolved in methanol (MeOH) and stirred at room temperature for 8 h in order to hydrolyze the silyl ester. After concentrating the solution, DCM was poured into the reaction mixture to precipitate the desired cisPtBp product, and the solid was washed with DCM twice. Yield: 60%. $^1$H NMR in $D_2O$. δ 6.62 (m, 6H). ESI-MS for $[M+H]^+$: 578.9 calcd; 579.0 found.

1.2. Preparation of siRNA Loaded NCP-1 (NCP-1/siRNA):

Two hundred microliters of 25 mg/mL cisPtBp sodium salt aqueous solution and 0.2 mL of 100 mg/mL $Zn(NO_3)_2$ aqueous solution were added to 5 mL of 0.3 M Triton X-100/1.5 M 1-hexanol in cyclohexane mixture, respectively, to form w=7.4 microemulsions. Two hundred microliter of DOPA (200 mg/mL in chloroform ($CHCl_3$)) was added to the cisPtBp sodium salt microemulsion and the stirring was continued for 15 mins until clear solution formed. The two microemulsions were combined, and the resultant 10 mL of microemulsion was stirred for an additional 30 minutes to yield nanoscale coordination polymers (NCPs). See Scheme 2, below. The NCPs were then washed with cyclohexane and ethanol to remove extra DOPA, and dispersed in THF. The cationic lipid coated NCP-1 was achieved by adding a THF solution of DOTAP, cholesterol (molar ratio of DOTAP/cholesterol=2:1), 20 mol % DSPE-PEG2K, and NCPs to 30% (v/v) ethanol/water at 50° C. THF and ethanol was completely evaporated and the NCP-1 solution was allowed to cool down to room temperature before use. The control nanoparticles (Zncontrol) were prepared with the same method except that sodium pyrophosphate decahydrate was used instead of cisPtBp sodium salt to form the NCPs.

suspension was centrifuged at 13,000 rpm for 30 min. The amount of free TAMRA-siRNA in the supernatant was determined with fluorimetry based on the standard curve (TAMRA, $\lambda ex=565$ nm, $\lambda em=580$ nm). LE was calculated from the following equation:

$$LE(\%) = \frac{W_0 - W_1}{W_0} \times 100$$

Scheme 2. Structure of zinc-cisplatin bisphosphonate coordination polymer.

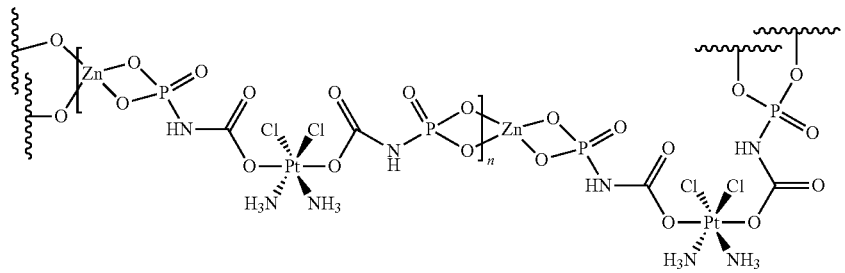

Survivin siRNA, Bcl-2 siRNA, and P-glycoprotein (P-gp) siRNA were dissolved in DEPC-treated water at weight ratio of 1:1:1 to achieve 2 mg/mL pooled siRNAs solution. Cationic lipid coated NCP-1 (2 mg/mL) was mixed with siRNA solution (2 mg/mL) at weight ratio of cisplatin:siRNA=4:1, and the mixture was kept stirring for 30 min at 800 rpm and room temperature to allow the adsorption of negatively charged siRNA onto the positively charged NCP-1 surface.

ICP-MS was used to analyze the Pt concentration of NCP to calculate the cisplatin loading. The cisplatin loading of NCP-1 was determined to be 40-50 wt %.

The particle size, polydispersity index (PDI), and Zeta potential of NCP-1 and NCP-1/siRNA in phosphate buffered solution (PBS) were determined by Zetasizer (Nano ZS, Malvern, UK). The particle size, PDI, and Zeta potential of NCP-1 and NCP-1/siRNA were 134.2±3.4 nm, 0.076±0.013, and 16.3±2.6 mV; 156.3±6.7 nm, 0.087±0.021, and −3.1±0.5 mV, respectively. The slightly elevated particle size and negative charge of NCP-1/siRNA confirmed the successful siRNA adsorption. Zncontrol particles loaded with siRNA (Zncontrol/siRNA) was also prepared, and the their size, PDI, and surface charge were 144.2±2.4 nm, 0.102±0.022, and −2.9±0.4 mV, respectively.

Figure 3:
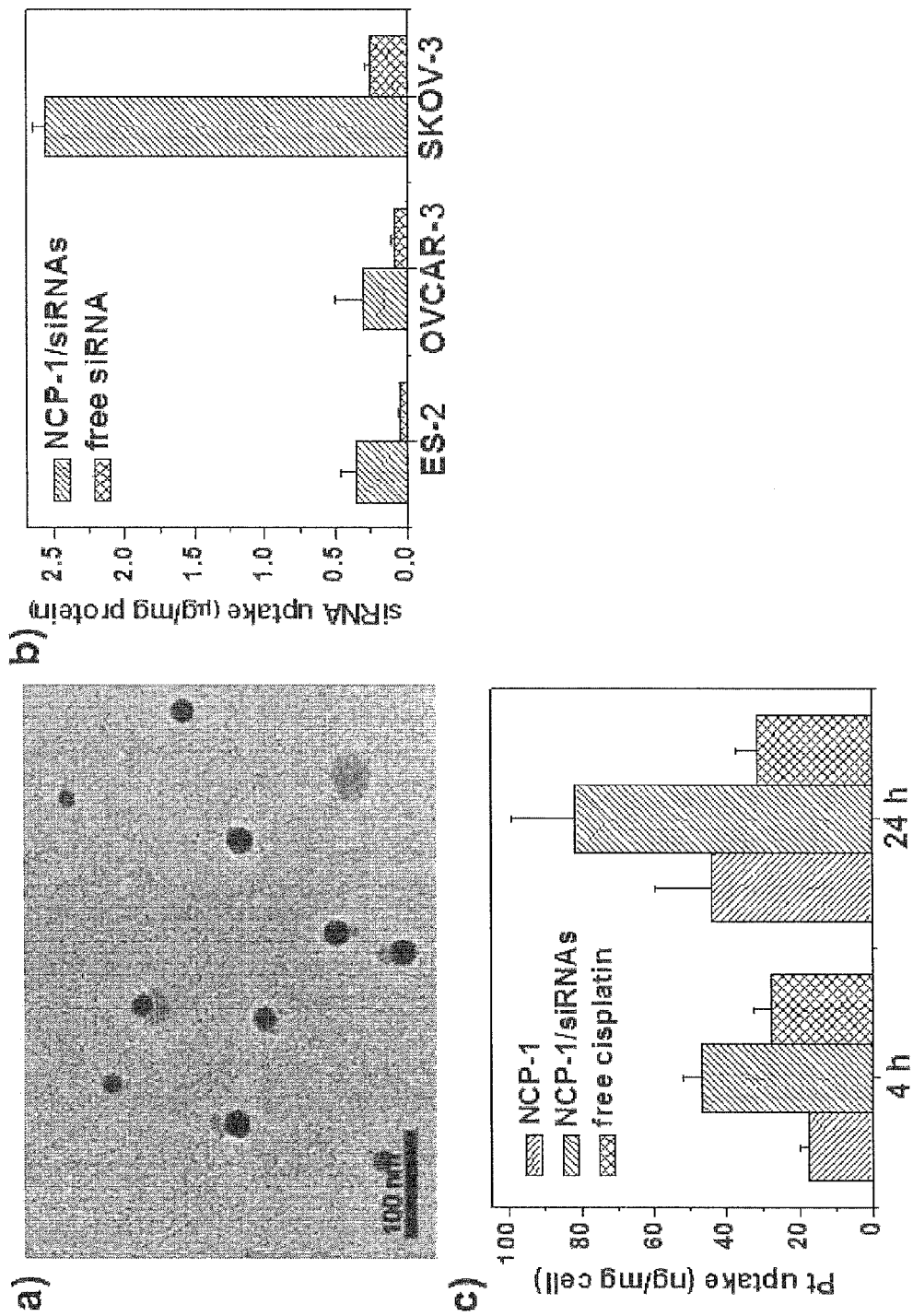
FIG. 3 shows (a) a TEM image showing particle morphology, (b) a graph showing cellular siRNA uptake and (c) a graph showing cellular Pt uptake of nanoscale coordination polymer nanoparticles carrying cisplatin and a pool of siRNAs including siRNAs targeting Bcl-2, P-gp, and survivin in human ovarian cancer cells. The nanoparticles are spherical and mono-dispersed with a diameter of ~20 nm by TEM. siRNA and cisplatin uptake was significantly promoted after being incorporated into the nanoparticles.

Transmission electron microscopy (TEM, JEM 100CX-II, JOEL Ltd, Tokyo, Japan) was used to observe the morphology of NCP-1/siRNA. The morphology of NCP-1/siRNA was spherical, mono-dispersed, and well-defined. See FIG. 3(a).

The association of siRNA with NCP-1 was firstly determined with gel retardation assay on 4% (w/v) agarose gel electrophoresis containing 0.25 µg/mL of ethidium bromide (EB). The movement of siRNA loaded into NCP-1 was completely retarded compared to the control naked siRNA, suggesting that NCP-1 could efficiently complex with siRNA at a cisplatin/siRNA weight ratio of 4.

The loading efficiency (LE) of siRNA into NCP-1 was quantitatively determined by fluorimetry. TAMRA-labeled siRNA was encapsulated into NCP-1 and the nanoparticle where $W_0$ and $W_1$ stand for the content of total siRNA and free siRNA in the supernatant, respectively. The siRNA loading efficiency was determined to be as high as 91.2±4.9%.

1.3. siRNA Integrity in Serum:

NCP-1/siRNA containing 1 µg of siRNA was mixed with an equal volume of fetal bovine serum (FBS). After incubation for a predetermined time at 37° C., the mixture was heated at 80° C. for 5 min to inactivate the nucleases and disrupt the NCP-1 structure. Thus, the siRNA was dissociated from NCP-1/siRNA, and its integrity was subsequently evaluated on 4% (w/v) agarose gel electrophoresis. Naked siRNA solution containing 1 µg of siRNA served as control. NCP-1/siRNA exhibited preferable capability to protect siRNA from nuclease degradation upon incubation with serum up to 4 h.

1.4. In Vitro siRNA Release:

To evaluate siRNA release profiles from NCP-1/siRNA, nanoparticles containing 1 µg of TAMRA-siRNA were incubated with 1 mL of PBS at 37° C. under shaking. At each predetermined time interval, the suspension was centrifuged at 13,000 rpm for 10 min and 0.5 mL of the supernatant was quantified for TAMRA-siRNA content by fluorimetry. An equal volume of the release medium was added, and the precipitate was resuspended before further incubation. NCP-1/siRNA could release siRNA in PBS with about 40% release rate in 2 h and a complete release after 24 h. The siRNA is slowly released from the NCP.

1.5. siRNA Cellular Uptake:

Three kinds of ovarian cancer cell lines including ES-2, OVCAR-3, and SKOV-3 cells were seeded on 24-well plate at $1\times10^5$ cells per well and cultured for 24 h. TAMRA-siRNA-containing NCP-1/siRNA and naked TAMRA-siRNA solution (2 mg/mL) were added (0.4 µg siRNA/well). Following a 4 hour incubation, cells were washed with PBS three times and then lysed with 0.5% (w/v) sodium dodecyl sulfate (SDS, pH 8.0). The lysate was quantified for TAMRA-siRNA by fluorimetry and protein content by the BCA kit (Promega Corporation, Madison, Wis., United States of America). Uptake level was expressed as the amount of TAMRA-siRNA associated with 1 mg of cellular protein. Compared to naked siRNA solution, siRNA uptake amounts of NCP-1/siRNA were significantly increased, indicating that NCP-1/siRNA could assist in the siRNA internalization. See FIG. 3(b). The cisplatin internalization was also promoted by the NCP-1/siRNAs, which might be due to the down-regulation of P-gp that decreases the nanoparticle/cisplatin efflux. See FIG. 3(c).

To directly observe the internalization of NCP-1/siRNA into ES-2, OVCAR-3, and SKOV-3 cells, cells were incubated with NCP-1/siRNA containing TAMRA-siRNA for 4 h at 37° C. The cells were washed with PBS three times, fixed with 4% paraformaldehyde, stained with 4',6-diamidino-2-phenylindole (DAPI, 10 µg/mL), and observed under confocal laser scanning microscopy (CLSM). Large amounts of siRNA localized in the cytoplasm of all three kinds of ovarian cancer cells.

To visualize co-localization of internalized NCP-1/siRNA with endosomal/lysosomal compartments, cells were incubated with NCP-1/siRNA containing TAMRA-siRNA for 2 h at 37° C. The cells were washed with PBS three times, fixed with 4% paraformaldehyde, and stained with DAPI (10 µg/mL) and Lysotracker Green (100 nM) before observation via CLSM. After a 2-h incubation, the majority of siRNA encapsulated in the NCP-1/siRNA escaped from the endo-/lysosome entrapment.

1.6. In Vitro Transfection Efficiency of NCP-1/siRNA:

ES-2, OVCAR-3, and SKOV-3 cells were seeded at $2\times10^5$ cells per well in 24-well plates and further cultured for 24 h. The culture media were replaced by 1 mL of pre-warmed and fresh culture media containing 10% FBS prior to the experiment. NCP-1/siRNA containing pooled siRNAs, NCP-1/siRNA containing single kind of siRNA, Zncontrol/siRNA containing pooled siRNAs, and NCP-1 were added to the cells at a siRNA dose of 0.4 µg per well, corresponding to the cisplatin dose of 1.6 µg per well. Following incubation for 4 h, the culture media were replaced by pre-warmed and fresh culture media containing 10% FBS, and a further 20-h incubation was allowed. The supernatant of the culture media was collected for the determination of extracellular survivin and P-gp production by enzyme-linked immunosorbant assay (ELISA; R&D Systems, Minneapolis, Minn., United States of America; MyBiosource, San Diego, Calif., United States of America) following manufacture instructions. The cells were lysed, and the Bcl-2 amount in the lysate was quantified by ELISA (R&D Systems, Minneapolis, Minn., United States of America). NCP-1/siRNA evoked potent gene silencing in ovarian cancer cells (Tables 1a, 1b, and 1c). Zncontrol/siRNA was also capable of down-regulating the gene expression. The slightly decreased survivin and Bcl-2 expression levels in NCP-1 group might be attributed to the cytotoxicity induced by cisplatin incorporated in the nanoparticles that influenced the expression levels of tumor growth relevant genes including survivin and Bcl-2.

TABLE 1a

Bcl-2 protein level

| | control | NCP-1 | NCP-1/siRNAs | NCP-1/siBcl-2 | Zn control/siRNAs |
|---|---|---|---|---|---|
| ES-2 | 1.00 ± 0.07 | 0.79 ± 0.04 | 0.48 ± 0.10 | 0.47 ± 0.06 | 0.58 ± 0.03 |
| OVCAR-3 | 1.00 ± 0.06 | 0.73 ± 0.07 | 0.26 ± 0.06 | 0.24 ± 0.07 | 0.52 ± 0.06 |
| SKOV-3 | 1.00 ± 0.16 | 0.82 ± 0.08 | 0.16 ± 0.02 | 0.20 ± 0.03 | 0.42 ± 0.04 |

TABLE 1b

P-gp protein level

| | control | NCP-1 | NCP-1/siRNAs | NCP-1/siP-gp | Zn control/siRNAs |
|---|---|---|---|---|---|
| ES-2 | 1.00 ± 0.04 | 0.70 ± 0.13 | 0.16 ± 0.01 | 0.16 ± 0.02 | 0.23 ± 0.06 |
| OVCAR-3 | 1.00 ± 0.14 | 0.63 ± 0.03 | 0.41 ± 0.05 | 0.36 ± 0.04 | 0.37 ± 0.04 |
| SKOV-3 | 1.00 ± 0.17 | 0.72 ± 0.11 | 0.54 ± 0.09 | 0.61 ± 0.09 | 0.61 ± 0.08 |

TABLE 1c survivin protein level

| | control | NCP-1 | NCP-1/siRNAs | NCP-1/sisurvivin | Zn control/siRNAs |
|---|---|---|---|---|---|
| ES-2 | 1.00 ± 0.06 | 0.87 ± 0.05 | 0.14 ± 0.03 | 0.12 ± 0.01 | 0.38 ± 0.01 |
| OVCAR-3 | 1.00 ± 0.32 | 0.76 ± 0.03 | 0.14 ± 0.02 | 0.15 ± 0.01 | 0.36 ± 0.03 |
| SKOV-3 | 1.00 ± 0.08 | 0.77 ± 0.06 | 0.27 ± 0.04 | 0.26 ± 0.04 | 0.43 ± 0.02 |

The transfection efficiency mediated by NCP-1/pooled siRNAs was also compared to the commercially available transfection agent LIPOFECTAMINE® RNAiMAX (Life Technologies, Carlsbad, Calif., United States of America). SKOV-3 cells were seeded at $2\times10^5$ cells per well in 24-well plates and further cultured for 24 h. The culture media were replaced by 1 mL of pre-warmed and fresh culture media containing 10% FBS prior to the experiment. NCP-1/pooled siRNAs and LIPOFECTAMINE® RNAiMAX/siRNA complexes were added to the cells at various siRNA doses. Following incubation for 4 h, the culture media were replaced by pre-warmed and fresh culture media containing 10% FBS, and a further 20-h incubation was allowed. The supernatant of the culture media was collected for the determination of extracellular survivin and P-gp production by ELISA (R&D Systems, Minneapolis, Minn., United States of America; MyBiosource, San Diego, Calif., United States of America) following manufacture instructions. The cells were lysed, and the Bcl-2 amount in the lysate was quantified by ELISA (R&D Systems, Minneapolis, Minn., United States of America). Similar gene knockdown efficiencies were observed for NCP-1/pooled siRNAs and Lipo/pooled siRNAs at siRNA dose of 3 nM (Tables 2a, 2b, and 2c). After the siRNA dose was further decreased to 0.75 nM, the transfection efficiency mediated by NCP-1/pooled siRNAs was significantly more potent than Lipo/pooled siRNAs. NCP-1/pooled siRNAs still evoked effective gene silencing at siRNA dose of 0.3 nM, which is 10-fold lower than the optimal siRNA dose for LIPOFECTAMINE® RNAiMAX, with transfection efficiency of ~60-70%.

TABLE 2a

Bcl-2 protein level

|  | Control | NCP-1/siRNAs | Lipo/siRNAs |
|---|---|---|---|
| siRNA 30 nM |  | 0.17 ± 0.06 |  |
| siRNA 7.5 nM |  | 0.12 ± 0.03 |  |
| siRNA 3 nM |  | 0.25 ± 0.01 | 0.21 ± 0.02 |
| siRNA 0.75 nM |  | 0.26 ± 0.06 | 0.77 ± 0.10 |
| siRNA 0.3 nM |  | 0.61 ± 0.04 |  |
| siRNA 0 nM | 1.00 ± 0.29 |  |  |

TABLE 2b

P-gp protein level

|  | Control | NCP-1/siRNAs | Lipo/siRNAs |
|---|---|---|---|
| siRNA 30 nM |  | 0.30 ± 0.05 |  |
| siRNA 7.5 nM |  | 0.29 ± 0.02 |  |
| siRNA 3 nM |  | 0.44 ± 0.06 | 0.35 ± 0.02 |
| siRNA 0.75 nM |  | 0.52 ± 0.04 | 0.80 ± 0.06 |
| siRNA 0.3 nM |  | 0.69 ± 0.02 |  |
| siRNA 0 nM | 1.00 ± 0.05 |  |  |

TABLE 2c survivin protein level

|  | Control | NCP-1/siRNAs | Lipo/siRNAs |
|---|---|---|---|
| siRNA 30 nM |  | 0.12 ± 0.05 |  |
| siRNA 7.5 nM |  | 0.18 ± 0.03 |  |
| siRNA 3 nM |  | 0.37 ± 0.05 | 0.28 ± 0.03 |
| siRNA 0.75 nM |  | 0.42 ± 0.02 | 0.80 ± 0.04 |
| siRNA 0.3 nM |  | 0.61 ± 0.05 |  |
| siRNA 0 nM | 1.00 ± 0.03 |  |  |

Figure 6:
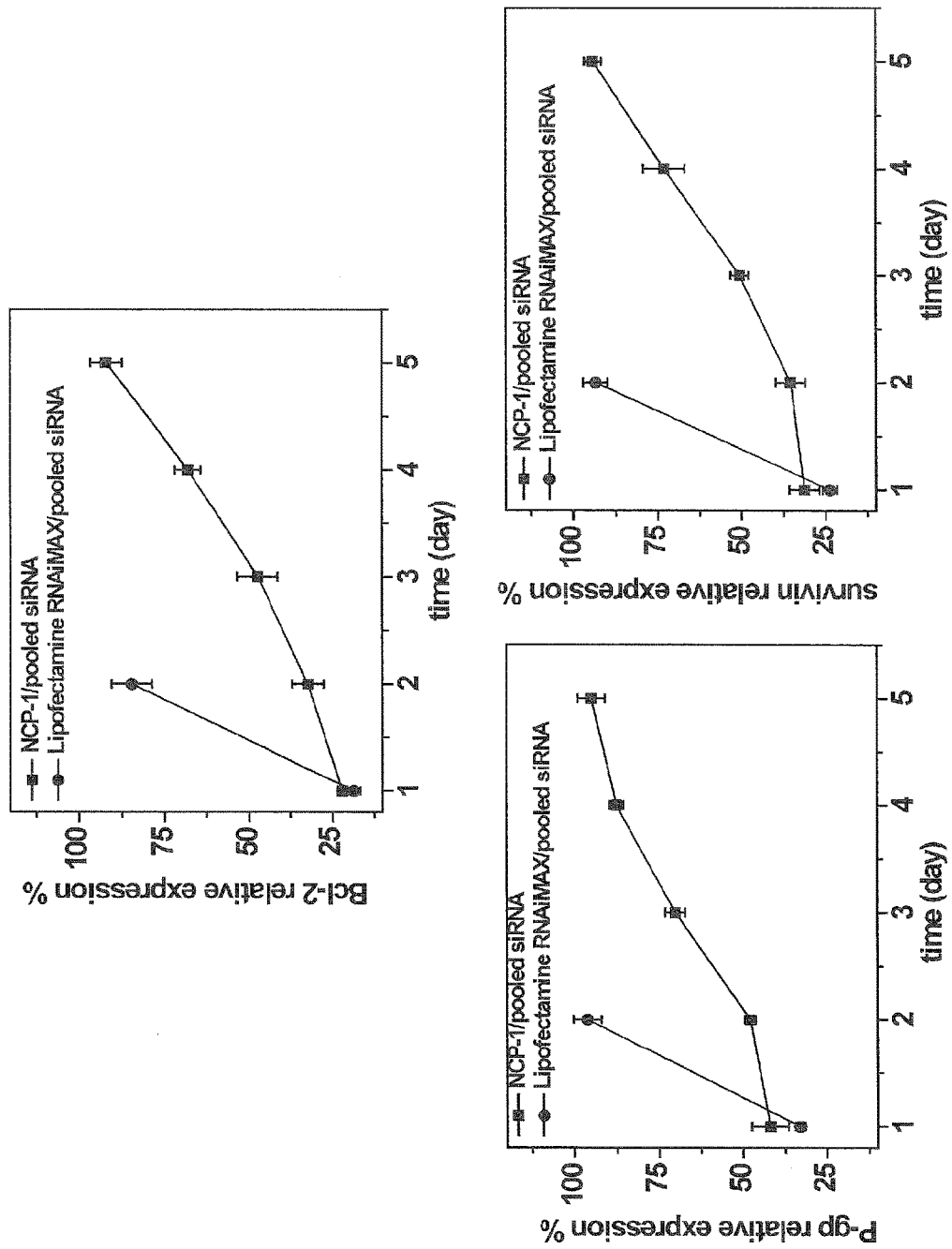
FIG. 6 is a set of graphs showing survivin (bottom right), Bcl-2 (top) and P-glycoprotein (P-gp, bottom left) relative expression levels in human ovarian cancer (SKOV-3) cells transfected with nanoscale coordination polymer nanoparticles embedded with cisplatin prodrugs and comprising pooled small interfering RNAs (siRNAs) non-covalently associated with a lipid bilayer surrounding the particle core (NCP-1/pooled siRNAs, squares) or with LIPOFECTAMINE® RNAiMAX (circles) at a siRNA concentration of 0.75 nanomolar (nM) for various time periods up to 5 days as indicated in the x-axis. Each data point represents the average of three measurements, with the error bars representing ±standard deviation.

The time course of transfection efficiency mediated by NPC-1/pooled siRNAs was evaluated in SKOV-3. Firstly, the long-term cytotoxicity of NCP-1/pooled siRNAs in SKOV-3 cells was evaluated. SKOV-3 cells were seeded at $4 \times 10^3$ cells per well in 96-well plates and further cultured for 24 h. NCP-1/pooled siRNAs nanoparticles were added to the cells at siRNA dose of 0.75 nM. Following incubation for 4 h, the culture media were replaced by pre-warmed and fresh culture media containing 10% FBS, and the cells were incubated for 5 days. The cells were passaged every 2 days at 1:3. The cell viability of SKOV-3 transfected with NCP-1/pooled siRNAs for 5 days was 92.5±5.8%, suggesting no cytotoxicity induced. Then the time-dependent transfection efficiency of NCP-1/pooled siRNAs was determined. SKOV-3 cells were seeded at $2 \times 10^5$ cells per well in 24-well plates and further cultured for 24 h. The culture media were replaced by 1 mL of pre-warmed and fresh culture media containing 10% FBS prior to the experiment. NCP-1/pooled siRNAs and LIPOFECTAMINE® RNAiMAX/siRNA complexes were added to the cells at siRNA dose of 0.75 nM. Following incubation for 4 h, the culture media were replaced by pre-warmed and fresh culture media containing 10% FBS, and the cells were incubated for various time periods. The cells were passaged every 2 days at 1:3. The supernatant of the culture media was collected for the determination of extracellular survivin and P-gp production by ELISA (R&D Systems, Minneapolis, Minn., United States of America; MyBiosource, San Diego, Calif., United States of America) following manufacture instructions. The cells were lysed, and the Bcl-2 amount in the lysate was quantified by ELISA (R&D Systems, Minneapolis, Minn., united States of America). As shown in FIG. 6, no gene silencing effect was observed for LIPOFECTAMINE® RNAiMAX/siRNAs after 1 day. However, NCP-1/pooled siRNAs mediated effective gene knockdown up to 4 days, which, without being bound to any particular theory of operation, might be attributed to the preferable balance between siRNA protection and release of NCP-1/siRNAs.

1.7. In Vitro Cytotoxicity:

ES-2, OVCAR-3, SKOV-3, A2780, and A2780/CDDP cells were seeded at 5000 cells per well in 96-well plates and further cultured for 24 h. The culture media were replaced by 100 µL of fresh culture media containing 10% FBS. Cisplatin solution, NCP-1, NCP-1/siRNA containing pooled siRNAs, NCP-1/siRNA containing single siRNA, and Zn control/siRNA containing pooled siRNAs were added to the cells at different cisplatin or siRNA dose. Following incubation for 24 h, the cell viability was determined by (3-(4, 5-dimethylthiazol-2-yl)-5-(3-carboxymethoxyphenyl)-2-(4-sulfophenyl)-2H-tetrazolium) (MTS) assay (Promega Corporation, Madison, Wis., United States of America) according to the manufacturer's instructions. The concentrations of cisplatin and siRNA required to inhibit cell growth by 50% ($IC_{50}$ values) were calculated. By co-delivery of pooled siRNAs targeting multiple MDR genes and cisplatin, all three ovarian cancer cells resistant to cisplatin could be re-sensitized, as evidenced by the dramatically decreased cisplatin $IC_{50}$ compared to either free cisplatin or NCP-1 (Table 3). In ES-2, OVCAR-3, SKOV-3, and A2780/CDDP cells, the cisplatin $IC_{50}$ of NCP-1/pooled siRNAs showed a 102-, 7-, 140-, and 16-fold decrease compared to NCP-1, respectively. NCP-1/individual siRNA treatment was only slightly more potent than NCP-1 with the exception of NCP-1/sisurvivin on SKOV-3 cells (with a 21-fold decrease in $IC_{50}$ when compared to NCP-1); the $IC_{50}$ values for NCP-1/individual siRNA samples were only up to 2.6 times lower than that of NCP-1. Even the $IC_{50}$ of NCP-1/sisurvivin on SKOV-3 cells is 6.5 times higher than that of NCP-1/siRNAs. These results indicate that NCP-1/siRNAs are much more potent than NCP-1/individual siRNA, consistent with the more effective gene knockdown as discussed earlier. In cisplatin-sensitive A2780 cells, free cisplatin, NCP-1, and NCP-1/siRNAs evoked similar cytotoxicity (Table 3). The cytotoxicity of Zn control/siRNAs at the siRNA doses corresponding to cisplatin $IC_{50}$ values was also evaluated. No obvious differences were observed between the cell viability of Zn control/siRNAs and control (88.3±2.1%, 89.4±3.1%, 94.2±5.6%, 102.9±4.5%, and 89.4±10.2% for ES-2, OVCAR-3, SKOV-3, A2780, and A2780/CDDP, respectively), indicating that the drastically elevated anticancer efficacy of NCP-1/siRNAs results from the synergy between gene regulation by pooled siRNAs and chemotherapeutic effects of cisplatin.

TABLE 3

Cisplatin $IC_{50}$ (μM) in ES-2, OVCAR-3, SKOV-3, A2780, and A2780/CDDP cells after a 72 h incubation.

|  | ES-2 | OVCAR-3 | SKOV-3 | A2780 | A2780/CDDP |
|---|---|---|---|---|---|
| Free cisplatin | 37.6 ± 1.9 | 44.4 ± 3.2 | 59.5 ± 1.2 | 4.4 ± 1.0 | 24.0 ± 3.1 |
| NCP-1 | 37.9 ± 0.4 | 50.7 ± 0.9 | 56.0 ± 2.2 | 3.3 ± 0.4 | 23.7 ± 5.6 |
| NCP-1/siBcl-2 | 25.4 ± 1.2 | 28.8 ± 2.1 | 25.9 ± 0.6 | — | — |
| NCP-1/siP-gp | 14.6 ± 1.1 | 39.2 ± 1.1 | 44.4 ± 3.4 | — | — |
| NCP-1/sisurvivin | 31.8 ± 2.6 | 45.6 ± 2.1 | 2.6 ± 0.6 | — | — |
| NCP-1/siRNAs | 0.4 ± 0.1 | 6.8 ± 1.1 | 0.4 ± 0.1 | 3.5 ± 0.3 | 1.5 ± 0.4 |

1.8. DNA Ladder:

ES-2, OVCAR-3, and SKOV-3 cells were seeded at $1 \times 10^6$ cells per well in 6-well plates and further cultured for 24 h. The culture media were replaced by 2 mL of fresh culture media containing 10% FBS. NCP-1 and NCP-1/siRNA containing pooled siRNAs were added to the cells at cisplatin concentration of $IC_{80}$. Following incubation for 24 h, total DNA of cancer cells was extracted using DNA ladder isolation kit (Sigma-Aldrich Corporation, St. Louis, Mo., United States of America) according to the manufacturer's instructions and examined for DNA fragmentation on a 2% (w/v) agarose gel electrophoresis at 35 V for 5 h. The presence of the characteristic DNA ladder in the NCP-1/pooled siRNAs group rather than NCP-1 groups indicated that co-delivery of cisplatin and pooled siRNAs could induce cell apoptosis in cisplatin-resistant cells by silencing the MDR gene expression.

1.9. Cell Apoptosis by Annexin V Staining:

Coverslips put in 6-well plates were seeded with ES-2, OVCAR-3, and SKOV-3 cells at the density of $1 \times 10^6$ cells per well. The cells were incubated at 37° C. and 5% $CO_2$ for 24 h prior to nanoparticle treatment. TAMRA-siRNA loaded NCP-1/siRNA were incubated with cells at 37° C. and 5% $CO_2$ for 24 h. Then, the cells were washed with PBS, fixed with iced 4% paraformaldehyde, and stained with 10 μg/mL of DAPI and Alexa Fluor 488 conjugated Annexin V (Invitrogen, Carlsbad, Calif., United States of America) according to the manufacturer's instructions. The cells were observed using confocal laser scanning microscopy (CLSM, Zeiss LSM710, Jena, Germany) at excitation wavelength of 405 nm, 488 nm, and 546 nm to visualize nuclei (blue fluorescence), cell apoptosis (green fluorescence) and nanoparticle internalization (red fluorescence), respectively. All three ovarian cancer cells treated with NCP-1/pooled siRNAs for 24 h were able to effectively take up siRNA, suggesting the nanoparticles successfully induced enhanced cancer cell apoptosis.

Figure 4:
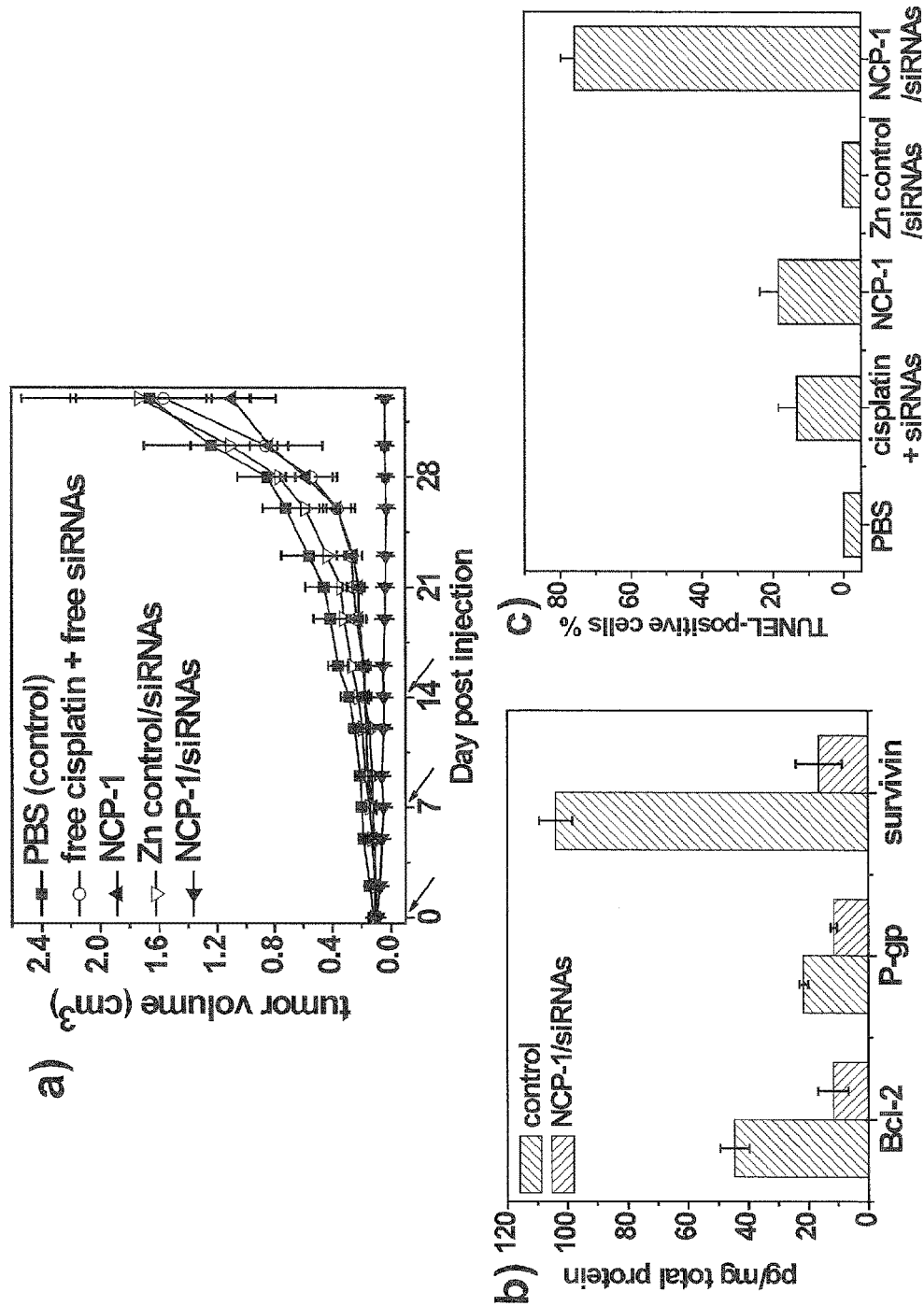
FIG. 4 is a set of graphs showing the in vivo anticancer efficacy of nanoscale coordination polymer nanoparticles carrying cisplatin and a combination of three siRNAs including siRNAs targeting Bcl-2, P-gp, and survivin on a subcutaneous xenograft mouse model of SKOV-3 via intratumoral injection at a cisplatin dose of 1 mg/kg and a siRNA dose of 0.25 mg/kg once a week for a total of three injections. (a) tumor growth curve. (b) Gene expression in tumor tissues as indicated by protein levels. (c) apoptotic cell percent in tumor sites by quantitative TUNEL assay.

1.10. In Vivo Anticancer Efficacy:

Tumor bearing mice were established by subcutaneous inoculation of SKOV-3 cell suspension ($5 \times 10^6$ cells per mouse) into the right flank region of 8-week athymic female nude mice. After the tumor volume reached approximately 100 mm³, the mice were randomly divided into 5 groups (n=6) and intratumorally injected with PBS, free cisplatin plus free pooled siRNA solution, NCP-1, Zn control/siRNAs, and NCP-1/siRNAs at equivalent cisplatin dose of 1 mg/kg and siRNA dose of 0.25 mg/kg once every week (total three injections). Tumor volumes and body weights were monitored three times every week. Tumor volumes were calculated as follows: (width²×length)/2 (Table 4). See also FIG. 4(a).

TABLE 4

Tumor growth curve (cm³)

| | PBS | Free cis + siRNA | NCP-1 | Zn control/siRNAs | NCP-1/siRNAs |
|---|---|---|---|---|---|
| Day 0 | 0.12 ± 0.02 | 0.11 ± 0.01 | 0.10 ± 0.01 | 0.11 ± 0.01 | 0.10 ± 0.01 |
| Day 2 | 0.14 ± 0.03 | 0.10 ± 0.02 | 0.10 ± 0.01 | 0.11 ± 0.01 | 0.08 ± 0.01 |
| Day 5 | 0.19 ± 0.03 | 0.11 ± 0.02 | 0.12 ± 0.03 | 0.13 ± 0.01 | 0.06 ± 0.10 |
| Day 7 | 0.20 ± 0.02 | 0.12 ± 0.02 | 0.13 ± 0.02 | 0.14 ± 0.03 | 0.05 ± 0.01 |
| Day 9 | 0.21 ± 0.03 | 0.13 ± 0.02 | 0.16 ± 0.02 | 0.17 ± 0.01 | 0.06 ± 0.01 |
| Day 12 | 0.25 ± 0.04 | 0.14 ± 0.02 | 0.17 ± 0.02 | 0.19 ± 0.03 | 0.05 ± 0.01 |
| Day 14 | 0.28 ± 0.06 | 0.18 ± 0.03 | 0.17 ± 0.04 | 0.22 ± 0.04 | 0.05 ± 0.01 |
| Day 16 | 0.36 ± 0.07 | 0.18 ± 0.02 | 0.18 ± 0.04 | 0.26 ± 0.03 | 0.05 ± 0.01 |
| Day 19 | 0.41 ± 0.11 | 0.23 ± 0.04 | 0.22 ± 0.06 | 0.32 ± 0.07 | 0.04 ± 0.01 |
| Day 21 | 0.45 ± 0.13 | 0.25 ± 0.05 | 0.22 ± 0.04 | 0.34 ± 0.08 | 0.03 ± 0.01 |
| Day 23 | 0.56 ± 0.19 | 0.26 ± 0.03 | 0.25 ± 0.07 | 0.43 ± 0.13 | 0.03 ± 0.01 |
| Day 26 | 0.72 ± 0.16 | 0.36 ± 0.12 | 0.36 ± 0.10 | 0.58 ± 0.15 | 0.03 ± 0.01 |
| Day 28 | 0.85 ± 0.21 | 0.54 ± 0.17 | 0.58 ± 0.18 | 0.77 ± 0.12 | 0.03 ± 0.02 |
| Day 30 | 1.24 ± 0.46 | 0.86 ± 0.40 | 0.83 ± 0.13 | 1.11 ± 0.27 | 0.03 ± 0.02 |
| Day 33 | 1.66 ± 0.87 | 1.57 ± 0.59 | 1.10 ± 0.14 | 1.73 ± 0.46 | 0.03 ± 0.02 |

No antitumor efficacy was observed for free cisplatin (1 mg/kg dose) plus free pooled siRNAs (0.25 mg/kg dose), NCP-1 (1 mg/kg dose), and Zn control/siRNAs (0.25 mg/kg dose), of which the P values were 0.8311, 0.1502, 0.8594 compared to control by two-tail T-test, respectively (Table 5).

TABLE 5

| tumor weight (g) | |
|---|---|
| Control | 566.3 ± 226.3 |
| Cisplatin + siRNAs | 581.6 ± 262.6 |
| NCP-1 | 350.4 ± 85.7 |
| Zn Control/siRNAs | 639.1 ± 305.9 |
| NCP-1/siRNAs | 16.5 ± 10.6 |

One hundred micrograms of tumor was homogenized with radioimmunoprecipitation assay buffer (RIPA buffer) and then centrifugated at 12,000 rpm for 15 min at 4° C. The amounts of Bcl-2, P-gp, and survivin in the supernatant were measured by ELISA and normalized with total protein content determined using the BCA kit. Another 100 μg of tumor was homogenized in liquid nitrogen, and the RNA in the tumor tissues was extracted with the Trizol reagent and the intracellular Bcl-2, survivin, and P-gp mRNA levels were thereafter monitored by Realtime-PCR. The Bcl-2, P-gp, and survivin protein production of tumors treated with NCP-1/siRNAs were down-regulated by 74%, 48%, and 84%, respectively, in comparison to the control. See FIG. 4(b). The significant knockdown of Bcl-2, P-gp, and survivin in the tumor site presumably sensitized the tumor cells towards cisplatin treatment, leading to the much enhanced antitumor effect by the co-delivery of cisplatin and siRNAs.

TdT-mediated dUTP nick end labeling (TUNEL) reaction was performed on 5-μm frozen tumor sections using DNA Fragmentation Detection Kit (Life Technologies, Carlsbad, Calif., United States of America) according to the manufacturer's instructions and observed CLSM. DNA fragment in apoptotic cells was stained with fluorescein-conjugated deoxynucleotides (green) and the nuclei were stained with DAPI (10 μg/mL). The percentage of apoptotic cells was determined by the number ratio of TUNEL-positive cells/total cells by Image J. The TUNEL assay showed that the fluorescence intensity of DNA fragmentation and the relative percentage of apoptotic cells in the NCP-1/siRNAs group were higher than those in the other groups, indicating their superior anticancer efficacy (Table 6). See also, FIG. 4(c).

TABLE 6

| TUNEL positive cells % | |
|---|---|
| PBS | 0 |
| Cisplatin + siRNAs | 13.5 ± 5.1 |
| NCP-1 | 18.5 ± 5.3 |
| Zn Control/siRNAs | 0 |
| NCP-1/siRNAs | 75.8 ± 4.0 |

1.11. NCP/1-Thiolated SiRNA:

Thiolated siRNAs (Bcl-2 siRNA and survivin siRNA) were conjugated to DSPE-succinimidyl 3(2-pyridyldithio) propionate (SPDP) to afford DSPE-siRNA conjugates. DOPA-capped NCP-1 nanoparticles were coated with DOPC, cholesterol, 20 mol % DSPE-PEG2k, and DSPE-siRNA at a cisplatin to siRNA weight ratio of 4:1.

The Z-average size, PDI, and zeta potential of NCP-1/thiolated siRNAs are 105.3±6.2 nm, 0.112±0.004, and −4.8±1.3 mV, respectively, by DLS measurement. The siRNA encapsulation efficiency and loading were determined to be 77.84% and 4.86 wt %, respectively, by Quant-iT RiboGreen RNA kit. TEM was used to observe the morphology of NCP-1/siRNAs, which were spherical and mono-dispersed in PBS.

The siRNA release of NCP-1/siRNAs was evaluated in PBS supplemented with 4.5 μM GSH (extracellular environment) or 10 mM GSH (intracellular environment). siRNA release was slow in PBS without GSH and significantly promoted in PBS containing 10 mM GSH. See FIG. 5(a). Upon entering the cells, the disulfide bond of DSPE-siRNA was rapidly cleaved by the reducing agent which led to the promoted siRNA release.

Figure 5:
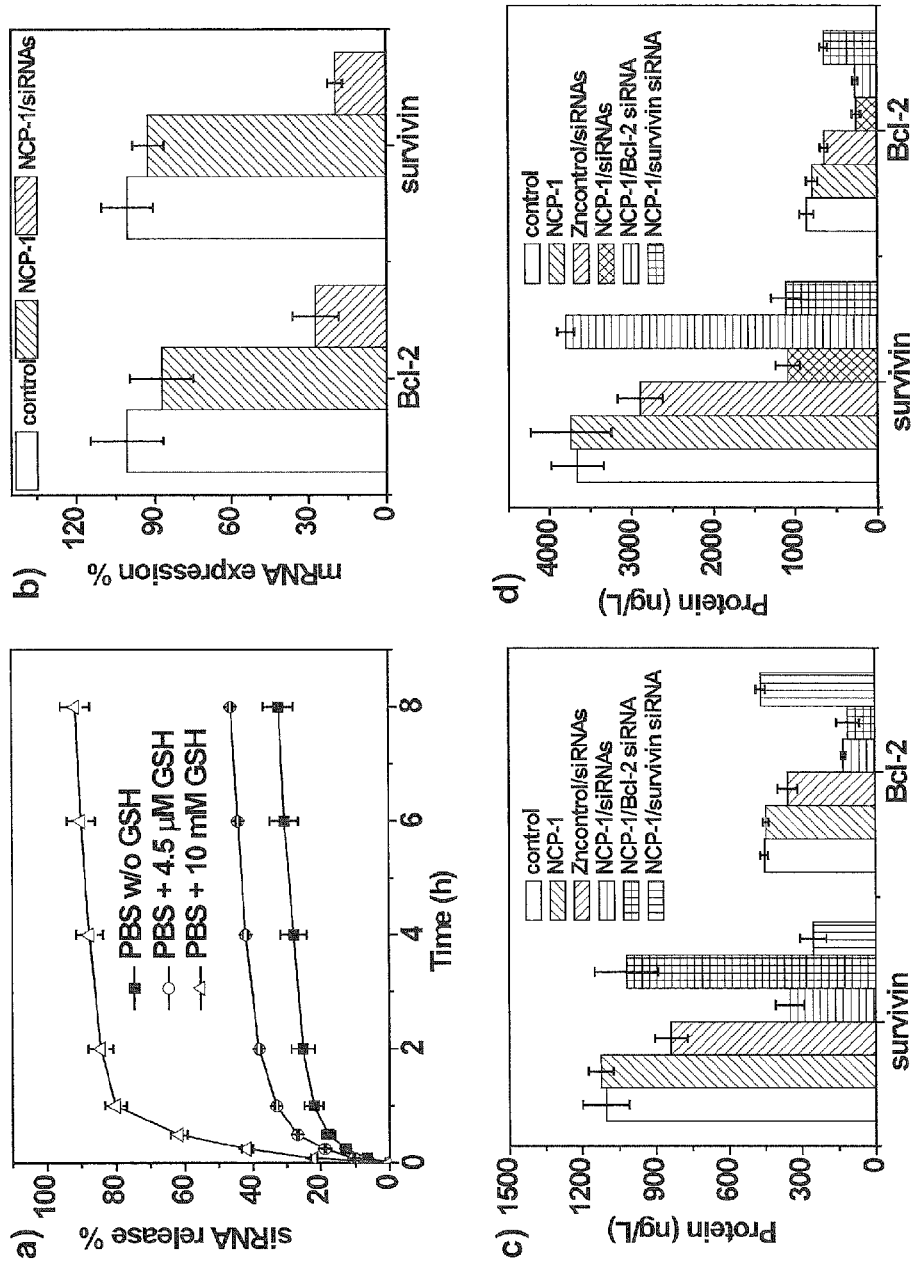
FIG. 5 is a set of graphs showing (a) siRNA release in a reducing environment, through addition of glutathione (GSH), and (b)-(d) gene silencing mediated by nanoscale coordination polymer nanoparticles carrying cisplatin and thiol siRNAs targeting Bcl-2 and survivin.

After a 24-h transfection, mRNA expression and protein production of Bcl-2 and survivin were measured in A2780/CDDP cells transfected with NCP/siRNAs at a siRNA dose of 6 nM. mRNA expression and protein production of Bcl-2 and survivin were determined by realtime-PCR and ELISA, respectively. NCP-1 treatment exerted unappreciable effects on the mRNA expression. See FIG. 5(b). Protein production of Bcl-2 and survivin in SKOV-3 cells is shown in FIG. 5(c), while protein production of Bcl-2 and survivin in A2780/CDDP cells is shown in FIG. 5(d). Zncontrol/siRNAs failed to mediate potent gene silencing, which might be due to the lack of efficient endosomal escape. NCP-1/siRNAs significantly down-regulated the expression of Bcl-2 and survivin.

A2780/CDDP cells were i.p. injected into female athymic nude mice (6-week) at a concentration of 107 cells per ml (200 μL per injection). Mice were treated with PBS, NCP-1 (0.5 mg cisplatin/kg), and NCP-1/thiolated siRNAs (0.5 mg cisplatin/kg, 0.125 mg siRNA/kg) via i.p. injection every three days beginning on Day 6 following tumor cell injection for a total of three injections. The body weight of the mice was measured on Day 0 and monitored daily after the first drug administration. The mice were sacrificed when severe health problems were noticed.

Figure 7:
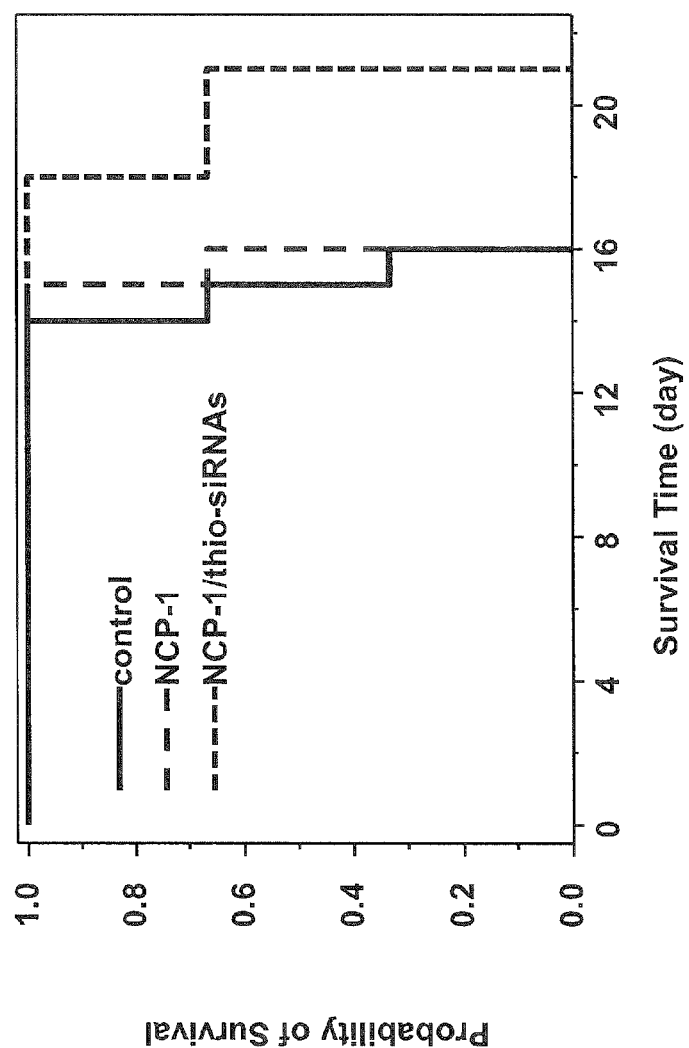
FIG. 7 is a graph showing survival curves of mice with an intraperitoneal (i.p.) orthotopic mouse model of A2780/

NCP-1/siRNAs significantly increase the survival time compared with PBS (control) and NCP-1 (NCP-1/siRNAs vs. control, P=0.01472 by one-way ANOVA). NCP-1 showed no survival benefit over PBS (NCP-1 vs. control, P=0.3739 by one-way ANOVA). See FIG. 7.

Example 2

Chemotherapeutics Sequentially Loaded into Porous Nanoparticle Coordination Polymers Scheme 3. Synthesis of the cisplatin prodrug cis, cis, trans-[Pt(NH$_3$)$_2$Cl$_2$(OEt)(OCOCH$_2$CH$_2$COOH)].

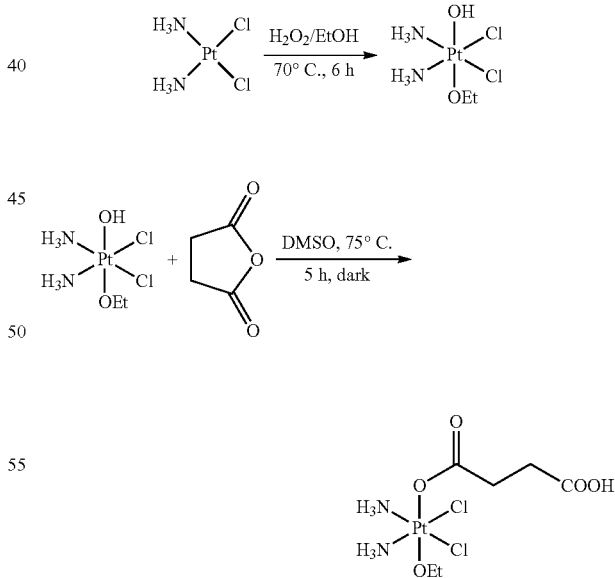

The cisplatin prodrug cis, cis, trans-[Pt(NH$_3$)$_2$Cl$_2$(OEt) (OCOCH$_2$CH$_2$COOH)] was prepared as shown in Scheme 3. More particularly, cisplatin was reacted with hydrogen peroxide in ethanol to provide an intermediate having one hydroxyl and one ethoxy ligand. Then the intermediate was reacted with succinic anhydride to provide the prodrug.

Scheme 4. Synthesis of amino-triphenyldicarboxylic acid (amino-TPDC) ligand.

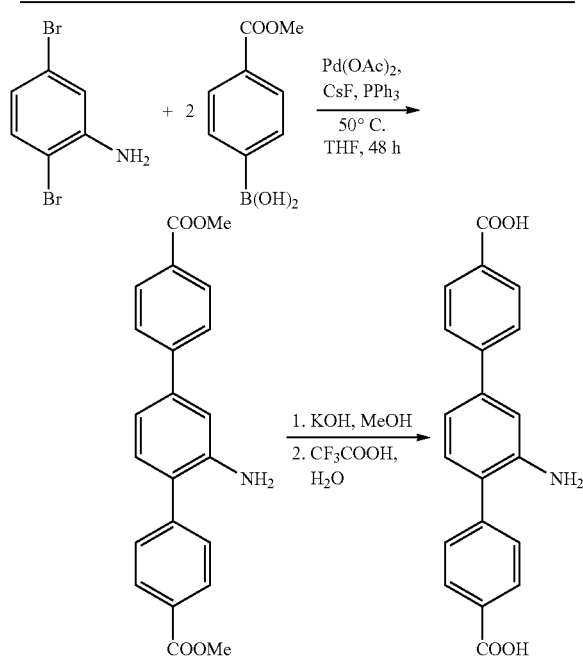

The NCP based on $Zr_6(\mu_3-O)_4(\mu_3-OH)_4$ secondary building units (SBUs) and dicarboxylate bridging ligands are highly porous and stable in aqueous environment due to the high connectivity of the SBUs and the strong interaction between zirconium and oxygen. This material is termed UiO as the original family was discovered by Lillerud and coworkers at the University of Oslo (UiO). The UiO NCP with amino-triphenyldicarboxylic acid (amino-TPDC) bridging ligand (prepared as shown above in Scheme 4) was synthesized by heating a DMF solution of $ZrCl_4$ and amino-TPDC at 80° C. for 5 days. The as-synthesized UiO material is crystalline by powder X-ray diffraction (PXRD) and exhibits hexagonal plate-like morphology by transmission electron microscopy (TEM) images. High resolution TEM images showed that the distances between the lattice fringes are 1.83 nm corresponding to the predicted d(111) value of 1.85 nm. The fast Fourier transform pattern (FFT) proved a 3-fold symmetry along the observation direction. The cisplatin prodrug, cis, cis, trans-[Pt(NH$_3$)$_2$Cl$_2$(OEt)(OCOCH$_2$CH$_2$COOH)] (Scheme 3, above), was loaded into the pores of UiO via amide bonds to form UiO-Cis. NMR spectroscopy confirmed the covalent attachment of cisplatin prodrug, whereas PXRD indicated that UiO-Cis is isostructural to UiO-68. The cisplatin loading in UiO-Cis was determined to be 12.3±1.2 wt % by ICP-MS.

siRNA was loaded onto UiO-Cis by simply mixing UiO-Cis and siRNA in water at a cisplatin:siRNA mass ratio of 4.5:1 to form siRNA/UiO-Cis. Without wishing to be bound by theory, siRNA is believed to bind to the NCP surface via multiple coordination bonds between phosphate residues on the siRNA backbone and vacant Zr sites on the NMOF surface. The siRNA loading did not change the morphology of NMOFs as shown by TEM. Dynamic light scattering (DLS) measurements gave average diameters of 98±11 nm (PDI=0.070), 103±17 nm (PDI=0.124), and 128±3 nm (PDI=0.116) for UiO, UiO-Cis and siRNA/UiO-Cis, respectively. The increase in the DLS diameter for siRNA/UiO-Cis is consistent with the presence of siRNA on the UiO surface. The siRNA binding capabilities of NMOFs were confirmed by gel electrophoresis, which showed that NMOFs could efficiently "capture" siRNA on the surface as evidenced by the complete retardation of siRNA band migration for siRNA/UiO-Cis. The siRNA loading efficiency (LE) was also quantitatively examined by fluorimetry. Fluorescently labeled siRNA (TAMRA-siRNA) was used to form siRNA/UiO-Cis, and the LE was determined to be as high as 81.6±0.6%. Without wishing to be bound by theory, it is thought that as a result of steric hindrance on surfaces, NMOFs protected siRNA from RNase degradation: a siRNA band was clearly visible upon incubating siRNA/UiO-Cis in serum for up to 4 h while the naked siRNA was completely degraded under the same condition. Interestingly, siRNA "coating" on the NMOF surface significantly retarded protein adsorption, suggesting a possible stabilization of NMOFs via siRNA binding.

High siRNA uptake levels and successful endosomal escape are two prerequisites for efficient siRNA-mediated gene silencing. Compared to the naked siRNA solution, siRNA uptake amounts of siRNA/UiO-Cis were significantly increased, indicating that the NCP facilitates the siRNA internalization via endocytosis pathways. The siRNA uptake was also directly observed by confocal laser scanning microscopy (CLSM). Large amounts of siRNA were located in the cytoplasms of SKOV-3 cells. In addition, zirconium phosphate has extremely low solubility ($K_{sp}=10^{-134}$), which demonstrates a high affinity of Zr(IV) to phosphate ions. Phosphate buffer saline (PBS) containing relatively high phosphate group concentration (2 mM) significantly promoted siRNA release compared to water. It is reasonable to expect that siRNA could dissociate from UiO-Cis, and LAO-Cis could decompose after internalization and entrapment in endosomes due to the presence of much higher concentrations of endogenous phosphate ions in endosomes than in extracellular environments. The dissociated Zr ions can bind to the negatively charged and phosphate-group-enriched endosome membrane to disrupt the endosome structure and facilitate the release of entrapped siRNAs. This hypothesis was supported by CLSM studies. After a 2 hour incubation, siRNA in the siRNA/UiO-Cis was able to escape from the endo/lysosome entrapment, as demonstrated by the absence of colocalization of stained siRNA and fluorescently labeled lysosomes in the cytoplasm.

The transfection efficiency mediated by siRNA/UiO-Cis in SKOV-3 cells was evaluated. siRNA/UiO-Cis evoked potent gene silencing in SKOV-3 cells at an siRNA concentration of 0.4 μg/mL (30 nM) as determined by ELISA. Interestingly, by using one-third of the siRNA dose for the pooled siRNAs/UiO-Cis compared to single siRNA/UiO-Cis, equivalent gene silencing efficiencies were achieved, which could be attributed to the synergistic silencing effects of pooled siRNAs. In comparison, none of the free siRNA solution, UiO-Cis, and UiO was capable to down regulate the gene expression.

To examine whether the efficient and simultaneous knockdown of three MDR-relevant genes including survivin, Bcl-2, and P-gp could effectively reverse the cisplatin resistance in ovarian cancer cells, the cytotoxicity of free cisplatin, UiO-Cis, and siRNA/UiO-Cis was assessed by 3-(4,5-dimethylthiazol-2-yl)-5-(3-carboxymethoxy-phenyl)-2-(4-sulfophenyl)-2H-tetrazolium (MTS) assay. The cisplatin $IC_{50}$ values of free cisplatin, UiO-Cis, and siRNA/UiO-Cis were calculated to be 48.5±4.3, 47.8±5.2, and 4.2±2.0 μM, respectively. No cytotoxicity (cell viability of 96.2±3.4%) was observed in SKOV-3 cells when treated with siRNA/

UiO at 12 times higher siRNA dose. By co-delivering pooled siRNAs and cisplatin utilizing NMOFs, the $IC_{50}$ value dramatically decreased (by nearly 12 fold) compared to free cisplatin and UiO-Cis. This result suggested that the cisplatin-resistant ovarian cancer cells could be re-sensitized after being transfected with siRNA/UiO-Cis, and the synergistic effects of siRNA and cisplatin significantly enhanced the in vitro chemotherapeutic efficacy. The cytotoxicity of blank UiO was also evaluated at UiO dose of 0.5 mg/mL (at 50 times higher UiO dose than siRNA/UiO-Cis at $IC_{50}$). Cell viability was determined to be 98.1±5.4%, suggesting a lack of toxicity for UiO.

DNA ladder and Annexin V conjugate staining assays were carried out in order to demonstrate that the enhanced cytotoxicity of siRNA/UiO-Cis was caused by cell apoptosis rather than necrosis. No DNA fragmentation was detectable in the control, UiO-Cis, and free cisplatin groups. Cells treated with siRNA/UiO-Cis displayed characteristic DNA fragmentation or laddering, demonstrating that the cytotoxicity induced by siRNA/UiO-Cis was associated with apoptosis. Annexin V conjugate staining provided further evidence to the apoptosis induced by siRNA/UiO-Cis. siRNA loaded in the NMOFs were efficiently internalized into the cytoplasm after a 24-h incubation to trigger MDR-relevant gene silencing. Annexin V conjugate was clearly visible in cells treated with siRNA/UiO-Cis but not in cells treated with siRNA/UiO (pooled siRNAs alone) or UiO-Cis (cisplatin alone). This result indicates that co-delivery of cisplatin and pooled siRNAs could induce cell apoptosis in cisplatin-resistant cells by combining the synergistic effects of down-regulating the expressions of MDR-relevant genes and chemotherapeutics.

Example 3

Materials and Methods for Nanoparticle Coordination Polymers with Photosensitizers and Chemotherapeutics 3.1. Materials, Cell Lines, and Animals:

All of the starting materials were purchased from Sigma-Aldrich Corporation (St. Louis, Mo., United States of America) and Fisher (Thermo Fisher Scientific, Waltham, Mass., United States of America), unless otherwise noted, and used without further purification. 1,2-dioleoyl-sn-glycero-3-phosphate (DOPA), 1,2-Distearoyl-sn-glycero-3-phosphocholine (DSPC), cholesterol, and 1,2-distearoyl-sn-glycero-3-phosphoethanolamine-N-[amino(polyethylene glycol)$_{2000}$] (DSPE-PEG2k) were purchased from Avanti Polar Lipids (Alabaster, Ala., United States of America).

Human head and neck cancer cell lines HNSCC135 (cisplatin-sensitive), SCC61 (cisplatin-sensitive), JSQ3 (cisplatin-resistant), and SQ20B (cisplatin-resistant) were kindly provided by Dr. Stephen J. Kron (Department of Molecular Genetics and Cell Biology, The University of Chicago, Chicago, United States of America). These cell lines were cultured in DME/F12 (1:1) medium (Gibco, Grand Island, N.Y., United States of America) containing 20% fetal bovine serum (FBS, Hyclone, Logan, Utah, United States of America). Murine colon adenocarcinoma cell CT26 was purchased from the American Type Culture Collection (Rockville, Md., United States of America) and cultured in RPMI 1640 medium (Gibco, Grand Island, N.Y., United States of America) supplemented with 10% FBS. Athymic female nude mice (6 weeks, 20-22 g) were provided by Harlan Laboratories, Inc. (Indianapolis, Ind., United States of America).

3.2. Cellular Uptake Dynamics of NCP-1-Pyrolipid in Head and Neck Cancer Cells:

The cellular uptake of NCP-1 particles in SQ20B cells was quantified by ICP-MS. SQ20B cells were seeded on 6-well plates at $5\times10^5$ cells/well and incubated for 24 h. NCP-1-pyrolipid, NCP-1, free cisplatin, or porphysome was added to the cells at a cisplatin dose of 5 µM or pyrolipid dose of 1.5 µM, respectively. After incubating for 1, 2, 4, and 24 h, SQ20B cells were collected, washed with PBS three times, and counted with a hemocytometer. The cells were centrifuged at 3,000 rpm for 5 min and the cell pellet was digested with 500 µL of concentrated nitric acid. After 24 h, the digestion was diluted with water and subjected to ICP-MS to determine the Pt concentration. Results were expressed as the amount of cisplatin (ng) per $10^5$ cells. The amount of pyrolipid being taken up by the cells was quantified with a spectrofluorophotometer (RF-5301 PC, Shimadzu, Kyoto, Japan). After incubating with NCP-1-pyrolipid for 1, 2, 4, and 24 h, SQ20B cells were washed with PBS three times, counted with a hemocytometer, and lysed with 0.5% SDS (pH 8.0). The fluorescence intensity of pyrolipid was determined by fluorimetry ($\lambda_{ex}$=427 nm, $\lambda_{em}$=675 nm). Results were expressed as the amount of pyrolipid (ng) per $10^5$ cells.

The efflux of cisplatin and pyrolipid in SQ20B cells was quantified as follows. SQ20B cells were seeded on 6-well plates at $5\times10^5$ cells/well and incubated for 24 h. NCP-1-pyrolipid, NCP-1, free cisplatin, or porphysome was added to the cells at a cisplatin dose of 5 µM or pyrolipid dose of 1.5 µM, respectively. After incubating for 4 h, the culture medium was discarded and the cells were washed with PBS three times. Two milliliter of fresh culture medium was added to each well and the cells were further incubated at 5% $CO_2$ and 37° C. After incubating for 1, 2, 4, and 24 h, the culture medium was collected and subjected to ICP-MS to determine the Pt concentration for the quantification of efflux of cisplatin. The pyrolipid amount in the culture medium was quantified by fluorimetry after adding 0.5% Triton X-100 to determine the efflux of pyrolipid ($\lambda_{ex}$=427 nm, $\lambda_{em}$=675 nm). Results were expressed as the percent of the amount of cisplatin or pyrolipid being effluxed compared to the 4-h cellular uptake amount.

The internalization and intracellular distribution of pyrolipid was directly observed under CLSM. NCP-1-pyrolipid nanoparticles were incubated with SQ20B cells for 1 h, 2 h, 4 h and 24 h, respectively. The cells were washed with PBS three times, fixed with 4% paraformaldehyde, and observed under CLSM (Olympus FV1000) using a 405 nm laser.

3.3. Cytotoxicity of NCP-1-Pyrolipid in Head and Neck Cancer Cells:

The cytotoxicity of NCP-1-pyrolipid was tested in four head and neck cancer cell lines including cisplatin-resistant SQ20B and JSQ3 cells and cisplatin-sensitive HNSCC135 and SCC61 cells. The cells were seeded on 96-well plates at 2500 cells/well. After incubating for 24 h, the cells were treated with NCP-1-pyrolipid, porphysome, NCP-1, and free cisplatin at various cisplatin concentrations or pyrolipid concentrations. After a 24-h incubation, the cells were irradiated with LED light (670 nm) at 60 mW/cm² for 15 min (equals to 54 J/cm²). The cells without irradiation treatment served as controls. The cells were further incubated for 48 h. The cell viability was detected by (3-(4,5-dimethylthiazol-2-yl)-5-(3-carboxymethoxyphenyl)-2-(4-sulfophenyl)-2H-tetrazolium) (MTS) assay (Promega, Madison, Wis., United States of America) and the $IC_{50}$ values were calculated accordingly.

3.4. Flow Cytometry:

SQ20B cells were seeded at 1×10⁶ cells per well in 6-well plates and further cultured for 24 h. The culture media were replaced by 2 mL of fresh culture media containing 10% FBS. Free cisplatin, NCP-1, NCP-1-pyrolipid, Zn Control-pyrolipid, porphysome were added to the cells, respectively, at a cisplatin concentration of 5 µM or equivalent pyrolipid concentration of 1.5 µg/mL. Cells incubated with PBS served as control. After a 24 h 60 mW/cm² for 15 min incubation, the cells were irradiated with light emitting diode (LED) light (670 nm) at 60 mW/cm² for 15 min (equals to 54 J/cm²). Following a further incubation of 48 h, the floating and adherent cells were collected and stained with Alexa Fluor 488 Annexin V/dead cell apoptosis kit with Alexa Fluor 488 annexin V and PI (Invitrogen, Carlsbad, Calif., United States of America) according to manufacturer's instructions. The apoptosis and necrosis was examined on a flow cytometer (LSRII Blue, Becton, Dickinson, and Company, Franklin Lakes, N.J., United States of America).

3.5. Pharmacokinetics and Tissue Distributions:

Mice were subcutaneously injected in the right flank with 1 million CT26 cells and tumors were allowed to grow until 100 mm³ before they received intravenous administration of NCP-1-pyrolipid at a cisplatin dose of 3 mg/kg. Animals were sacrificed (3 per time-point) at 5 min, 1 h, 3 h, 8 h, 24 h, and 48 h after drug dose. After collecting the blood, liver, lung, spleen, kidney, and bladder were harvested. Organs and blood were digested in concentrated nitric acid for 24 h and the Pt concentrations were analyzed by ICP-MS. The pyrolipid amounts in the blood collected at 5 min, 1 h, 3 h, 8 h, 24 h, and 48 h were determined. Briefly, the blood was centrifuged at 3,000 rpm for 10 min to separate plasma. Methanol and 0.25% Triton X-100 was added to the plasma for extracting the pyrolipid and preventing aggregation, respectively. The pyrolipid concentrations were determined by UV-vis.

3.6. In Vivo Anticancer Efficacy:

The PDT efficacy of NCP-1-pyrolipid was investigated using the SQ20B subcutaneous xenograft murine model. Tumor bearing mice were established by subcutaneous inoculation of SQ20B cell suspension (5×10⁶ cells per mouse) into the right flank region of 6-week athymic female nude mice. Five groups were included for comparison: PBS with irradiation as control; NCP-1 with irradiation; porphysome with irradiation; NCP-1-pyrolipid with irradiation; NCP-1-pyrolpid without irradiation. When tumors reached 100 mm³, NCP-1, NCP-1-pyrolipid, and porphysome were i.v. injected to animals at a cisplatin dose of 0.5 mg/kg (corresponding to a pyrolipid dose of 0.5 mg/kg). At 24 h post-injection, mice were anesthetized with 2% (v/v) isoflurane and tumors were irradiated with a 670 nm LED for 30 min. The energy irradiance was measured to be 100 mW/cm², and the total light dose was 180 J/cm². Both injection and PDT were performed once a week for a total of 2 times.

To evaluate the therapeutic efficacy, tumor growth and body weight evolution were monitored. The tumor size was measured with a digital caliper every day. Tumor volumes were calculated as follows: (width²×length)/2. All mice were sacrificed on Day 12, and the excised tumors were photographed and weighed. The tumors were embedded in optimal cutting temperature (OCT) medium, sectioned at 5-µm thickness, and subjected to hematoxylin and eosin (H&E) stain for histopathological analysis and TdT-mediated dUTP nick end labeling (TUNEL, Invitrogen, Carlsbad, Calif., United States of America) assay for quantifying the in vivo apoptosis. Liver, lungs, spleen, and kidneys were also excised after the mice were sacrificed, and then embedded in OCT medium, sectioned at 5-µm thicknes, stained with H&E, and observed for toxicity with light microscopy (Pannoramic Scan Whole Slide Scanner, Perkin Elmer, Waltham, Mass., United States of America). Blood was collected at the endpoint, and the serum TNF-α, IFN-γ, and IL-6 production was determined by ELISA (R&D Systems, Minneapolis, Minn., United States of America).

Example 4

Nanoparticle Coordination Polymers with Photosensitizers and Chemotherapeutics 4.1 Preparation and Characterization of NCP-1-Pyrolipid:

A mixture of $Zn(NO_3)_2$ and a cisplatin prodrug, cis,cis,trans-$[Pt(NH_3)_2Cl_2(OCONHP(O)(OH)_2)_2]$, with 1,2-dioleoyl-sn-glycero-3-phosphate sodium salt (DOPA) in the Triton X-100/1-hexanol/cyclohexane/water reverse microemulsion was vigorously stirred at room temperature for 30 min to afford spherical DOPA-coated NCP-1 particles of 20 nm in diameter by transmission electron microscopy and 54.1 nm in diameter by dynamic light scattering. NCP-1 has a cisplatin loading of 25±2 wt % as determined by inductively coupled plasma-mass spectrometry (ICP-MS).

NCP-1 was coated with pyrolipid and pegylated to afford NCP-1-pyrolipid by stirring a tetrahydrofuran (THF) solution (80 µL) of pyrolipid, cholesterol, 1,2-distearoyl-sn-glycero-3-phosphocholine (DSPC, pyrolipid/cholesterol/DSPC=1:1:2 in molar ratios), 20 mol % DSPE-PEG2k, and DOPA-capped NCP-1 in 500 µL of 30% (v/v) ethanol/water at 60° C. for 1 min. More particularly, pyrolipid coated NCP-1 (NCP-1-pyrolipid) was prepared by adding a THF solution (80 µL) of pyrolipid, cholesterol, DSPC (pyrolipid/cholesterol/DSPC=1:1:2 in molar ratios), 20 mol % DSPE-PEG2k, and DOPA-coated NCP-1 to 500 µL of 30% (v/v) ethanol/water at 60° C. The mixture was stirred at 1700 rpm for 1 min. THF and ethanol were completely evaporated and the NCP-1-pyrolipid solution was allowed to cool down to room temperature. NCP-1-pyrolipid was centrifuged at 13000 rpm for 30 min followed by the removal of the supernatant and re-suspending the particles in phosphate buffered solution (PBS).

NCP-1-pyrolipid contains a self-assembled and asymmetric lipid bilayer, with pyrolipid as a PS for PDT, DSPC as a lipid component to form lipid bilayer, cholesterol as a lipid excipient to order, condense and stabilize the lipid bilayer structure, and DSPE-PEG2k to endow "stealth" and long circulation properties. The THF and ethanol in the nanoparticle suspension was completely evaporated before subsequent use in in vitro and in vivo experiments. ICP-MS (Agilent 7700X, Agilent Technologies, Santa Clara, Calif., United States of America) was utilized to analyze the Pt concentration of NCP-1 to calculate cisplatin loadings. The particle size and Zeta potential of NCP-1-pyrolipid in PBS were determined by Zetasizer (Nano ZS, Malvern, UK). Transmission electron microscopy (TEM, Tecnai Spirit, FEI, Hillsboro, Oreg., United States of America) was used to observe the morphology of NCP-1-pyrolipid. The structural stability of NCP-1-pyrolipid was evaluated by recording the particle size and PDI of nanoparticles incubated in PBS containing 5 mg/mL BSA at 37° C. up to 24 h by DLS.

NCP-1-pyrolipid demonstrated the formation of uniform spherical nanoparticles without aggregation. DLS measurements gave a Z-average diameter, polydispersity index (PDI), and zeta potential of 108.0±0.2 nm, 0.136±0.012, and −2.3 mV for NCP-1-pyrolipid dispersed in phosphate buffered saline (PBS), respectively. The small sizes and near neutral surface charge of NCP-1-pyrolipid suggested their potential in vivo applications. NCP-1-pyrolipid also exhibited favorable structural stability in physiological environment as evidenced by the unaltered particle size and PDI observed by incubating the particles in PBS containing 5 mg/mL BSA up to 24 h.

When dissolved in THF, pyrolipid showed a broad Soret band around 400 nm and a distinct Q-band at 669 nm. DOPA-capped NCP-1 particles had no absorption at 669 nm. After coating on the surface of NCP-1, pyrolipid preserved the Q-band, which was utilized to quantify the pyrolipid coating amount. After lipid coating, NCP-1-pyrolipid was centrifuged and the pyrolipid amounts in both the supernatant and precipitate were determined by UV-vis spectroscopy. About 265.6 μg of pyrolipid was coated on the surface of each mg of NCP-1, corresponding to a pyrolipid to cisplatin weight ratio of ~1:1 (a molar ratio of ~1:3) for NCP-1-pyrolipid.

Porphysome was prepared following the procedure reported by Zheng and coworkers (Jin, C. S., et al., *Adv Healthcare Mater.* 3(8), 1240-1249 (2014); and Lovell, J. F. et al., *Nat Mater.* 10, 324-332 (2011)). The Z-average diameter and PDI of porphysome were determined to be 152.7 nm and 0.150, respectively, by DLS. Porphysome was used as a monotherapy control in the present investigation.

4.2. Photochemistry:

The singlet oxygen sensor green (SOSG) reagent (Life Technologies, Carlsbad, Calif., United States of America) was employed for the detection of singlet oxygen generated by NCP-1-pyrolipid. After lipid coating, NCP-1-pyrolipid were centrifuged at 13000 rpm for 30 min. The supernatant containing free lipid, liposome, and porphysome was discarded and the pellet was re-suspended with PBS. Five microliter of freshly prepared SOSG solution in methanol (5 mM) was mixed with 2 mL of NCP-1-pyrolipid intact in PBS or disrupted with 0.5% Triton X-100. Porphysome with addition of 0.5% Triton X-100 at same pyrolipid concentration as NCP-1-pyrolipid served as a control. Samples were treated with LED with a wavelength of 670 nm and energy irradiance of 120 mW/cm$^2$ for 10 s, 20 s, 30 s, 40 s, 50 s, 100 s, 250 s, 500 s, and 1000 s, and SOSG fluorescence was measured by exciting at 504 nm and emission at 525 nm. There was no pyrolipid fluorescence contribution within this emission window.

Pyrolipid was incorporated into the highly oriented and asymmetric lipid bilayer on the surface of NCP-1-pyrolipid. At sufficiently highly pyrolipid loadings, the fluorescence of pyrolipid will self-quench to influence its photochemistry. Indeed, the fluorescence of pyrolipid in NCP-1-pyrolipid was efficiently quenched (>96% quenching efficiency) when its lipid layer was intact. After addition of Triton X-100, a detergent that can disrupt the lipid bilayer, pyrolipid from the disrupted NCP-1-pyrolipid regained its fluorescence. As the pyrolipid excited state in intact NCP-1-pyrolipid is highly quenched, no energy transfer to triplet oxygen was observed as negligible $^1O_2$ was generated determined by singlet oxygen sensor green (SOSG) reagent (Table 7). In contrast, after the disruption of lipid layer with Triton X-100, NCP-1-pyrolipid efficiently generated $^1O_2$ (Table 7). The $^1O_2$ generation efficiency of NCP-1-pyrolipid with disrupted lipid layer was similar to that of porphysome after adding Triton X-100 at the same pyrolipid concentration (Table 7). Whether the lipid layer is intact or not can therefore be exploited as a "switch" to control the $^1O_2$ generation upon irradiation.

TABLE 7

Oxygen Singlet Generation detected by SOSG. Results shown are relative fluorescence units (RFU).

|  | NCP-1-pyrolipid | NCP-1-pyrolipid + Triton X-100 | Porphysome + Triton X-100 |
| --- | --- | --- | --- |
| 0 s | 10.1621 | 10.1621 | 10.1621 |
| 10 s | 10.1621 | 10.4621 | 11.4321 |
| 20 s | 10.1621 | 18.25335 | 20.3214 |
| 30 s | 10.1621 | 22.4721 | 24.2214 |
| 40 s | 10.1621 | 28.0411 | 29.4232 |
| 50 s | 10.1621 | 33.2011 | 34.2131 |
| 100 s | 10.1621 | 64.1358 | 66.0921 |
| 250 s | 10.1621 | 152.33076 | 155.2412 |
| 500 s | 10.1621 | 302.11055 | 309.234 |
| 1000 s | 10.1621 | 612.33028 | 622.821 |

4.3. Cellular Uptake Dynamics and Intracellular Lipid Dissociation:

The endocytosis pathway of NCP-1-pyrolipid was first explored in human head and neck cancer cell SQ20B. The cells were pre-incubated with a series of uptake inhibitors to block specific internalization pathways, and then incubated with NCP-1-pyrolipid. The uptake of NCP-1-pyrolipid significantly decreased in cells treated with NaN$_3$, chloropromazine, genistein, and Me-β-CD (by 81.2±6.0%, 69.3±1.8%, 59.3±1.7%, and 68.4±1.1%, respectively) but not wortmannin (by 8.4±4.3%), suggesting that the cell uptake is energy-dependent, clathrin/caveolae/lipid raft-mediated endocytosis but not micropinocytosis.

The time-dependent cellular uptake of NCP-1-pyrolipid was evaluated in SQ20B cells with an incubation time of up to 24 h. Free cisplatin, porphysome, and the original NCP-1 (carrying a cisplatin prodrug and coated with 1,2-dioleoyl-sn-glycero-3-phosphocholine (DOPC), cholesterol, and DSPE-PEG2k) served as comparisons. The cellular uptake of NCP-1-pyrolipid was rapid and completed within 1 h, as evidenced by the stable uptake amounts of both cisplatin and pyrolipid over time for up to 24 h. In addition, the uptake amounts of cisplatin and pyrolipid for NCP-1-pyrolipid were almost identical throughout the 24-h experiment (Table 8). Considering the weight ratio of pyrolipid to cisplatin in NCP-1-pyrolipid is ~1:1, without wishing to be bound by theory, it is thought that NCP-1-pyrolipid enter the cells in its intact form. Except for free cisplatin, cellular uptake of cisplatin and pyrolipid remained constant throughout the 24-h experiment. Both cisplatin and pyrolipid uptake amounts of NCP-1-pyrolipid were higher than those of NCP-1 and porphysome.

TABLE 8

Cellular Uptake.

| | | 1 h | 2 h | 4 h | 24 h |
| --- | --- | --- | --- | --- | --- |
| Cisplatin uptake (ng/10$^5$ cells) | NCP-1-pyrolipid | 62.8 ± 4.9 | 61.6 ± 2.4 | 61.0 ± 1.3 | 60.8 ± 1.6 |
| | NCP-1 | 54.6 ± 4.5 | 54.4 ± 1.8 | 51.5 ± 1.1 | 49.8 ± 2.0 |
| | Free cisplatin | 51.7 ± 4.5 | 43.5 ± 1.4 | 38.1 ± 0.8 | 38.5 ± 1.3 |
| Pyrolipid uptake (ng/10$^5$ cells) | NCP-1-pyrolipid | 63.6 ± 0.9 | 64.4 ± 1.3 | 65.4 ± 2.2 | 66.2 ± 2.7 |
| | porphysome | 46.8 ± 0.6 | 47.3 ± 0.9 | 48.1 ± 1.6 | 48.3 ± 2.0 |

In order to understand the cellular uptake dynamics of NCP-1-pyrolipid, the efflux of cisplatin and pyrolipid in different formulations was determined. SQ20B cells were incubated with NCP-1-pyrolipid, NCP-1, free cisplatin, and porphysome for 4 h, and the culture medium was replaced by fresh medium and further incubated for 1, 2, 4, and 24 h. The cisplatin or pyrolipid amounts detected in the culture medium were compared with the 4-h uptake amounts to give the percent efflux (Table 9). NCP-1-pyrolipid showed negligible efflux (<1.5%) of cisplatin and pyrolipid during the 24-h incubation. Porphysome showed as low pyrolipid efflux as NCP-1-pyrolipid. Efflux of free cisplatin increased with time (20.0% at 24 h) and was significantly higher than NCP-1-pyrolipid and NCP-1, which results in the decreased cellular cisplatin concentration over time. Efflux of cisplatin for NCP-1 remained at ~8% over time, and was higher than that of NCP-1-pyrolipid (<1.5%).

TABLE 9

| | | \multicolumn{4}{c|}{Formulation Efflux} |
|---|---|---|---|---|---|
| | | 1 h | 2 h | 4 h | 24 h |
| Cisplatin efflux (%) | NCP-1-pyrolipid | 1.1 ± 0.01 | 0.9 ± 0.1 | 1.0 ± 0.3 | 1.1 ± 0.3 |
| | NCP-1 | 8.2 ± 0.1 | 9.0 ± 1.2 | 7.5 ± 2.0 | 8.5 ± 2.4 |
| | Free cisplatin | 12.0 ± 1.5 | 13.5 ± 0.2 | 18.2 ± 5.1 | 20.0 ± 5.4 |
| Pyrolipid efflux (%) | NCP-1-pyrolipid | 1.0 ± 0.1 | 1.1 ± 0.1 | 1.1 ± 0.1 | 1.0 ± 0.1 |
| | porphysome | 1.2 ± 0.2 | 1.2 ± 0.1 | 1.2 ± 0.2 | 1.2 ± 0.1 |

Confocal scanning laser microscopy (CLSM) imaging and live cell imaging were also utilized to directly observe the cell internalization and lipid disassociation of NCP-1-pyrolipid. A 405 nm laser was used for visualizing the pyrolipid. Interestingly, no pyrolipid fluorescence was observed in the first 2-h incubation by CLSM and live cell imaging. The fluorescence appeared after ~2 h of incubation and increased with time. CLSM images also revealed that some of the pyrolipid was incorporated into cell membranes while the rest was distributed in the cytoplasm. As demonstrated earlier, NCP-1-pyrolipid with intact lipid layer exhibited nearly complete fluorescence quenching. Combining these results suggests that NCP-1-pyrolipid enters the cells in its intact form and maintains structural integrity in the first 2 h followed by lipid layer dissociation and intracellular lipid distribution to the cell membrane and cytoplasm. After incorporation into the cell membrane, pyrolipid might change the dynamics, porosity, and permeability of the cell membrane, which could lead to the reduced efflux of both cisplatin and pyrolipid for up to 24 h. This finding indicated that NCP-1-pyrolipid served as an efficient delivery vehicle for both cisplatin and pyrolipid, making NCP-1-pyrolipid a useful composition for combined chemotherapy and PDT.

In order to further investigate the intracellular fate of the core-shell nanostructures, 1 mol % of FITC-labeled 1,2-di-(9Z-octadecenoyl)-sn-glycero-3-phosphoethanolamine (FITC-DOPE) was doped during the lipid-coating of NCP-1 labeled with Chlorin e6 (NCP-1') to form NCP-1'-FITC-DOPE for observing the intracellular distribution of the solid core (red fluorescence coming from Chlorin e6, 405 nm laser) and lipid (green fluorescence coming form FITC-DOPE, 488 nm) upon the internalization by the cells. ImageJ was used to quantify the co-localization of red and green fluorescence to reveal the lipid disassociation kinetics. Results further confirmed that NCPs adsorb onto the cell membrane and enter the cells as intact core-shell nanostructures as evidenced by the 97.5±5.8% co-localization. Upon entering the cells, the lipid layers gradually disassociated from the core and part of the lipid was incorporated into the cell membrane while the rest was distributed in the cytoplasm.

4.4. Cytotoxicity of NCP-1-Pyrolipid Via Combined Chemotherapy and PDT:

Cisplatin causes cytotoxicity mainly by inducing apoptosis while PDT causes cytotoxicity via both apoptosis and necrosis pathways. By combining chemotherapy and PDT modalities into a single nanoparticle, NCP-1-pyrolipid can elicit both apoptosis and necrosis efficiently upon irradiation. The cisplatin prodrug in the core of NCP-1-pyrolpid is stable under physiological conditions, but can be readily reduced in the more reducing intracellular environment to release cisplatin in a triggered manner after endocytosis. The released cisplatin undergoes aquation and binds to DNA to induce apoptosis to lead to effective chemotherapy. NCP-1-pyrolipid is internalized by cells in its intact form and its lipid layer gradually disassociates from the solid core and is translocated to cell membrane or distributed in the cytoplasm. Because of the negligible efflux, cisplatin effectively induces cell apoptosis upon binding to DNA whereas pyrolipid accumulates in the cells at a high concentration to efficiently generate $^1O_2$ upon irradiation to cause cell death via both apoptosis and necrosis.

The cytotoxicity of NCP-1-pyrolipid was evaluated against four human head and neck cancer cells including cisplatin-sensitive HNSCC135 and SCC61 as well as cisplatin-resistant JSQ3 and SQ20B, and was compared with the cytotoxicity induced by NCP-1 (mono-chemotherapy) and porphysome (mono-PDT). Cisplatin $IC_{50}$ of NCP-1 and free cisplatin showed no significant difference in cells with or without irradiation, indicating that light does not affect the viability of cells treated with formulations without a PS (Table 10). The cytotoxicity of NCP-1-pyrolipid in cells without irradiation was similar to those of NCP-1 and free cisplatin, and porphysome alone induced no cytotoxicity in cells without irradiation. These results indicate that pyrolipid does not exhibit cytotoxicity without light activation. After irradiation, NCP-1-pyrolipid exhibited superior cytotoxicity to mono-chemotherapy (NCP-1) and mono-PDT (porphysome) as evidenced by its significantly decreased cisplatin and pyrolipid $IC_{50}$ values in all the four cancer cell lines (Table 10). In resistant SQ20B and JSQ3 cell lines, the cisplatin $IC_{50}$ values of NCP-1-pyrolipid with irradiation decreased by about an order of magnitude when compared to free cisplatin, NCP-1, and NCP-1-pyrolipid without irradiation. Upon irradiation, the pyrolipid $IC_{50}$ values of NCP-1-pyrolipid decreased by 8.0- and 6.2-fold compared with porphysome in SQ20B and JSQ3 cells, respectively. The enhanced cytotoxicity of NCP-1-pyrolipid upon light activation can be attributed to the synergistic effect of chemotherapy and PDT. These findings were further supported by the flow cytometry results (Table 11).

TABLE 10

Cisplatin and pyrolipid IC$_{50}$ values (μM) in four head and neck cancer cell lines treated with various formulations. The numbers in parenthesis refer to pyrolipid concentrations.

| | irradiation[a] | NCP-1-pyrolipid | NCP-1 | Free cisplatin | Porphysome[b] |
|---|---|---|---|---|---|
| HNSCC135 | Yes | 1.30 ± 0.05 (0.42 ± 0.02) | 2.71 ± 0.13 | 2.65 ± 0.13 | (0.63 ± 0.02) |
| | No | 3.25 ± 0.46 (1.05 ± 0.15)[c] | 2.71 ± 0.16 | 3.37 ± 0.73 | N/A |
| JSQ3 | Yes | 1.21 ± 0.03 (0.39 ± 0.01) | 14.51 ± 1.40 | 13.33 ± 2.03 | (2.42 ± 0.68) |
| | No | 11.39 ± 0.22 (3.67 ± 0.07)[c] | 12.42 ± 0.40 | 11.31 ± 1.20 | N/A |
| SCC61 | Yes | 0.77 ± 0.03 (0.25 ± 0.01) | 3.11 ± 0.32 | 3.69 ± 0.28 | (0.50 ± 0.02) |
| | No | 3.48 ± 0.64 (1.12 ± 0.21)[c] | 3.10 ± 0.53 | 3.46 ± 0.08 | N/A |
| SQ20B | Yes | 0.41 ± 0.02 (0.13 ± 0.01) | 4.22 ± 0.11 | 4.18 ± 0.11 | (1.04 ± 0.02) |
| | No | 3.97 ± 0.38 (1.28 ± 0.12)[c] | 3.93 ± 0.38 | 3.92 ± 0.15 | N/A |

[a]Cells were irradiated with LED light (670 nm) at 60 mW/cm$^2$ for 15 min (equals to 54 J/cm$^2$).
[b]Porphysome containing no cisplatin served as controls. The amount of pyrolipid in the porphysome was the same as NCP-1-pyrolipid under the studied concentrations.
[c]The dark cytotoxicity comes entirely from the action of cisplatin in these formulations.

TABLE 11

Apoptosis and necrosis levels of SQ20B cells treated with NCP-1-pyrolipid with or without irradiation.

| | w/irradiation | | w/o irradiation | |
|---|---|---|---|---|
| | Apoptosis %[a] | Necrosis %[b] | Apoptosis %[a] | Necrosis %[b] |
| PBS | 0.1 | 0.1 | 0.1 | 0.7 |
| Free cisplatin | 38.1 | 0.2 | 37.9 | 0.2 |
| NCP-1 | 25.4 | 0.7 | 31.5 | 0.6 |
| Porphysome | 11.4 | 17.4 | 1.0 | 1.6 |
| NCP-1-pyrolipid | 26.0 | 14.5 | 31.7 | 0.7 |

[a]Sum of percentages in upper and lower right quadrants.
[b]Percentage in upper left quadrant.

4.5. In Vivo Pharmacokinetic and Biodistribution Studies:

A pharmacokinetic (PK) study of NCP-1-pyrolipid was conducted on CT26 tumor bearing mice to determine the blood circulation time and biodistribution profiles. The Pt distribution was quantified (Table 12) by ICP-MS and the pyrolipid amount in the blood was quantified by UV-vis spectroscopy after extraction by methanol. The pyrolipid quantification method was first validated by showing nearly complete recovery of pyrolipid from blood upon methanol extraction. Both Pt and pyrolipid concentrations in blood versus time were fitted best by a one-compartment model with nonlinear elimination. The cisplatin and pyrolipid concentrations in blood were similar up to 48 h post intravenous injection, suggesting the lipid bilayer of NCP-1-pyrolipid remained intact in systemic circulation. Blood circulation half-lives of Pt and pyrolipid were determined to be (9.0±1.8) and (6.7±2.2) h, respectively, and did not exhibit a statistically significant difference (Table 13).

TABLE 12

| | Pt (% dose/g) | | | | | |
|---|---|---|---|---|---|---|
| | 5 min | 1 h | 3 h | 8 h | 24 h | 48 h |
| liver | 2.2 ± 0.9 | 3.7 ± 1.9 | 6.0 ± 1.4 | 9.2 ± 0.1 | 7.5 ± 2.0 | 3.5 ± 0.8 |
| lung | 5.7 ± 3.0 | 3.0 ± 0.8 | 5.5 ± 1.2 | 4.8 ± 0.5 | 3.6 ± 0.1 | 1.2 ± 0.3 |
| spleen | 6.5 ± 4.7 | 5.8 ± 4.3 | 12.6 ± 5.6 | 7.6 ± 7.0 | 16.7 ± 3.5 | 13.0 ± 3.7 |
| kidney | 2.3 ± 2.5 | 3.7 ± 2.9 | 3.5 ± 0.8 | 4.4 ± 0.1 | 5.6 ± 1.0 | 2.9 ± 0.4 |
| bladder | 3.8 ± 1.2 | 1.4 ± 2.4 | 1.8 ± 0.6 | 0.7 ± 1.1 | 1.6 ± 0.2 | 0.9 ± 0.2 |
| tumor | 1.5 ± 0.4 | 3.3 ± 1.3 | 3.1 ± 0.4 | 3.8 ± 0.5 | 23.2 ± 2.4 | 9.1 ± 1.7 |
| plasma | 51.6 ± 7.3 | 48.0 ± 3.7 | 39.5 ± 1.2 | 28.8 ± 0.9 | 9.9 ± 2.1 | 0.4 ± 0.1 |

TABLE 13

Pyrolipid and cisplatin concentrations in blood (μg/g)

|  | pyrolipid | cisplatin |
|---|---|---|
| 5 min | 35.4 ± 2.1 | 31.0 ± 4.4 |
| 1 h | 29.4 ± 8.7 | 28.6 ± 7.5 |
| 3 h | 23.0 ± 3.0 | 23.7 ± 0.7 |
| 8 h | 12.9 ± 4.9 | 13.5 ± 3.7 |
| 24 h | 6.1 ± 1.7 | 5.9 ± 1.3 |
| 48 h | 0.9 ± 0.3 | 0.3 ± 0.1 |

In addition to the prolonged blood circulation time, tissue distribution profiles of NCP-1-pyrolipid showed its ability to avoid uptake by the mononuclear phagocyte system (MPS) as evidenced by the low % ID/g (percent injected dose/gram tissue) in liver (<9.2±0.1%), spleen (<16.7±3.5%), and kidney (<5.6±0.9%). The slow blood clearance and low MPS uptake led to the high tumor accumulation of drug, with a peak tumor uptake of 23.2±2.4% ID/g 24 h post administration. The exceptionally high tumor uptake of cisplatin for the NCP-1-pyrolipid can be partially attributed to the reduced cisplatin efflux due to the incorporation of pyrolipid into cell membranes.

Other NCP-1-pyrolipid formulations with different lipid compositions were tested. For example, an NCP-1-pyrolipid formulation with pyrolipid, cholesterol (pyrolipid/cholesterol molar ratio=1:1), and 20 mol % DSPE-PEG in the outer lipid layer exhibited a blood circulation half-life of 1.55 h after intravenous injection.

4.6. Antitumor Activity in SQ20B Xenograft Murine Models:

The cisplatin-resistant SQ20B human head and neck cancer subcutaneous xenograft murine model was employed to assess the in vivo antitumor activity of NCP-1-pyrolipid. All doses were based on free cisplatin or pyrolipid equivalents. SQ20B tumor bearing mice were treated by intravenous injection of: (1) PBS, (2) NCP-1 at a cisplatin dose of 0.5 mg/kg, (3) porphysome at a pyrolipid dose of 0.5 mg/kg, or (4) and (5) NCP-1-pyrolipid at a cisplatin or pyrolipid dose of 0.5 mg/kg once a week for twice, with (5) or without (4) irradiation. Twenty four hours post injection, mice in group (1)-(3) and (5) were anesthetized with 2% (v/v) isoflurane and tumors were irradiated with a 670 nm LED (100 mW/cm$^2$) for 30 min. Only NCP-1-pyrolipid plus irradiation (Group 5) showed significant tumor suppression in cisplatin resistant SQ20B tumors, with a reduction of tumor volume by ~83% (Table 14). Mice in the other four groups shared the similar tumor growth pattern, suggesting that mono-chemotherapy or mono-PDT was incapable of inhibiting tumor growth or regression in the cisplatin-resistant SQ20B tumor model. Mice treated with NCP-1-pyrolipid but without irradiation (Group 4) showed no tumor growth inhibition, indicating NCP-1-pyrolipid achieved anticancer effect in a light-triggered manner. The tumor weight of NCP-1-pyrolipid with irradiation was ~62-fold smaller than that of control with irradiation group, with a P value of 0.001815 by one-way ANOVA test (Table 15). The combination therapy did not cause body weight loss or skin damage in the irradiation region indicating the doses of drug and light are safe.

TABLE 14

Tumor growth curve (cm$^3$)

|  | PBS(+) | NCP-1(+) | Porphysome(+) | NCP-1-pyrolipid(−) | NCP-1-pyrolipid(+) |
|---|---|---|---|---|---|
| Day 0 | 0.13 ± 0.01 | 0.13 ± 0.01 | 0.13 ± 0.01 | 0.14 ± 0.01 | 0.13 ± 0.01 |
| Day 1 | 0.18 ± 0.01 | 0.15 ± 0.01 | 0.14 ± 0.01 | 0.17 ± 0.03 | 0.15 ± 0.01 |
| Day 2 | 0.21 ± 0.03 | 0.17 ± 0.05 | 0.16 ± 0.02 | 0.21 ± 0.05 | 0.12 ± 0.01 |
| Day 3 | 0.26 ± 0.06 | 0.23 ± 0.03 | 0.18 ± 0.06 | 0.27 ± 0.04 | 0.04 ± 0.01 |
| Day 4 | 0.38 ± 0.12 | 0.32 ± 0.04 | 0.22 ± 0.10 | 0.40 ± 0.05 | 0.02 ± 0.01 |
| Day 5 | 0.44 ± 0.15 | 0.39 ± 0.10 | 0.37 ± 0.06 | 0.49 ± 0.08 | 0.02 ± 0.01 |
| Day 6 | 0.55 ± 0.17 | 0.53 ± 0.17 | 0.41 ± 0.08 | 0.65 ± 0.11 | 0.02 ± 0.01 |
| Day 7 | 0.61 ± 0.13 | 0.63 ± 0.17 | 0.61 ± 0.14 | 0.73 ± 0.06 | 0.02 ± 0.01 |
| Day 8 | 0.82 ± 0.25 | 0.75 ± 0.27 | 0.80 ± 0.13 | 0.85 ± 0.15 | 0.02 ± 0.01 |
| Day 9 | 1.13 ± 0.36 | 1.05 ± 0.15 | 1.01 ± 0.14 | 0.97 ± 0.26 | 0.02 ± 0.01 |
| Day 10 | 1.24 ± 0.26 | 1.25 ± 0.15 | 1.18 ± 0.42 | 1.26 ± 0.35 | 0.02 ± 0.01 |
| Day 11 | 1.40 ± 0.20 | 1.39 ± 0.16 | 1.50 ± 0.50 | 1.53 ± 0.33 | 0.02 ± 0.01 |
| Day 12 | 1.60 ± 0.37 | 1.47 ± 0.07 | 1.77 ± 0.58 | 1.64 ± 0.54 | 0.02 ± 0.01 |

(+) = irradiation,
(−) = no irradiation

TABLE 15

Tumor weight (g)

| PBS(+) | 1.3 ± 0.6 |
|---|---|
| NCP-1(+) | 0.9 ± 0.1 |
| Porphysome(+) | 0.8 ± 0.3 |
| NCP-1-pyrolipid(−) | 1.4 ± 0.4 |
| NCP-1-pyrolipid(+) | 0.02 ± 0.01 |

4.7. Histopathology Analysis, In Vivo Apoptosis, and Immunoresponse:

NCP-1-pyrolipid exhibited exceptional tumor suppression activity against the cisplatin-resistant human head and neck cancer SQ20B xenograft murine model. A histopathology analysis of resected tumors further confirmed the antitumor potency of NCP-1-pyrolipid. Tumors of mice treated with NCP-1-pyrolipid and irradiation showed large areas of apoptosis and necrosis, while mice receiving other treatments had tumors with large regions of viable cancer cells and massive vasculature structures. PDT eradicates tumors through three main mechanisms: inducing apoptosis/necrosis, activating immune response against tumor cells, and disrupting the tumor vasculature structures to deprive the tumor of oxygen and nutrients. Macrophages (smaller nuclei stained with darker blue), infiltration and broken blood vessels were observed in the tumors of mice receiving NCP-1-pyrolipid and light treatments. A TUNEL assay was performed on the resected tumors to further substantiate and quantify the in vivo apoptosis. As quantified in Table 16, the fluorescence intensity of DNA fragmentation and the relative percentage of apoptotic cells in the NCP-1-pyrolipid with irradiation were significantly higher than those in the other groups. NCP-1-pyrolipid with irradiation induced 74.8±4.9% tumor cell apoptosis while the other four groups caused <3.5% apoptosis. Furthermore, no changes in histology were observed for liver, kidneys, lungs, and spleen in mice receiving NCP-1-pyrolipid and irradiation compared to the control group, suggesting low toxicity to vital organs.

TABLE 16

| TUNEL positive cells (%) | |
|---|---|
| PBS(+) | 0.6 ± 0.2 |
| NCP-1(+) | 1.9 ± 1.3 |
| Porphysome(+) | 1.0 ± 0.4 |
| NCP-1-pyrolipid(−) | 3.4 ± 1.7 |
| NCP-1-pyrolipid(+) | 74.8 ± 4.9 |

In order to evaluate the immunoresponse evoked by the combination of chemotherapy and PDT, mouse blood was collected at the endpoint and the serum was separated for the determination of TNF-α, IL-6, and IFN-γ production by enzyme-linked immunosorbent assay (ELISA). No significant difference was observed for the three pro-inflammatory cytokine levels among control and monotherapy groups while slightly higher TNF-α (P=0.047288 vs. control) and IL-6 (P=0.031826 vs. control) were noted for NCP-1-pyrolipid with irradiation, which could be due to the immunoresponse evoked by PDT (Table 17).

TABLE 17

| | Cytokine concentrations in serum (ng/L) | | | | |
|---|---|---|---|---|---|
| | PBS(+) | NCP-1(+) | Porphysome(+) | NCP-1-pyrolipid(−) | NCP-1-pyrolipid(+) |
| IL-6 | 19.6 ± 2.0 | 19.9 ± 1.9 | 20.3 ± 0.9 | 18.0 ± 1.0 | 24.9 ± 2.0 |
| TNF-α | 5.8 ± 1.9 | 7.2 ± 1.8 | 7.7 ± 1.6 | 7.2 ± 1.6 | 12.5 ± 3.6 |
| IFN-γ | 9.0 ± 3.4 | 9.4 ± 0.5 | 10.7 ± 2.0 | 10.3 ± 2.1 | 11.7 ± 1.1 |

4.8. Summary:

In certain embodiments, NCP-1-pyrolipid nanoparticles carry 25 wt % cisplatin in the core and 25 wt % pyrolipid on the shell, and are capable of delivering large amounts of both chemotherapeutic agents and PSs. In addition, NCP-1-pyrolipid released its payloads in a triggered manner in the site of actions. In the extracellular environment, NCP-1-pyrolipid maintained its structural integrity. Upon entering cells, the lipid layer gradually dissociated from the solid core of NCP-1-pyrolipid within 2 h with some pyrolipid fused into cell membrane and the rest remaining in the cytoplasm. After shedding the lipid layer intracellularly, the NCP-1 core became highly permeable to high concentrations of endogenous reducing agents such as cysteine and glutathione to trigger release of cisplatin via reductive cleavage of the metal-ligand bonds in NCP-1.

After intravenous injection to tumor bearing mice, NCP-1-pyrolipid exhibited prolonged blood circulation half-lives for both of its therapeutic payloads: the $t_{1/2}$ for cisplatin is 9.0±1.8 h and the $t_{1/2}$ for pyrolipid is 6.7±2.2 h. This PK can be attributed to the small particle size (~100 nm), high PEG coating (~20 mol %), and favorable structural stability of NCP-1-pyrolipid in extracellular environments. As a result, NCP-1-pyrolipid achieved as high as ~23 ID %/g cisplatin accumulation in the tumor 24 h post i.v. injection, with low uptake by the MPS system and minimal non-specific organ distributions.

NCP-1-pyrolipid not only exhibited efficient and highly specific tumor deposition, but also showed high uptake and accumulation in the cancer cells. The cellular uptake amounts of cisplatin and pyrolipid of NCP-1-pyrolipid incubated with SQ20B cells were similar and stable over the 24-h experiments. Meanwhile, negligible efflux of cisplatin and pyrolipid was observed for NCP-1-pyrolipid in SQ20B cells throughout the 24-h incubation time. CLSM images also provided evidence that pyrolipid was partly incorporated into the cell membrane and partly retained in the cytoplasm, instead of being recycled out of the cells after disassociation from the solid core of NCP-1-pyrolipid. Without being bound to any one theory, the incorporation of pyrolipid into cell membranes could be partly responsible for the negligible cisplatin efflux from cancer cells.

Combination therapy offers opportunities to treat cancers via different mechanisms of actions, thus leading to enhanced anticancer efficacy via synergistic effects. NCP-1-pyrolipid combines the superior chemotherapy efficacy of cisplatin and potent PDT efficacy of pyrolipid in one single platform and enhanced the anticancer efficacy in cisplatin-resistant head and neck cancer both in vitro and in vivo. This synergistic effect was substantiated by the following results: (1) significantly decreased cisplatin $IC_{50}$ of NCP-1-pyrolipid with irradiation when compared to free cisplatin, NCP-1, porphysome with or without irradiation and NCP-1-pyrolipid without irradiation in the four human head and neck cancer cell lines tested; and (2) no tumor inhibition was observed for SQ20B tumor bearing mice treated with PBS with irradiation, NCP-1 with irradiation, porphysome with irradiation, and NCP-1-pyrolipid without irradiation while the tumors of mice receiving NCP-1-pyrolipid and irradiation shrank by ~83% in volume.

For the present in vivo anticancer efficacy study, the mice were intravenously injected with NCP-1-pyrolipid at a cisplatin dose of 0.5 mg/kg and a pyrolipid dose of 0.5 mg/kg once a week for twice. As indicated by histopathological analysis results, this very low drug dose does not cause in vivo toxicity or severe adverse systemic immunoresponse that often occurs for PDT.

Example 5

Nanoparticle Coordination Polymers Particles with siRNAs 5.1. Preparation and Characterization of Pten-NCP/siRNAs:

Pten was synthesized as a nontoxic analog to the cisplatin prodrug PtBp based on previously reported procedures (see Liu et al., *Nature Communications* 2014; 5: 4128). Briefly, [Pt(en)$_2$]Cl$_2$ was prepared by treating K$_2$PtCl$_4$ with ethylenediamine (en) in aqueous solution. [Pt(en)$_2$]Cl$_2$ was then oxidized by hydrogen peroxide to afford [Pt(en)$_2$(OH)$_2$]Cl$_2$, which was treated with diethoxyphosphinyl isocyanate followed by deprotection of the phosphonate esters with bromotrimethylsilane to afford Pten. The solid core of Pten-NCP is a 1,2-dioleoyl-sn-glycero-3-phosphate (DOPA)-capped NCP constructed from Pten and $Zn^{2+}$ ions in reverse microemulsions. The lipid-coating strategy described in Liu et al. (*Nature Communications* 2014; 5: 4128) and elsewhere herein was used to form a highly oriented and asymmetric lipid bilayer on the surface of Pten-NCP, composed of 1,2-dioleoyl-sn-glycero-3-phosphatidylcholine (DOPC), cholesterol, and 20 mol % 1,2-distearoyl-sn-glycero-3-phosphoethanolamine-N-[amino(polyethylene glycol)$_{2000}$] (DSPE-PEG2k). siRNAs were incorporated in the shell where they were shielded with the PEG layer to prevent nuclease degradation in physiological environments. N-succinimidyl-3-(2-pyridyldithio)propionyl-1,2-distearoyl-sn-glycero-3-phosphoethanolamine (DSPE-SPDP) was synthesized from succinimidyl 3-(2-pyridyldithio)propionate and 1,2-distearoyl-sn-glycero-3-phosphoethanolamine, and further conjugated with thiol siRNA (Integrated DNA Technologies, Coralville, Iowa, United States of America) to afford the DSPE-siRNA conjugate. The disulfide linkage is placed on the 5' end of the sense strand of siRNA duplexes in order to avoid potential inhibition on the antisense strand. siRNA is incorporated into the lipid layer via non-covalent self-assembly at a Pt to siRNA molar ratio of 160:1 to obtain Pten-NCP/siRNAs. Thus, Pten-NCP/siRNAs provides sufficient protection to siRNAs extracellularly while the siRNA release can be triggered in the reducing environment intracellularly by the cleavage of disulfide bond.

Dynamic light scattering (DLS) measurements gave a diameter and PDI of 31.4±2.4 nm and 0.19 for Pten-NCP and 80.7±2.9 nm and 0.15 for Pten-NCP/siRNAs, respectively. The Pt loading is 15.7 wt % by inductively coupled plasma-mass spectrometry (ICP-MS). The siRNA loading in Pten-NCP/siRNAs was determined to be 1.5 wt % by Quant-iT RiboGreen RNA kit (Invitrogen, Carlsbad, Calif., United States of America), and can be increased to as high as 6% based on our previous experience. TEM images show that Pten-NCP is spherical and mono-dispersed. See FIG. 9(a).

Efficient endosomal escape upon entering the cells via endocytosis is preferred for triggering siRNA-mediated gene silencing. The proton sponge effect has been extensively exploited as an endosomal escape mechanism for siRNA nanocarriers, but the realization of this effect typically employs cationic components which tend to adversely impact the blood circulation and biodistribution of the nanocarriers via systemic administration. Pten-NCP/siRNAs has a novel built-in endosomal escape mechanism without involving cationic excipients. For Pten-NCP/siRNAs, the intracellular release of each Pt(en)$_2^{2+}$ from Pten-NCP also generates two $CO_2$ molecules. See FIG. 9(c). Without wishing to be bound by theory, it is hypothesized that the $CO_2$ generated from NCP can disrupt the endosome membrane by changing the osmotic pressure, facilitating siRNA escape from endosomal entrapment and triggering the formation of RNA-induced silencing complex (RISC) in the cytoplasm to mediate gene silencing.

Alexa Fluor 647 labeled siRNA was used to prepare Pten-NCP/Alexa-siRNAs. SKOV-3 cells were incubated with Pten-NCP/Alexa-siRNAs for different time periods, fixed, stained with Lysotracker Green and DAPI, and observed by CLSM. The co-localization of green fluorescence (Lysotracker Green stained endosome) and red fluorescence (Alexa Fluor 647 labeled siRNA) was calculated by ImageJ. Pten-NCP/Alexa-siRNAs was internalized by the cells rapidly, and siRNA escaped from endosome entrapment within 2 h as evidenced by the gradual decrease of co-localization of siRNA and endo/lysosome fluorescence. See FIG. 9(b).

Particles of Pten-NCP are constructed from Pten and Zn ions with a biocompatible lipid monolayer. The cytotoxicity of Pten and Pten-NCP against H460 cells was determined. Pten or Pten-NCP induced no cytotoxicity at a Pt concentration of up to 50 μM while cisplatin has an $IC_{50}$ of 4.8 μM. See FIG. 10(a). This result shows that Pten or Pten-NCP alone is non-cytotoxic and safe to use as a nanocarrier.

5.2. In Vitro Transfection Efficiency of Pten-NCP/siRNAs:

A2780/CDDP is a cisplatin-resistant OCa cell line with overexpression of Bcl-2 and survivin. siRNAs targeting Bcl-2 and survivin were loaded into particles of Pten-NCP to form Pten-NCP/siRNAs. A2780/CDDP cells were incubated with Pten-NCP/siRNAs at a siRNA dose of 30 nM for 24 h, and the gene silencing efficiency mediated by Pten-NCP/siRNAs was evaluated by quantifying the protein production of Bcl-2 and survivin by enzyme-linked immunosorbent assay (ELISA). The Bcl-2 and survivin protein production was down-regulated by ~60% compared to the PBS control. See FIG. 10(b). This result shows that Pten-NCP siRNAs can mediate efficient gene silencing in OCa cells.

Since the synthesis of Pten-NCP/siRNAs is highly modular, any combination of siRNAs or individual siRNA can be efficiently incorporated into the particles by using a cocktail of DSPE-siRNA conjugates. Pten-NCP/siRNAs loaded with PD-L1 siRNA, CCR-7 siRNA, and IDO siRNA, either individually or as a pool, can mediate efficient in vitro gene silencing. A pool of siRNAs targeting PD-L1, CCR7, and/or IDO can be incorporated into particles of Pten-NCP via similar loading strategies to those described hereinabove.

Example 6

NCP/siRNAs Carrying Cisplatin Plus Gemcitabine and siRNAs

DOPA-coated NCP particles carrying cisplatin and gemcitabine monophosphate (GMP) were synthesized using a similar procedure as for DOPA-coated NCP carrying cisplatin, except that both cisplatin prodrug and GMP were used in the reverse microemulsion reaction. The particles of NCP have cisplatin and gemcitabine loadings of 15 wt % and 27 wt %, respectively, as determined by ICP-MS and TGA. The Z-average diameter and PDI of NCP were 42.4±0.1 nm and 0.116, respectively. The DOPA-coated NCP particles were coated with DOPC, cholesterol, 25 mol % DSPE-PEG2k, and DSPE-siRNA at a cisplatin:GMP:siRNA weight ratio of 2:4:1. The Z-average size, PDI, and zeta potential of NCP/siRNAs are 101.3±1.4 nm, 0.206, and −3.4±0.1 mV, respectively. TEM images show that NCP/siRNAs are spherical and mono-dispersed nanostructure in PBS. See FIG. 8(a). The release of cisplatin and GMP from NCP/siRNAs was evaluated, and the cisplatin release was significantly enhanced in the presence of cysteine. See FIG. 8(b) and FIG. 8(c).

The cytotoxicity of NCP particles carrying cisplatin, GMP, and thiol siRNAs targeting survivin, Bcl-2, and ERCC-1 were evaluated against human ovarian cancer cells A2780, A2780/CDDP, SKOV-3 and human non-small cell lung cancer cell H460 by MTS assay. See Table 18.

TABLE 18

Cisplatin IC$_{50}$ values of cisplatin, GMP, and NCP against A2780, A2780R, SKOV-3, and H460 cells (the numbers in parenthesis refer to GMP concentrations).

| | Cisplatin (μM) | GMP (μM) | Zn Control* (μM) | NCP (μM) | NCP/siRNAs (μM) |
|---|---|---|---|---|---|
| A2780 | 0.764 ± 0.183 | (0.032 ± 0.0.004) | >5000 (>5000) | 0.107 ± 0.015 (0.210 ± 0.029) | 0.25 ± 0.02 (0.47 ± 0.05) |
| A2780R | 13.6 ± 3.2 | (0.12 ± 0.01) | >25 (>10) | 0.17 ± 0.01 (0.26 ± 0.01) | 0.051 ± 0.005 (0.16 ± 0.01) |
| SKOV-3 | 4.6 ± 0.7 | (2.8 ± 0.8) | >50 (>50) | 0.84 ± 0.15 (1.8 ± 0.4) | |
| H460 | 4.6 ± 0.6 | (3.3 ± 1.3) | >50 >50 | 1.7 ± 0.6 (3.3 ± 1.2) | |

*Zn Control does not contain oxaliplatin or GMP. The amount of Zn Control particle was the same as NCP-5 under the studied concentrations. Data are expressed as means ± SD.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A nanoscale particle for co-delivery of a plurality of therapeutic agents, wherein the plurality of therapeutic agents comprise at least one non-nucleic acid chemotherapeutic agent and at least one nucleic acid therapeutic agent, said nanoscale particle comprising:
   a core comprising a metal bisphosphonate coordination polymer comprising a multivalent metal ion and a bisphosphonate, wherein the bisphosphonate is a prodrug of a platinum-based chemotherapeutic agent; and wherein the core is coated with a lipid bilayer comprising (i) a cationic lipid, wherein at least one nucleic acid therapeutic agent is attached to the cationic lipid via electrostatic interactions; or (ii) a functionalized lipid, wherein said functionalized lipid is a thiol- or dithiol-functionalized lipid covalently bonded to at least one nucleic acid therapeutic agent.

2. The nanoscale particle of claim 1, wherein the at least one nucleic acid therapeutic agent is a siRNA, a miRNA, or an AS ODN.

3. The nanoscale particle of claim 2, wherein the at least one nucleic acid therapeutic agent is selected from the group consisting of survivin siRNA, ERCC-1 siRNA, P-glycoprotein siRNA (P-gp siRNA), Bcl-2 siRNA, or a mixture thereof.

4. The nanoscale particle of claim 1, wherein the lipid bilayer further comprises: a passivating agent; a targeting agent; and/or an imaging agent.

5. The nanoscale particle of claim 1, wherein the multivalent metal ion is selected from the group consisting of $Ca^{2+}$, $Mg^{2+}$, $Mn^{2+}$, $Zn^{2+}$, and combinations thereof.

6. The nanoscale particle of claim 1, wherein the bisphosphonate is a cisplatin or oxaliplatin prodrug.

7. The nanoscale particle of claim 6, wherein the bisphosphonate is an oxaliplatin prodrug.

8. The nanoscale particle of claim 6, wherein the bisphosphonate is a cisplatin prodrug.

9. A method of treating cancer in a subject in need thereof, the method comprising administering to the subject a composition comprising a nanoscale particle of claim 1.

10. The method of claim 9, wherein the cancer is selected from lung cancer, pancreatic cancer, ovarian cancer, breast cancer and colon cancer.

11. The method of claim 9, wherein the cancer is ovarian cancer, optionally a cisplatin resistant ovarian cancer.

12. A method of preparing a nanoscale particle of claim 1, the method comprising:
   (a) contacting a microemulsion comprising a metal ion with a microemulsion comprising a bisphosphonate, optionally wherein the bisphosphonate is a cisplatin or oxaliplatin prodrug, thereby forming a metal bisphosphonate coordination polymer nanoparticle;
   (b) dispersing the nanoparticle from (a) in a solution comprising a cationic lipid and/or a functionalized lipid to form a cationic lipid-coated and/or functionalized lipid coated nanoparticle; and
   (c) contacting the lipid-coated nanoparticles with a solution comprising at least one nucleic acid therapeutic agent.

13. A pharmaceutical formulation comprising a nanoscale particle of claim 1 and a pharmaceutically acceptable carrier.

* * * * *